United States Patent
Lim et al.

(10) Patent No.: US 10,290,812 B2
(45) Date of Patent: May 14, 2019

(54) COMPOUND FOR ORGANIC PHOTOELECTRIC DEVICE AND ORGANIC PHOTOELECTRIC DEVICE IMAGE SENSOR, AND ELECTRONIC DEVICE INCLUDING THE SAME

(71) Applicant: Samsung Electronics Co., Ltd., Suwon-si, Gyeonggi-do (KR)

(72) Inventors: Seon-Jeong Lim, Yongin-si (KR); Takkyun Ro, Hwaseong-si (KR); Tadao Yagi, Hwaseong-si (KR); Kyung Bae Park, Hwaseong-si (KR); Sung Young Yun, Suwon-si (KR); Yong Wan Jin, Seoul (KR); Chul-Joon Heo, Busan (KR)

(73) Assignee: Samsung Electronics Co., Ltd., Gyeonggi-Do (KR)

( * ) Notice: Subject to any disclaimer, the term of this patent is extended or adjusted under 35 U.S.C. 154(b) by 321 days.

(21) Appl. No.: 14/951,718

(22) Filed: Nov. 25, 2015

(65) Prior Publication Data

US 2016/0149132 A1 May 26, 2016

(30) Foreign Application Priority Data

Nov. 25, 2014 (KR) ........................ 10-2014-0165400

(51) Int. Cl.
| | | |
|---|---|---|
| H01L 51/00 | (2006.01) |
| H01L 27/30 | (2006.01) |
| C07D 345/00 | (2006.01) |
| C07D 333/48 | (2006.01) |
| C07D 421/06 | (2006.01) |
| C07D 333/36 | (2006.01) |
| C07F 7/08 | (2006.01) |
| C09B 23/04 | (2006.01) |
| C09B 47/00 | (2006.01) |
| C09B 57/00 | (2006.01) |
| H01L 51/44 | (2006.01) |
| H01L 51/42 | (2006.01) |

(52) U.S. Cl.
CPC .......... *H01L 51/006* (2013.01); *C07D 333/36* (2013.01); *C07D 333/48* (2013.01); *C07D 345/00* (2013.01); *C07D 421/06* (2013.01); *C07F 7/081* (2013.01); *C09B 23/04* (2013.01); *C09B 47/00* (2013.01); *C09B 57/00* (2013.01); *C09B 57/008* (2013.01); *H01L 27/307* (2013.01); *H01L 51/0053* (2013.01); *H01L 51/0061* (2013.01); *H01L 51/0062* (2013.01); *H01L 51/0068* (2013.01); *H01L 51/0094* (2013.01); *H01L 51/0058* (2013.01); *H01L 51/0067* (2013.01); *H01L 51/42* (2013.01); *H01L 51/447* (2013.01); *Y02E 10/549* (2013.01)

(58) Field of Classification Search
None
See application file for complete search history.

(56) References Cited

U.S. PATENT DOCUMENTS

| | | | |
|---|---|---|---|
| 8,525,577 B2 | 9/2013 | Yofu et al. |
| 9,070,887 B2 | 6/2015 | Yofu et al. |
| 9,666,810 B2 * | 5/2017 | Yun ..................... H01L 51/4253 |
| 2011/0074491 A1 | 3/2011 | Yofu et al. |
| 2013/0299799 A1 | 11/2013 | Yofu et al. |
| 2015/0065343 A1 | 3/2015 | Bindschaedler et al. |
| 2015/0076420 A1 | 3/2015 | Kaneko et al. |

FOREIGN PATENT DOCUMENTS

| | | | | |
|---|---|---|---|---|
| CN | 102034933 A | | 4/2011 | |
| EP | 3113225 | * | 1/2017 | ............. H01N 27/30 |
| JP | 2008-184433 A | | 8/2008 | |
| JP | 2009-084251 A | | 4/2009 | |
| KR | 2014143652 | * | 10/2014 | |
| WO | WO-1992-009580 A1 | | 6/1992 | |
| WO | WO 200221611 | * | 3/2002 | ........... C07D 305/06 |
| WO | WO-2013-147145 A1 | | 10/2013 | |
| WO | WO-2013-149940 A1 | | 10/2013 | |

OTHER PUBLICATIONS

Lennen. Macromolecular Chemistry and Physics, 2010, 211, 2286-91.*
Chen, et al. "Comparison of thiophene- and selenophene-bridged donor-acceptor low band-gap copolymers used in bulk-heteojunction organic photovoltaics," Journal of Materials Chemistry, vol. 22, pp. 2159-21559, (2012).
F. A. Mikhailenko, et al. "Mono- and dimethine dyes from 2-dimethylamino-5-formylfurans, -thiophenes, and -selenphenes," Institute of Organic Chemistry, Academy of Sciences of the Ukranian SSSR, No. 3, pp. 316-320 (1975).
Extended European Search Report dated Apr. 4, 2016 issued in corresponding European Patent Application No. 15196179.4.
J. Stradins et al., "The Polarographic Behaviour of Derivativies of 2-Nitroselenophen", Latvijas PSR Zinatnu Akademijas Vestis (1960), (No. 3), 85-92.
Chinese Office Action dated Jul. 19, 2018 of corresponding Chinese Patent Application No. 201510828964.X.

* cited by examiner

*Primary Examiner* — Noble E Jarrell
(74) *Attorney, Agent, or Firm* — Harness, Dickey & Pierce, P.L.C.

(57) ABSTRACT

A compound for an organic photoelectric device is represented by Chemical Formula 1, and an organic photoelectric device, an image sensor and an electronic device include the same.

22 Claims, 22 Drawing Sheets

COMPOUND FOR ORGANIC PHOTOELECTRIC DEVICE AND ORGANIC PHOTOELECTRIC DEVICE IMAGE SENSOR, AND ELECTRONIC DEVICE INCLUDING THE SAME

CROSS-REFERENCE TO RELATED APPLICATION

This application claims priority to and the benefit of Korean Patent Application No. 10-2014-0165400 filed in the Korean Intellectual Property Office on Nov. 25, 2014, the entire contents of which are incorporated herein by reference.

BACKGROUND

1. Field

Example embodiments provide a compound for an organic photoelectric device, and an organic photoelectric device, an image sensor, and an electronic device including the same.

2. Description of the Related Art

A photoelectric device converts light into an electrical signal using photoelectric effects. The photoelectric device may include a photodiode, a phototransistor, etc., and may be applied to an image sensor, an organic light emitting diode, etc.

An image sensor including a photodiode requires higher resolution and thus a smaller pixel. At present, a silicon photodiode is widely used, but has a problem of deteriorated sensitivity since the silicon photodiode has a smaller absorption area due to smaller pixels. Accordingly, an organic material that is capable of replacing silicon has been researched.

The organic material has a relatively high extinction coefficient and selectively absorbs/sense light in a particular wavelength region depending on a molecular structure, and thus may simultaneously replace a photodiode and a color filter, thereby improving sensitivity and contributing to relatively high integration.

SUMMARY

Example embodiments provide a compound for an organic photoelectric device being capable of sensing light in a green wavelength region and having improved thermal stability.

Example embodiments also provide an organic photoelectric device being capable of sensing light in a green wavelength region and improving efficiency.

Example embodiments also provide an image sensor including the organic photoelectric device.

Example embodiments also provide an electronic device including the image sensor.

According to example embodiments, a compound for an organic photoelectric device is represented by Chemical Formula 1.

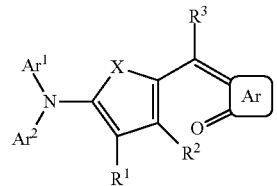

[Chemical Formula 1]

In Chemical Formula 1,

Ar is one of a substituted or unsubstituted 5-membered aromatic ring, a substituted or unsubstituted 6-membered aromatic ring, and a condensed ring of two or more of the foregoing rings, X is one of Se, Te, S(=O), S(=O)$_2$, and SiR$^a$R$^b$ (wherein R$^a$ and R$^b$ are independently one of hydrogen and a substituted or unsubstituted C$_1$ to C$_{10}$ alkyl group), each of Ar$^1$ and Ar$^2$ are independently one of a substituted or unsubstituted C$_6$ to C$_{30}$ aryl group and a substituted or unsubstituted C$_3$ to C$_{30}$ heteroaryl group, and each of R$^1$ to R$^3$ are independently one of hydrogen, a substituted or unsubstituted C$_1$ to C$_{30}$ alkyl group, a substituted or unsubstituted C$_6$ to C$_{30}$ aryl group, a substituted or unsubstituted C$_3$ to C$_{30}$ heteroaryl group, a halogen, a cyano group (—CN), a cyano-containing group, and a combination thereof.

The compound for an organic photoelectric device may have 4 to 7 aromatic rings.

At least one of the Ar$^1$ and Ar$^2$ groups may be one of a substituted or unsubstituted naphthyl group, a substituted or unsubstituted anthracenyl group and a substituted or unsubstituted phenanthrenyl group.

In Chemical Formula 1, a cyclic group represented by Ar and bound to a methine group may be represented by Chemical Formula 2.

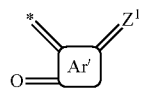

[Chemical Formula 2]

In Chemical Formula 2,

Ar' is one of a substituted or unsubstituted 5-membered aromatic ring, a substituted or unsubstituted 6-membered aromatic ring, and a condensed ring of two or more of the foregoing rings, and Z$^1$ is one of O and CR$^c$R$^d$, wherein R$^c$ and R$^d$ are independently one of hydrogen, a substituted or unsubstituted C$_1$ to C$_{10}$ alkyl group, a cyano group, and a cyano-containing group, provided at least one of R$^c$ and R$^d$ is one of a cyano group and a cyano-containing group.

In Chemical Formula 1, the cyclic group represented by Ar and bound to a methine group may be a cyclic group represented by one of Chemical Formulae 3-1 to 3-3.

[Chemical Formula 3-1]

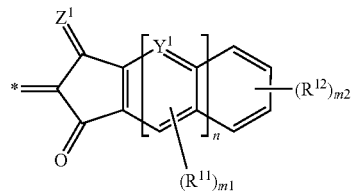

[Chemical Formula 3-2]

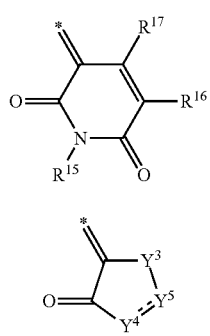

[Chemical Formula 3-3]

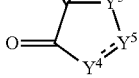

In Chemical Formulae 3-1 to 3-3, $Z^1$ is one of O and $CR^cR^d$ (wherein each of $R^c$ and $R^d$ are independently one of hydrogen, a substituted or unsubstituted $C_1$ to $C_{10}$ alkyl group, a cyano group, and a cyano-containing group, provided at least one of $R^c$ and $R^d$ is one of a cyano group and a cyano-containing group), $Y^1$ is one of N and $CR^e$ (wherein $R^e$ is one of hydrogen and a substituted or unsubstituted $C_1$ to $C_{10}$ alkyl group), $Y^3$ is one of O, S, Se, and Te, $Y^4$ is one of N and $NR^{18}$, $Y^5$ is one of $CR^{19}$ and $C=C(R^{20})(CN)$, each of $R^{11}$, $R^{12}$ and $R^{15}$ to $R^{20}$ are independently one of hydrogen, a substituted or unsubstituted $C_1$ to $C_{30}$ alkyl group, a substituted or unsubstituted $C_6$ to $C_{30}$ aryl group, a substituted or unsubstituted $C_4$ to $C_{30}$ heteroaryl group, a halogen, a cyano group (—CN), a cyano-containing group and a combination thereof, m1 is 0 or 1, m2 is an integer ranging from 0 to 4, and n is 0 or 1.

The compound for an organic photoelectric device may be represented by one of Chemical Formulae 4-1 to 4-3.

[Chemical Formula 4-1]

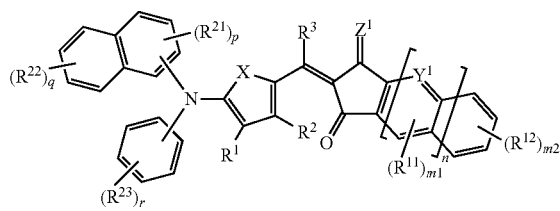

[Chemical Formula 4-2]

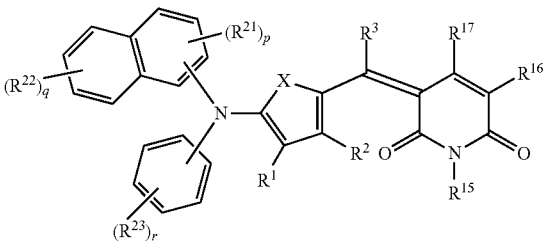

[Chemical Formula 4-3]

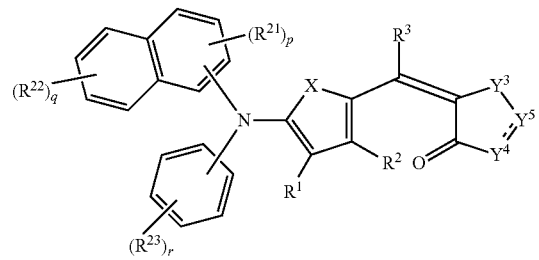

In Chemical Formulae 4-1 to 4-3,

X is one of Se, Te, S(=O), S(=O)$_2$, and $SiR^aR^b$ (wherein $R^a$ and $R^b$ are independently one of hydrogen and a substituted or unsubstituted $C_1$ to $C_{10}$ alkyl group), $Z^1$ is one of O and $CR^cR^d$ (wherein $R^c$ and $R^d$ are independently one of hydrogen, a substituted or unsubstituted $C_1$ to $C_{10}$ alkyl group, a cyano group, and a cyano-containing group, provided at least one of $R^c$ and $R^d$ is one of a cyano group and a cyano-containing group), $Y^1$ is one of N and $CR^e$ (wherein $R^e$ is one of hydrogen and a substituted or unsubstituted $C_1$ to $C_{10}$ alkyl group), $Y^3$ is one of O, S, Se, and Te, $Y^4$ is one of N and $NR^{18}$, $Y^5$ is one of $CR^{19}$ and $C=C(R^{20})(CN)$, each of $R^1$ to $R^3$, $R^{11}$, $R^{12}$ and $R^{15}$ to $R^{20}$ are independently one of hydrogen, a substituted or unsubstituted $C_1$ to $C_{30}$ alkyl group, a substituted or unsubstituted $C_6$ to $C_{30}$ aryl group, a substituted or unsubstituted $C_4$ to $C_{30}$ heteroaryl group, a halogen, a cyano group (—CN), a cyano-containing group and combination thereof, m1 is 0 or 1, m2 is an integer ranging from 0 to 4, n is 0 or 1, each of $R^{21}$ to $R^{23}$ are independently one of hydrogen, a halogen, a cyano group (—CN), a cyano-containing group, a substituted or unsubstituted $C_1$ to $C_6$ alkyl group, a substituted or unsubstituted $C_1$ to $C_6$ alkoxy group, and a combination thereof, p is an integer ranging from 0 to 3, q is an integer ranging from 0 to 4, and r is an integer ranging from 0 to 5.

The compound for an organic photoelectric device may have a maximum absorption wavelength ($\lambda_{max}$) in a wavelength region of about 500 nm to about 600 nm, for example, greater than about 530 nm and less than or equal to about 575 nm.

The compound for an organic photoelectric device may show a light absorption curve having a full width at half maximum (FWHM) of about 50 nm to about 110 nm in a thin film state.

The compound may have a thermal decomposition of greater than or equal to about 280° C.

According to example embodiments, an organic photoelectric device includes a first electrode and a second electrode facing each other, and an active layer between the first electrode and the second electrode and including the compound represented by Chemical Formula 1.

The compound for an organic photoelectric device may have 4 to 7 aromatic rings.

In Chemical Formula 1, at least one of the $Ar^1$ and $Ar^2$ groups may be one of a substituted or unsubstituted naphthyl group, a substituted or unsubstituted anthracenyl group and a substituted or unsubstituted phenanthrenyl group.

The compound for an organic photoelectric device may be represented by one of Chemical Formulae 4-1 to 4-3.

The compound may have a maximum absorption wavelength ($\lambda_{max}$) in a wavelength region of about 500 nm to about 600 nm, for example greater than about 530 nm and less than or equal to about 575 nm.

The compound for an organic photoelectric device may show a light absorption curve having a full width at half maximum (FWHM) of about 50 nm to about 110 nm in a thin film state.

The compound may have a thermal decomposition of greater than or equal to about 280° C.

According to example embodiments, an image sensor includes the organic photoelectric device.

The image sensor may include a semiconductor substrate integrated with a plurality of first photo-sensing devices configured to sense light in a blue wavelength region and a plurality of second photo-sensing devices configured to sense light in a red wavelength region, and the organic photoelectric device may be on the semiconductor substrate and configured to sense light in a green wavelength region.

The first photo-sensing devices and the second photo-sensing devices may be stacked in a vertical direction on the semiconductor substrate.

The image sensor may further include a color filter layer between the semiconductor substrate and the organic photoelectric device, the color filter layer including a blue filter configured to selectively transmit light in the blue wavelength region and a red filter configured to selectively transmit light in the red wavelength region.

The organic photoelectric device may be a green photoelectric device, and the green photoelectric device, a blue photoelectric device configured to sense light in a blue wavelength region, and a red photoelectric device configured to sense light in a red wavelength region may be stacked.

According to example embodiments, an electronic device includes the image sensor.

According to example embodiments, a compound for an organic photoelectric device is represented by Chemical Formula 1:

[Chemical Formula 1]

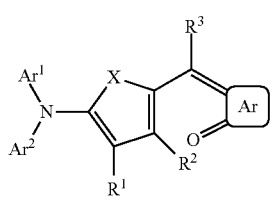

wherein, in Chemical Formula 1,
Ar is one of a substituted or unsubstituted 6-membered aromatic ring and a condensed ring of two or more of the foregoing ring, X is one of Se, S(=O), S(=O)$_2$, and SiR$^a$R$^b$ (wherein each of R$^a$ and R$^b$ are independently one of hydrogen and a substituted or unsubstituted C$_1$ to C$_{10}$ alkyl group), each of Ar$^1$ and Ar$^2$ are independently one of a substituted or unsubstituted C$_6$ to C$_{30}$ aryl group, provided at least one of Ar$^1$ and Ar$^2$ is one of a substituted or unsubstituted naphthyl group, and each of R$^1$ to R$^3$ are independently one of hydrogen, a substituted or unsubstituted C$_1$ to C$_{30}$ alkyl group, a substituted or unsubstituted C$_6$ to C$_{30}$ aryl group, a substituted or unsubstituted C$_3$ to C$_{30}$ heteroaryl group, a halogen, a cyano group (—CN), a cyano-containing group, and a combination thereof.

The compound for an organic photoelectric device may be represented by one of Chemical Formulae 4-1 and 4-2.

[Chemical Formula 4-1]

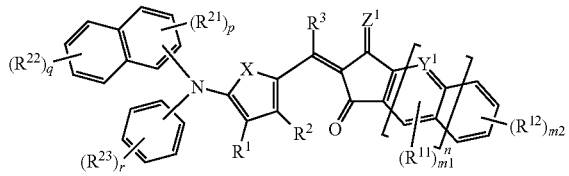

[Chemical Formula 4-2]

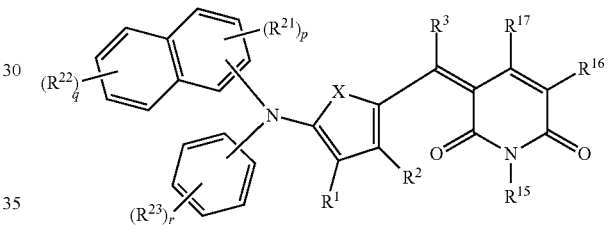

wherein, in Chemical Formulae 4-1 to 4-2,
X is one of Se, S(=O), S(=O)$_2$, and SiR$^a$R$^b$ (wherein each of R$^a$ and R$^b$ are independently one of hydrogen and a substituted or unsubstituted C$_1$ to C$_{10}$ alkyl group), $Z^1$ is one of O and CR$^c$R$^d$ (wherein R$^c$ and R$^d$ are independently one of hydrogen, a substituted or unsubstituted C$_1$ to C$_{10}$ alkyl group, a cyano group, and a cyano-containing group, provided at least one of R$^c$ and R$^d$ is one of a cyano group and a cyano-containing group), $Y^1$ is one of N and CR$^e$ (wherein R$^e$ is one of hydrogen and a substituted or unsubstituted C$_1$ to C$_{10}$ alkyl group), $Y^3$ is one of O, S, Se, and Te,
$Y^4$ is one of N and NR$^{18}$,
$Y^5$ is one of CR$^{19}$ and C=C(R$^{20}$)(CN),
each of R$^1$ to R$^3$, R$^{11}$, R$^{12}$ and R$^{15}$ to R$^{17}$ are independently one of hydrogen, a substituted or unsubstituted C$_1$ to C$_{30}$ alkyl group, a substituted or unsubstituted C$_6$ to C$_{30}$ aryl group, a substituted or unsubstituted C$_4$ to C$_{30}$ heteroaryl group, a halogen, a cyano group (—CN), a cyano-containing group and combination thereof, m1 is 0 or 1,
m2 is an integer ranging from 0 to 4,
n is 0 or 1,
each of R$^{21}$ to R$^{23}$ are independently one of hydrogen, a halogen, a cyano group (—CN), a cyano-containing group, a substituted or unsubstituted C$_1$ to C$_6$ alkyl group, a substituted or unsubstituted C$_1$ to C$_6$ alkoxy group, and a combination thereof, p is an integer ranging from 0 to 3, q is an integer ranging from 0 to 4, and r is an integer ranging from 0 to 5.

According to example embodiments, an organic photoelectric device includes a first electrode and a second electrode facing each other, and an active layer between the first electrode and the second electrode and including the aforementioned compound of example embodiments.

According to example embodiments, an image sensor includes the organic photoelectric device.

According to example embodiments, an electronic device includes the image sensor.

DETAILED DESCRIPTION

Figure 1:
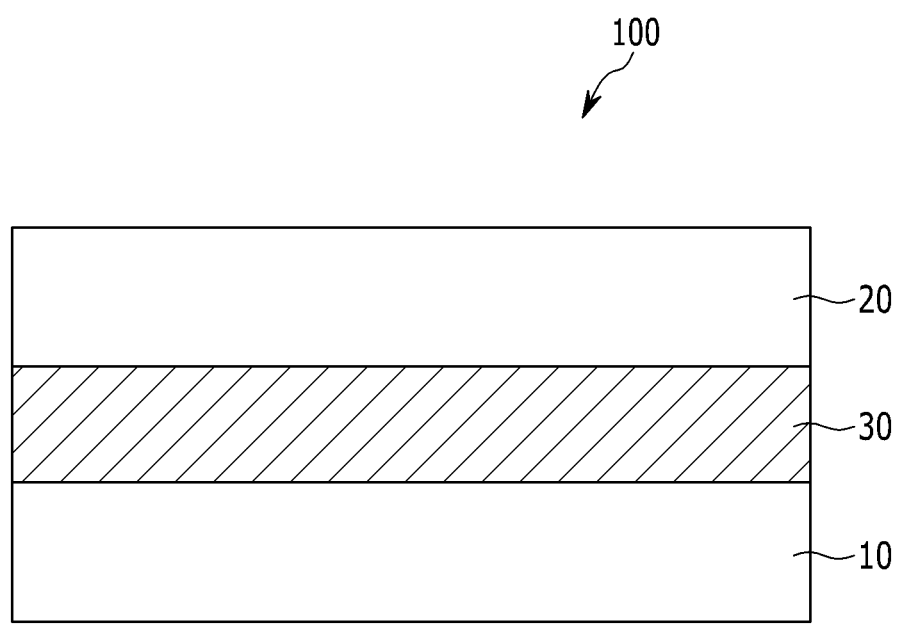
FIG. 1 is a cross-sectional view showing an organic photoelectric device according to example embodiments.

Example embodiments will hereinafter be described in detail, and may be more easily performed by those who have common knowledge in the related art. However, this disclosure may be embodied in many different forms and is not to be construed as limited to the example embodiments set forth herein.

In the drawings, the thickness of layers, films, panels, regions, etc., are exaggerated for clarity. Like reference numerals designate like elements throughout the specification. It will be understood that when an element such as a layer, film, region, or substrate is referred to as being "on" another element, it can be directly on the other element or intervening elements may also be present. In contrast, when an element is referred to as being "directly on" another element, there are no intervening elements present.

In the drawings, parts having no relationship with the description are omitted for clarity of the embodiments, and the same or similar constituent elements are indicated by the same reference numerals throughout the specification.

It should be understood that, although the terms first, second, third, etc. may be used herein to describe various elements, components, regions, layers and/or sections, these elements, components, regions, layers, and/or sections should not be limited by these terms. These terms are only used to distinguish one element, component, region, layer, or section from another region, layer, or section. Thus, a first element, component, region, layer, or section discussed below could be termed a second element, component, region, layer, or section without departing from the teachings of example embodiments.

Spatially relative terms (e.g., "beneath," "below," "lower," "above," "upper," and the like) may be used herein for ease of description to describe one element or feature's relationship to another element(s) or feature(s) as illustrated in the figures. It should be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the term "below" may encompass both an orientation of above and below. The device may be otherwise oriented (rotated 90 degrees or at other orientations) and the spatially relative descriptors used herein interpreted accordingly.

The terminology used herein is for the purpose of describing various embodiments only and is not intended to be limiting of example embodiments. As used herein, the singular forms "a," "an," and "the" are intended to include the plural forms as well, unless the context clearly indicates otherwise. It will be further understood that the terms "includes," "including," "comprises," and/or "comprising," when used in this specification, specify the presence of stated features, integers, steps, operations, elements, and/or components, but do not preclude the presence or addition of one or more other features, integers, steps, operations, elements, components, and/or groups thereof.

Example embodiments are described herein with reference to cross-sectional illustrations that are schematic illustrations of idealized embodiments (and intermediate structures) of example embodiments. As such, variations from the shapes of the illustrations as a result, for example, of manufacturing techniques and/or tolerances, are to be expected. Thus, example embodiments should not be construed as limited to the shapes of regions illustrated herein but are to include deviations in shapes that result, for example, from manufacturing.

Unless otherwise defined, all terms (including technical and scientific terms) used herein have the same meaning as commonly understood by one of ordinary skill in the art to which example embodiments belong. It will be further understood that terms, including those defined in commonly used dictionaries, should be interpreted as having a meaning that is consistent with their meaning in the context of the relevant art and will not be interpreted in an idealized or overly formal sense unless expressly so defined herein.

As used herein, when specific definition is not otherwise provided, the term "substituted" refers to one substituted with a substituent selected from a halogen (F, Br, Cl, or I), a hydroxy group, a nitro group, a cyano group, an amino group, an azido group, an amidino group, a hydrazino group, a hydrazono group, a carbonyl group, a carbamyl group, a thiol group, an ester group, a carboxyl group or a salt thereof, a sulfonic acid group or a salt thereof, phosphoric acid group or a salt thereof, a $C_1$ to $C_{20}$ alkyl group, a $C_1$ to $C_{20}$ alkoxy group, a $C_2$ to $C_{20}$ alkenyl group, a $C_2$ to $C_{20}$ alkynyl group, a $C_6$ to $C_{30}$ aryl group, a $C_7$ to $C_{30}$ arylalkyl group, a $C_1$ to $C_{20}$ heteroalkyl group, a $C_1$ to $C_{20}$ heteroaryl group, a $C_3$ to $C_{20}$ heteroarylalkyl group, a $C_3$ to $C_{30}$ cycloalkyl group, a $C_3$ to $C_{15}$ cycloalkenyl group, a $C_6$ to $C_{15}$ cycloalkynyl group, a $C_2$ to $C_{20}$ heterocycloalkyl group, and a combination thereof, instead of hydrogen of a compound or a group.

As used herein, when specific definition is not otherwise provided, the term "hetero" refers to one including 1 to 3 heteroatoms selected from N, O, S, P, and Si.

As used herein, the term "alkyl group" for example refers to a methyl group, an ethyl group, a propyl group, an isopropyl group, a n-butyl group, an isobutyl group, a t-butyl group, a pentyl group, a hexyl group, etc.

As used herein, the term "cycloalkyl group" for example refers to a cyclopropyl group, a cyclobutyl group, a cyclopentyl group, a cyclohexyl group, etc.

As used herein, the term "aryl group" refers to a cyclic substituent where all elements have p-orbitals, and these p-orbitals forms conjugation, and includes a monocyclic, polycyclic or fused ring polycyclic (i.e., rings sharing adjacent pairs of carbon atoms) functional group.

As used herein, when specific definition is not otherwise provided, the term "cyano-containing group" refers to a $C_1$ to $C_{30}$ alkyl group, a $C_2$ to $C_{30}$ alkenyl group, or a $C_2$ to $C_{30}$ alkynyl group where at least one hydrogen is replaced by a cyano group. In addition, the cyano-containing group may include a dicyanoalkenyl group represented by $=CR^{x'}-(CR^xR^y)_p-CR^{y'}(CN)_2$ wherein $R^x$, $R^y$, $R^{x'}$, and $R^{y'}$ are independently one of hydrogen or a $C_1$ to $C_{10}$ alkyl group and p is an integer ranging from 0 to 10. Specific examples of the cyano-containing group may be a dicyanomethyl group, a dicyanovinyl group, a cyanoethynyl group.

As used herein, when a definition is not otherwise provided, the term "combination thereof" refers to at least two substituents bound to each other by a single bond or a $C_1$ to $C_{10}$ alkylene group, or at least two fused substituents.

As used herein, the term "5-membered aromatic ring" refers to a 5-membered cyclic group or a 5-membered heterocyclic group that provides a conjugated ring structure. The term "6-membered aromatic ring" refers to a 6-membered cyclic group or a 6-membered heterocyclic group that provides a conjugated ring structure.

Hereinafter, a compound for an organic photoelectric device according to example embodiments is described.

A compound for an organic photoelectric device according to example embodiments is represented by Chemical Formula 1.

[Chemical Formula 1]

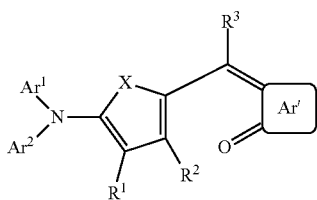

In Chemical Formula 1,

Ar is one of a substituted or unsubstituted 5-membered aromatic ring, a substituted or unsubstituted 6-membered aromatic ring, and a condensed ring of two or more of the foregoing rings, X is one of Se, Te, S(=O), S(=O)$_2$, and SiR$^a$R$^b$ (wherein each of R$^a$ and R$^b$ are independently one of hydrogen and a substituted or unsubstituted $C_1$ to $C_{10}$ alkyl group), each of Ar$^1$ and Ar$^2$ are independently one of a substituted or unsubstituted $C_6$ to $C_{30}$ aryl group and a substituted or unsubstituted $C_3$ to $C_{30}$ heteroaryl group, and each of R$^1$ to R$^3$ are independently one of hydrogen, a substituted or unsubstituted $C_1$ to $C_{30}$ alkyl group, a substituted or unsubstituted $C_6$ to $C_{30}$ aryl group, a substituted or unsubstituted $C_3$ to $C_{30}$ heteroaryl group, a halogen, a cyano group (—CN), a cyano-containing group, and a combination thereof.

In the Ar$^1$, Ar$^2$, Ar, and R$^1$ to R$^3$, the term "substituted" refers to one substituted with, for example a halogen (F, Cl, Br, or I), a cyano group (—CN), a $C_1$ to $C_6$ alkyl group, or a $C_1$ to $C_6$ alkoxy group, but is not limited thereto. In example embodiments, the halogen may be a chloro group (—Cl) or a fluoro group (—F).

In Chemical Formula 1, each of R$^1$ to R$^3$ may independently be one of, for example hydrogen, a substituted or unsubstituted $C_1$ to $C_{10}$ alkyl group, a substituted or unsubstituted $C_6$ to C12 aryl group, a substituted or unsubstituted $C_3$ to $C_{10}$ heteroaryl group, a halogen, a cyano group (—CN), and a combination thereof.

The compound for an organic photoelectric device may have 4 to 7 aromatic rings, for example 5 to 7 aromatic rings. When the number of the aromatic rings is 4 to 7, selective absorption in a green wavelength region may be improved. Herein the term "aromatic ring" refers to a substituted or unsubstituted 5-membered or 6-membered ring structure that provides a conjugation structure.

Each of Ar$^1$ and Ar$^2$ may independently be a substituted or unsubstituted $C_6$ to $C_{30}$ aryl group or a substituted or unsubstituted $C_3$ to $C_{30}$ heteroaryl group where aromatic rings are present singularly or fused to each other, and may be for example, a substituted or unsubstituted $C_6$ to $C_{20}$ aryl group, for example a substituted or unsubstituted $C_8$ to $C_{20}$ aryl group, or a substituted or unsubstituted $C_3$ to $C_{20}$ heteroaryl group. That is, when a single bond or other linking groups are present between the aromatic rings to link the aromatic rings group, a conjugation structure may be broken and a desirable conjugation length is not provided.

Ar$^1$ and Ar$^2$ may be for example a substituted or unsubstituted phenyl group, a substituted or unsubstituted naphthyl group, a substituted or unsubstituted anthracenyl group, a substituted or unsubstituted phenanthrenyl group, a substituted or unsubstituted thienyl group, or a substituted or unsubstituted benzothienyl group. In example embodiments, the substituted phenyl group, the substituted naphthyl group, the substituted anthracenyl group, the substituted thienyl group or the substituted benzothienyl group may be substituted with a cyano group or a halogen.

At least one of Ar$^1$ and Ar$^2$ may be one of a substituted or unsubstituted $C_{10}$ to $C_{30}$ aryl group including a fused ring and a substituted or unsubstituted $C_5$ to $C_{30}$ heteroaryl group including a fused ring, and may be, for example one of a substituted or unsubstituted naphthyl group, a substituted or unsubstituted anthracenyl group, and a substituted or unsubstituted phenanthrenyl group. When at least one of Ar$^1$ and Ar$^2$ is a substituted or unsubstituted naphthyl group, a substituted or unsubstituted anthracenyl group, or a substituted or unsubstituted phenanthrenyl group, intermolecular interactions may be decreased, and thus aggregation among molecules in a film state is prevented or inhibited. In example embodiments, absorption selectivity in a green wavelength region may be further improved. When the Ar$^1$ and Ar$^2$ are an alkyl group or are linked to each other to provide an N-containing aliphatic cyclic group, instead of the aromatic group, the compound structure has planarity and thus a full width at half maximum (FWHM) of a light absorption curve may become undesirably wide which indicates reduction of absorption selectivity in a green wavelength region.

For example, $Ar^1$ and $Ar^2$ may be the same or different.

For example, one of $Ar^1$ and $Ar^2$ may be a substituted or unsubstituted phenyl group, and the other may be a substituted or unsubstituted $C_{10}$ to $C_{30}$ aryl group including a fused ring or a substituted or unsubstituted $C_5$ to $C_{30}$ heteroaryl group including a fused ring.

For example, one of $Ar^1$ and $Ar^2$ may be a substituted or unsubstituted phenyl group, and the other may be one of a substituted or unsubstituted naphthyl group, a substituted or unsubstituted anthracenyl group, and a substituted or unsubstituted phenanthrenyl group.

The compound represented by Chemical Formula 1 includes an electron donor moiety of arylamine and an electron acceptor moiety represented by Ar.

In Chemical Formula 1, a cyclic group represented by Ar and bound to a methine group is an electron acceptor moiety and includes at least one carbonyl group.

For example, in Chemical Formula 1, the cyclic group represented by Ar and bound to a methine group may include one or two carbonyl groups.

For example, in Chemical Formula 1, the cyclic group represented by Ar and bound to a methine group may include at least one carbonyl group and at least one cyano-containing moiety.

In Chemical Formula 1, a cyclic group represented by Ar and bound to a methine group may be, for example represented by Chemical Formula 2.

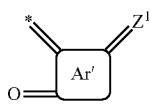

[Chemical Formula 2]

In Chemical Formula 2, Ar' is one of a substituted or unsubstituted 5-membered aromatic ring, a substituted or unsubstituted 6-membered aromatic ring, and a condensed ring of two or more of the foregoing rings, and $Z^1$ is one of O and $CR^cR^d$, wherein each of $R^c$ and $R^d$ are independently one of hydrogen, a substituted or unsubstituted $C_1$ to $C_{10}$ alkyl group, a cyano group, and a cyano-containing group, provided at least one of $R^c$ and $R^d$ is one of a cyano group and a cyano-containing group.

For example, in Chemical Formula 1, the cyclic group represented by Ar and bound to a methine group may be a condensed ring of a substituted or unsubstituted 5-membered aromatic ring and a substituted or unsubstituted 6-membered aromatic ring.

In Chemical Formula 1, the cyclic group represented by Ar and bound to a methine group may be, for example a cyclic group represented by one of Chemical Formulae 3-1 to 3-3.

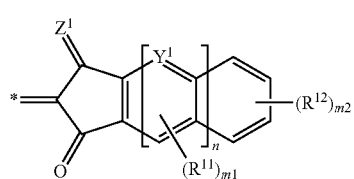

[Chemical Formula 3-1]

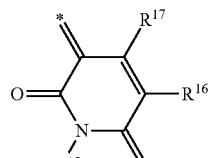

[Chemical Formula 3-2]

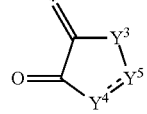

[Chemical Formula 3-3]

In Chemical Formulae 3-1 to 3-3, $Z^1$ is one of O and $CR^cR^d$ (wherein each of $R^c$ and $R^d$ are independently one of hydrogen, a substituted or unsubstituted $C_1$ to $C_{10}$ alkyl group, a cyano group, and a cyano-containing group, provided at least one of $R^c$ and $R^d$ is one of a cyano group and a cyano-containing group), $Y^1$ is one of N and $CR^a$ (wherein $R^a$ is one of hydrogen and a substituted or unsubstituted $C_1$ to $C_{10}$ alkyl group), $Y^3$ is one of O, S, Se, and Te, $Y^4$ is one of N and $NR^{18}$, $Y^5$ is one of $CR^{19}$ and $C=C(R^{20})(CN)$, each of $R^{11}$, $R^{12}$ and $R^{15}$ to $R^{20}$ are independently one of hydrogen, a substituted or unsubstituted $C_1$ to $C_{30}$ alkyl group, a substituted or unsubstituted $C_6$ to $C_{30}$ aryl group, a substituted or unsubstituted $C_4$ to $C_{30}$ heteroaryl group, a halogen, a cyano group (—CN), a cyano-containing group and a combination thereof, m1 is 0 or 1, m2 is an integer ranging from 0 to 4, and n is 0 or 1.

The cyclic group represented by Chemical Formula 3-1 may be, for example a cyclic group represented Chemical Formula 3-1-1 or 3-1-2.

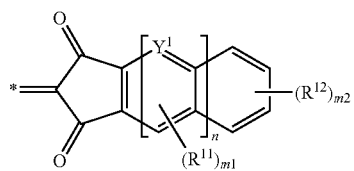

[Chemical Formula 3-1-1]

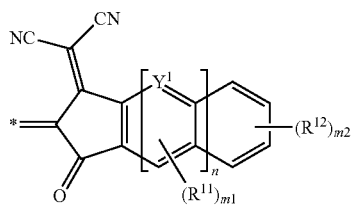

[Chemical Formula 3-1-2]

In Chemical Formula 3-1-1 and Chemical Formula 3-1-2, $Y^1$, $R^{11}$, $R^{12}$, n, m1 and m2 are the same as described above.

The cyclic group represented by Chemical Formula 3-2 may be, for example a cyclic group represented Chemical Formula 3-2-1 or 3-2-2.

[Chemical Formula 3-2-1]

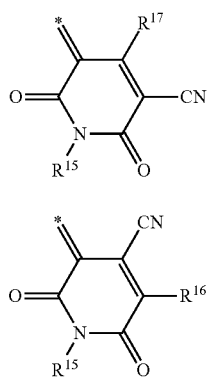

[Chemical Formula 3-2-2]

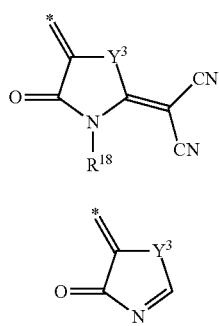

In Chemical Formulae 3-2-1 and 3-2-2, $R^{15}$ to $R^{17}$ are the same as described above.

The cyclic group represented by Chemical Formula 3-3 may be, for example a cyclic group represented Chemical Formula 3-3-1 or 3-3-2.

[Chemical Formula 3-3-1]

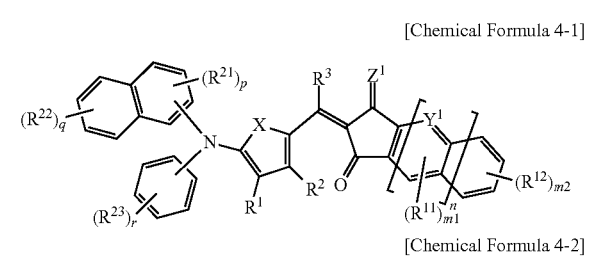

[Chemical Formula 3-3-2]

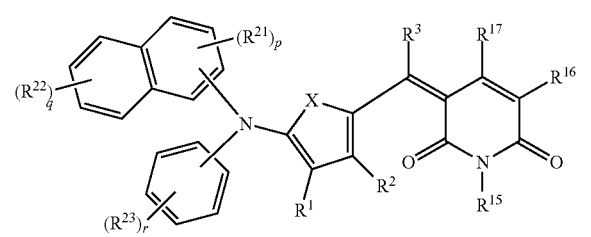

In Chemical Formulae 3-3-1 and 3-3-2, $Y^3$ and $R^{18}$ are the same as described above.

The compound for an organic photoelectric device may be, for example represented by one of Chemical Formulae 4-1 to 4-3.

[Chemical Formula 4-1]

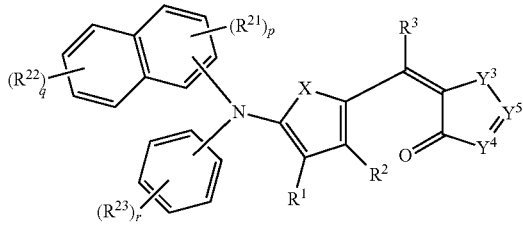

[Chemical Formula 4-2]

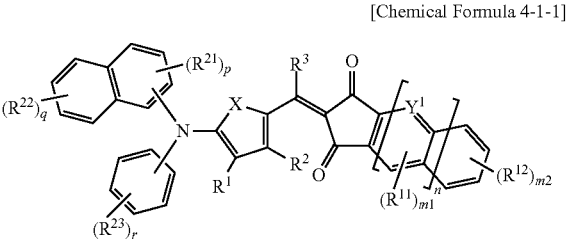

[Chemical Formula 4-3]

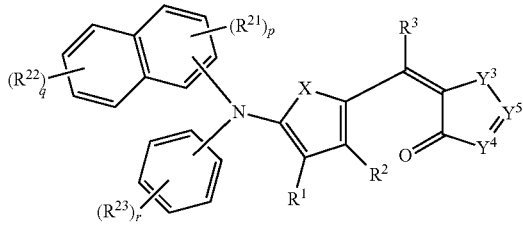

In Chemical Formulae 4-1 to 4-3,

X is one of Se, Te, S(=O), S(=O)$_2$, and SiR$^a$R$^b$ (wherein R$^a$ and R$^b$ are independently one of hydrogen and a substituted or unsubstituted C$_1$ to C$_{10}$ alkyl group), Z$^1$ is one of O and CR$^c$R$^d$ (wherein each of R$^c$ and R$^d$ are independently one of hydrogen, a substituted or unsubstituted C$_1$ to C$_{10}$ alkyl group, a cyano group, and a cyano-containing group, provided at least one of R$^c$ and R$^d$ is one of a cyano group and a cyano-containing group), Y$^1$ is one of N and CR$^e$ (wherein R$^e$ is one of hydrogen and a substituted or unsubstituted C$_1$ to C$_{10}$ alkyl group), Y$^3$ is one of O, S, Se, and Te, Y$^4$ is one of N and NR$^{18}$, Y$^5$ is one of CR$^{19}$ and C=C(R$^{20}$)(CN), each of R$^1$ to R$^3$, R$^{11}$, R$^{12}$ and R$^{15}$ to R$^{20}$ are independently one of hydrogen, a substituted or unsubstituted C$_1$ to C$_{30}$ alkyl group, a substituted or unsubstituted C$_6$ to C$_{30}$ aryl group, a substituted or unsubstituted C$_4$ to C$_{30}$ heteroaryl group, a halogen, a cyano group (—CN), a cyano-containing group and combination thereof, m1 is 0 or 1, m2 is an integer ranging from 0 to 4, n is 0 or 1, each of R$^{21}$ to R$^{23}$ are independently one of hydrogen, a halogen, a cyano group (—CN), a cyano-containing group, a substituted or unsubstituted C$_1$ to C$_6$ alkyl group, a substituted or unsubstituted C$_1$ to C$_6$ alkoxy group, and a combination thereof, p is an integer ranging from 0 to 3, q is an integer ranging from 0 to 4, and r is an integer ranging from 0 to 5.

The compound for an organic photoelectric device represented by Chemical Formula 4-1 may be, for example a compound for an organic photoelectric device represented by Chemical Formula 4-1-1 or 4-1-2.

[Chemical Formula 4-1-1]

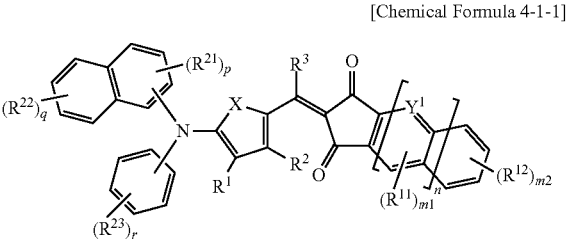

[Chemical Formula 4-1-2]

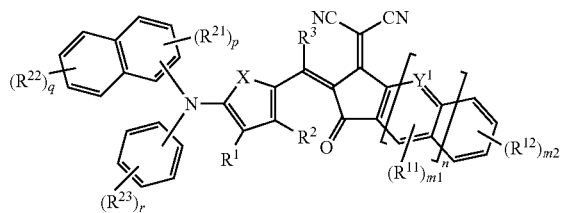

[Chemical Formula 4-3-2]

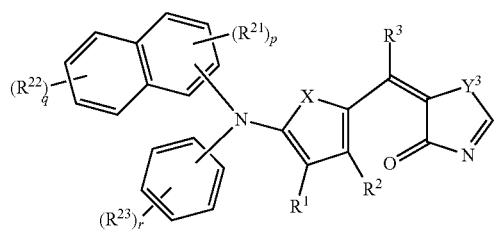

In Chemical Formulae 4-1-1 and 4-1-2, X, $Y^1$, $R^1$ to $R^3$, $R^{11}$, $R^{12}$, $R^{21}$ to $R^{23}$, n, m1, m2, p, q and r are the same as described above.

The compound for an organic photoelectric device represented by Chemical Formula 4-2 may be, for example a compound for an organic photoelectric device represented by Chemical Formula 4-2-1 or 4-2-2.

In Chemical Formulae 4-3-1 and 4-3-2, X, $Y^3$, $R^1$ to $R^3$, $R^{18}$, $R^{21}$ to $R^{23}$, p, q and r are the same as described above.

Examples of the compound represented by Chemical Formula 1 may be a compound of Chemical Formula 5-1, Chemical Formula 5-2, Chemical Formula 5-3, Chemical Formula 5-4 and Chemical Formula 5-5, but are not limited thereto.

[Chemical Formula 4-2-1]

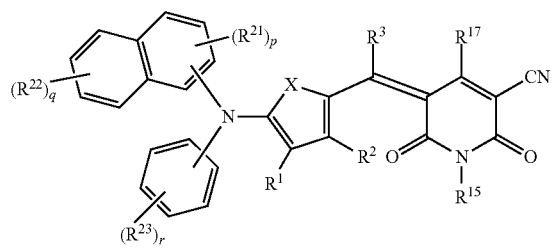

[Chemical Formula 5-1]

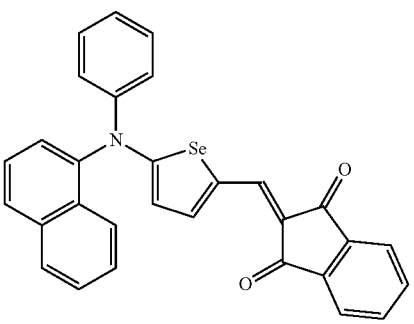

[Chemical Formula 4-2-2]

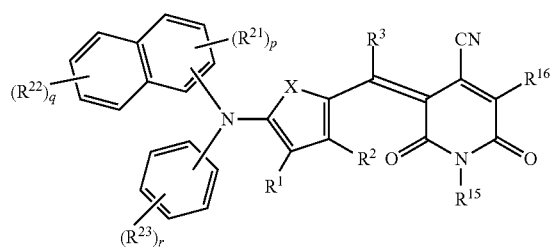

In Chemical Formulae 4-2-1 and 4-2-2, X, $R^1$ to $R^3$, $R^{15}$ to $R^{17}$, $R^{21}$ to $R^{23}$, p, q and r are the same as described above.

The compound for an organic photoelectric device represented by Chemical Formula 4-3 may be, for example a compound for an organic photoelectric device represented by Chemical Formula 4-3-1 or 4-3-2.

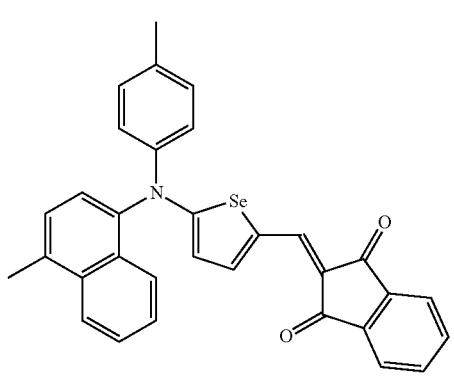

[Chemical Formula 4-3-1]

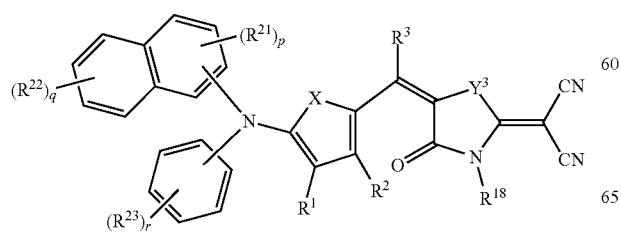

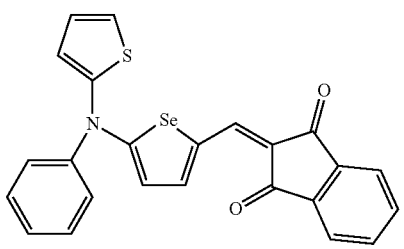

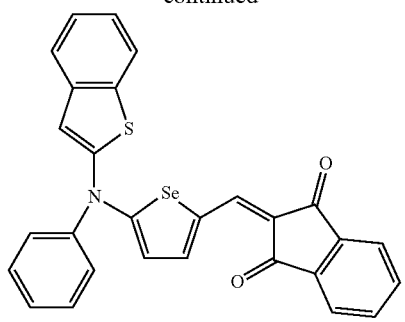
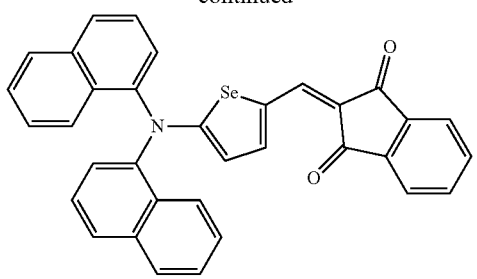
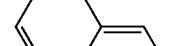

-continued
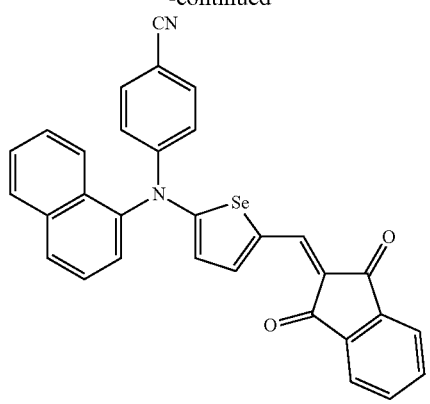
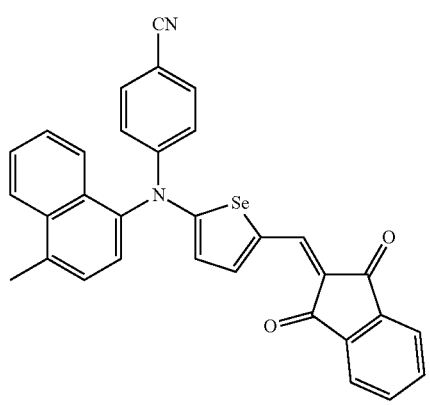
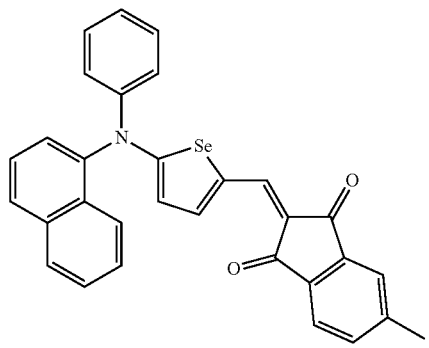
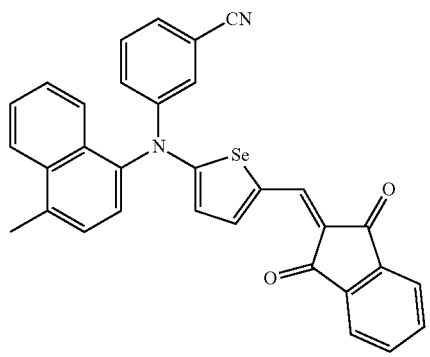
-continued
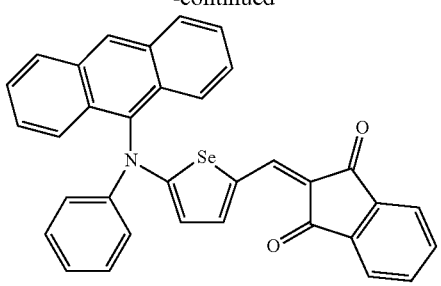
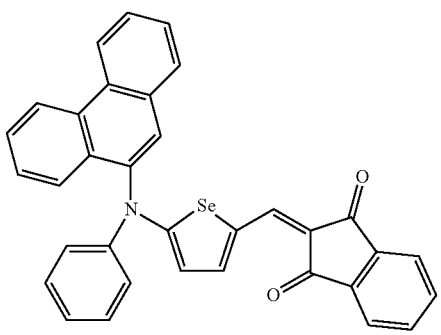
[Chemical Formula 5-2]
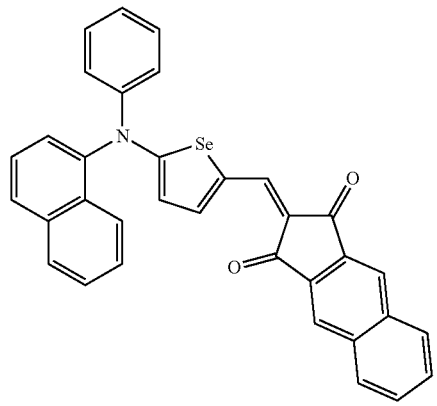
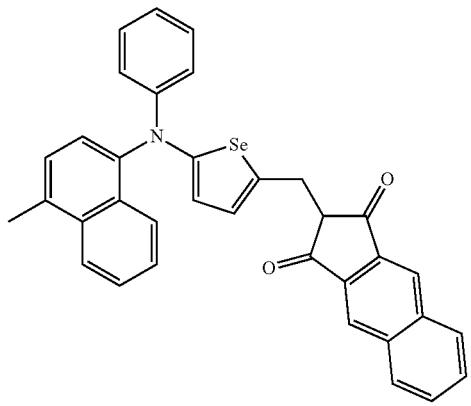

-continued
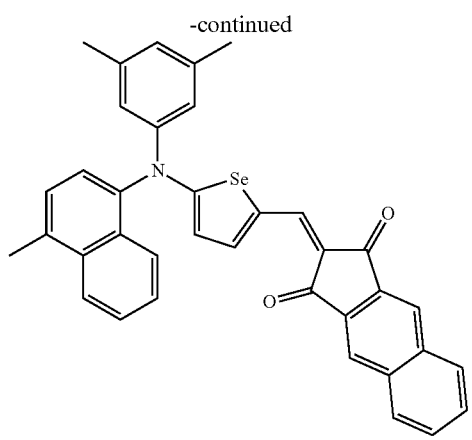
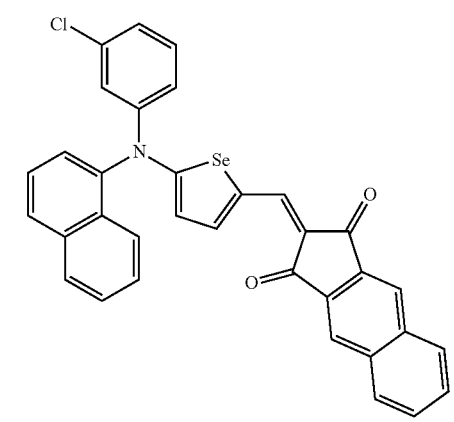
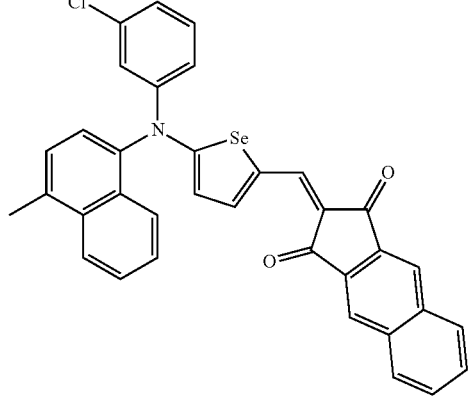
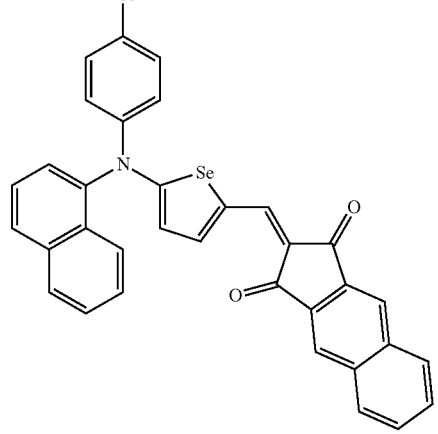
-continued
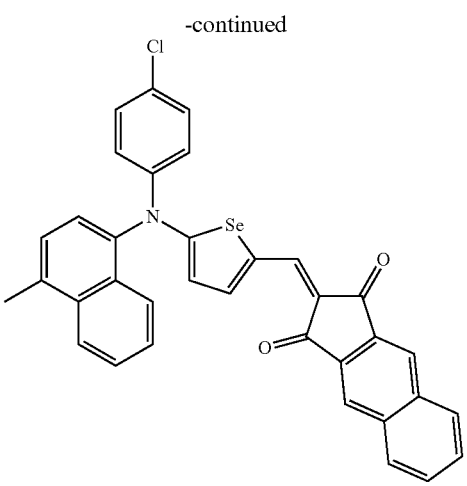
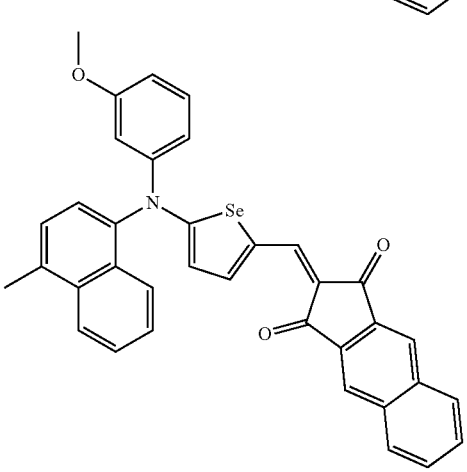
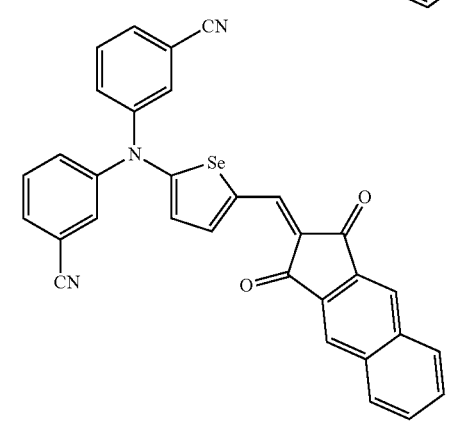
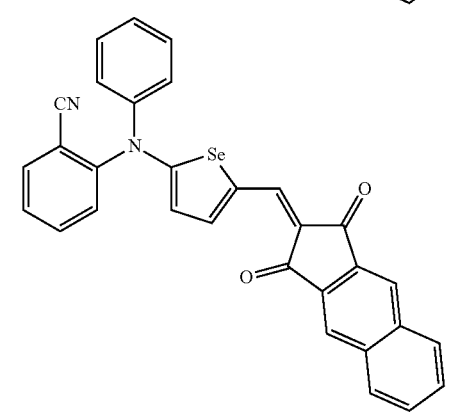

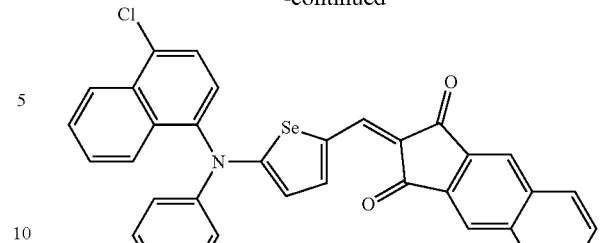
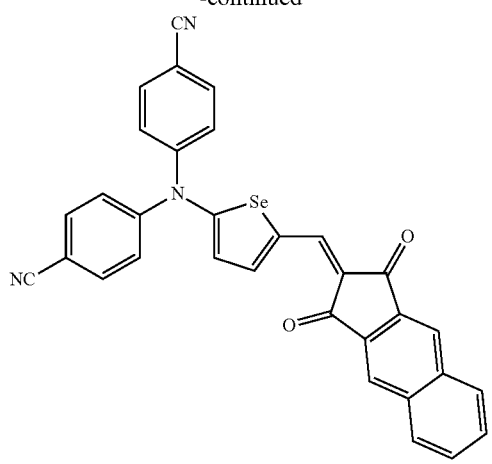
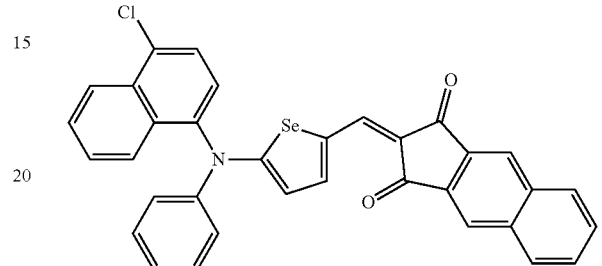
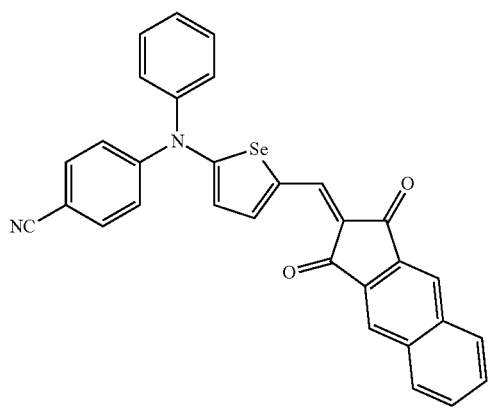
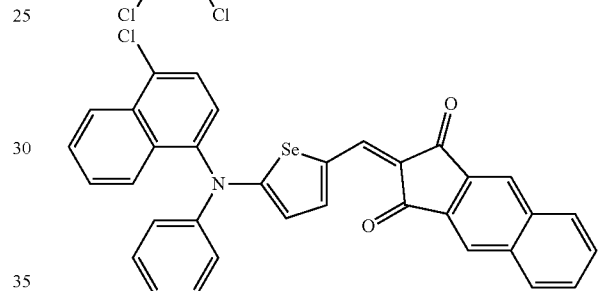
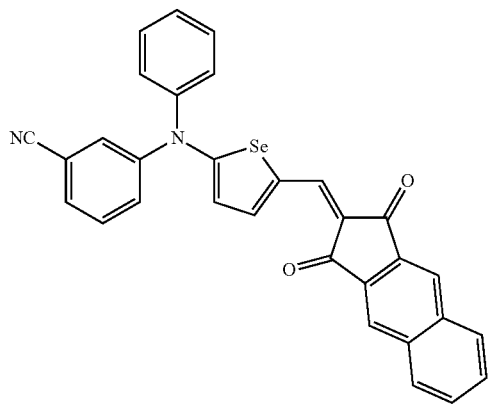
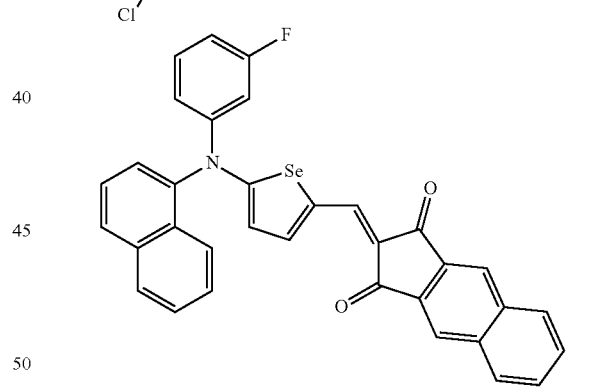
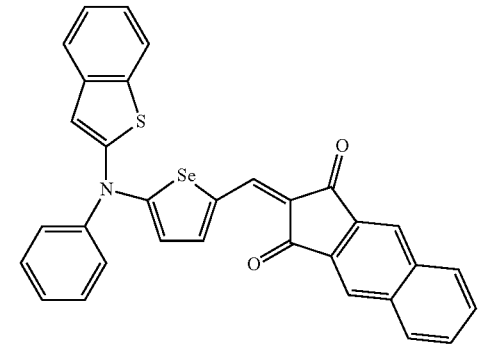
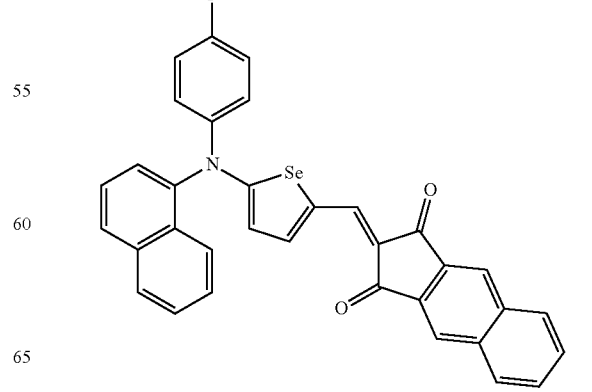

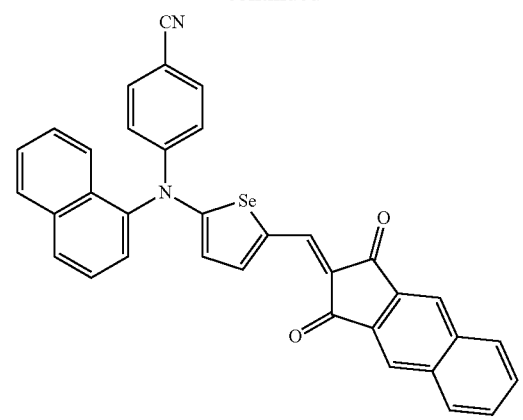
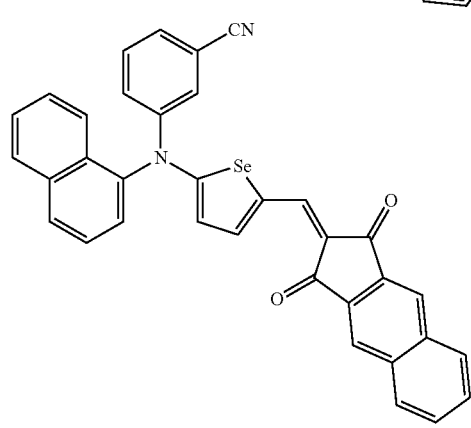
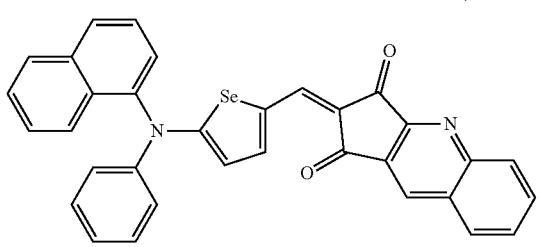
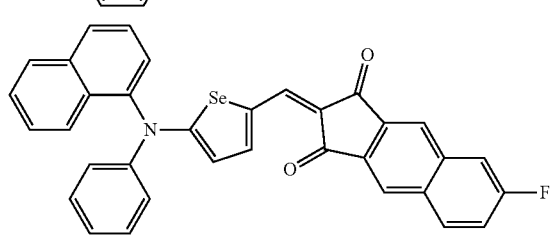
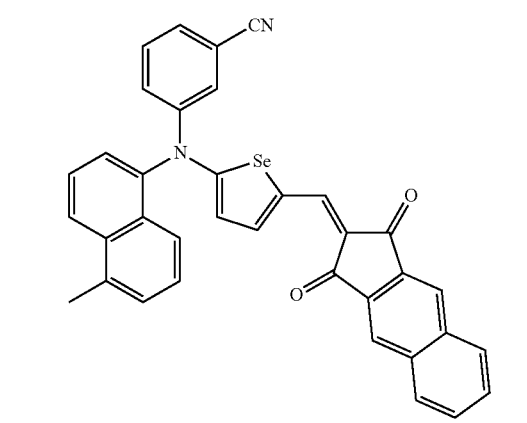
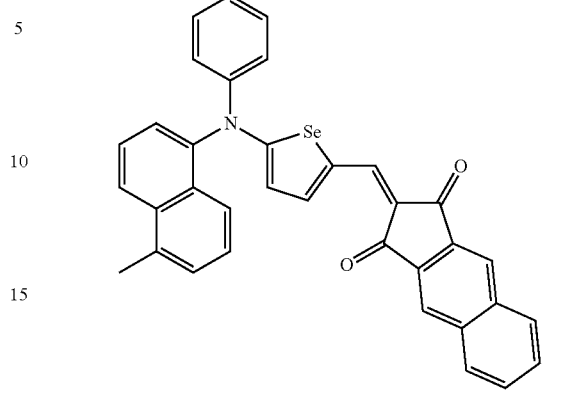
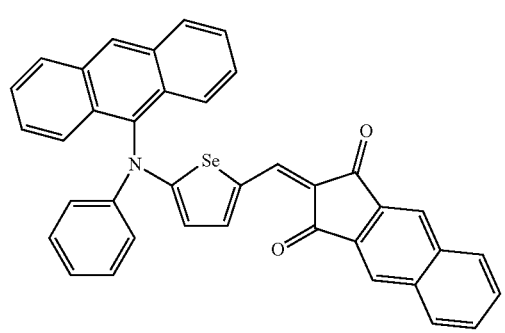
[Chemical Formula 5-3]
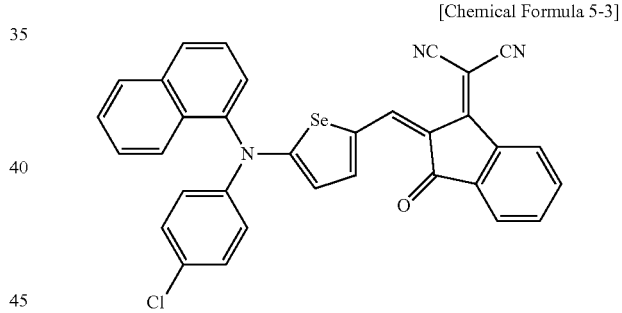
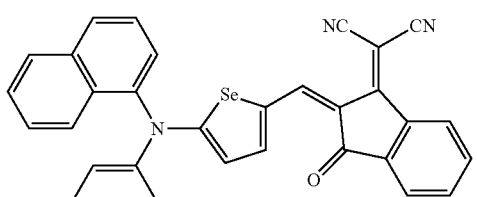
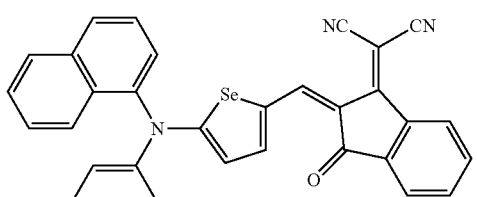
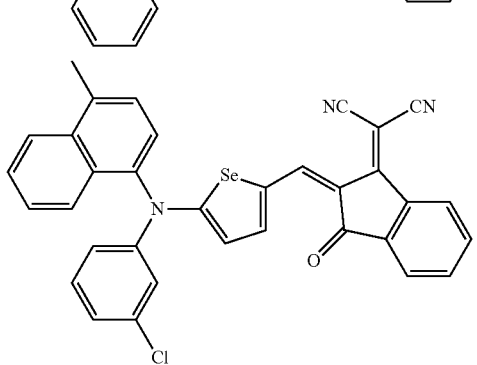

[Chemical Formula 5-4]
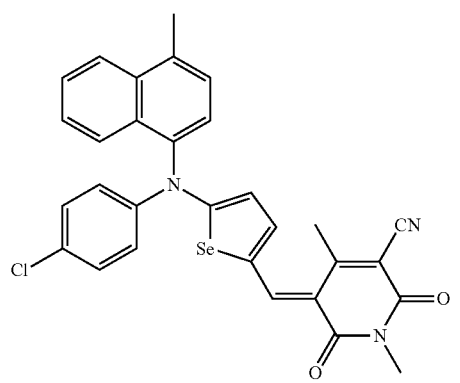
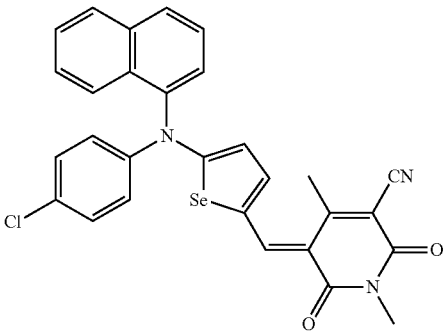

-continued

[Chemical Formula 5-5]

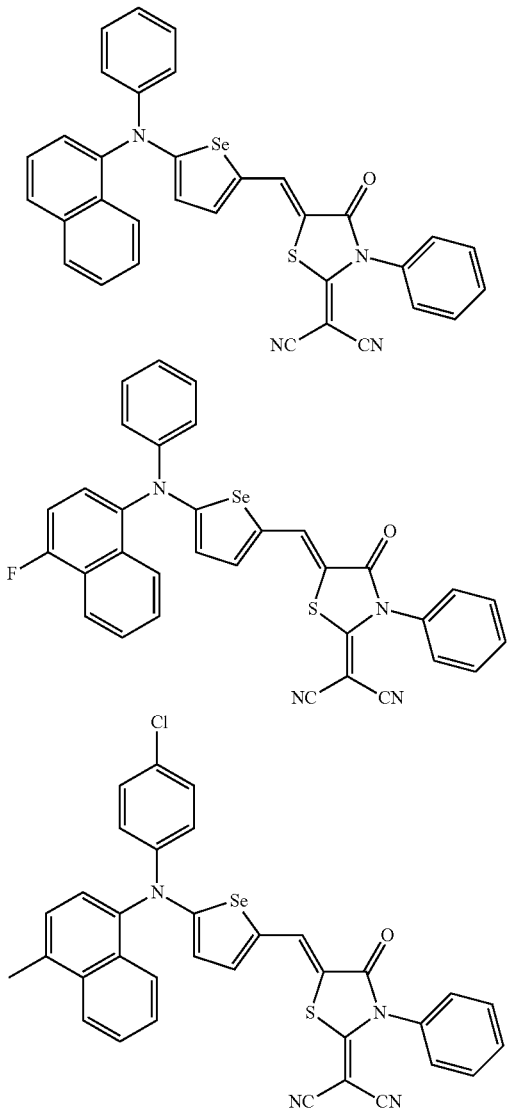

The semiconductor compound is a compound selectively absorbing light in a green wavelength region, and may have a maximum absorption wavelength ($\lambda_{max}$) in a wavelength region of greater than or equal to about 500 nm and less than or equal to about 600 nm, for example greater than or equal to about 530 nm and less than or equal to about 600 nm, greater than about 530 nm and less than or equal to about 575 nm, greater than or equal to about 532 nm and less than or equal to about 572 nm, greater than or equal to about 535 nm and less than or equal to about 570 nm, or greater than or equal to about 540 nm and less than or equal to about 560 nm.

The compound for an organic photoelectric device may show a light absorption curve having a full width at half maximum (FWHM) of about 50 nm to about 110 nm, for example about 50 nm to about 100 nm or about 50 nm to about 90 nm, in a thin film state. Herein, the FWHM is a width of a wavelength corresponding to half of a maximum absorption point. As used herein, when specific definition is not otherwise provided, it may be defined by absorbance measured by UV-Vis spectroscopy. When the full width at half maximum (FWHM) is within the range, selectivity in a green wavelength region may be increased. The thin film may be a thin film deposited under a vacuum condition.

The compound for an organic photoelectric device may have thermal decomposition temperature ($T_d$) of greater than or equal to about 280° C. The compound for an organic photoelectric device may have, for example a thermal decomposition temperature ($T_d$) of about 280° C. to about 500° C., for example about 285° C. to about 450° C. The thermal decomposition temperature ($T_d$) is a temperature at which a compound starts to be decomposed and thus, while not maintaining its intrinsic molecular structure, is transformed. In general, atoms in a molecule consisting of a compound are volatilized and lost into the air or vacuum at greater than or equal to a thermal decomposition temperature, and thus, the thermal decomposition temperature may be regarded as a temperature at which the initial weight of the compound starts to be decreased by heat.

The compound for an organic photoelectric device may have a HOMO level about 5.0 to about 5.5 eV, and an energy bandgap of about 1.7 to about 2.3 eV. The compound for an organic photoelectric device having a HOMO level and an energy bandgap within the ranges may be used as a p-type semiconductor compound effectively absorbing light in a green wavelength region, and thus has high external quantum efficiency (EQE) and resultantly improves photoelectric conversion efficiency.

The compound for an organic photoelectric device may have a molecular weight of about 300 to about 1500, for example, about 350 to about 1200, or about 400 to about 900. When the compound has a molecular weight within the range, the crystallinity of the compound and thermal decomposition during formation of a thin film by deposition may be inhibited.

The compound for an organic photoelectric device may have a melting point of greater than or equal to about 200° C., for example, greater than or equal to about 250° C., or greater than or equal to about 280° C. When the compound has a melting point within the range, a thin film may be stably deposited and the amount of a decomposed product is decreased, and thus an organic photoelectric device having desirable photoelectric conversion performance is provided.

The compound for an organic photoelectric device may be a p-type semiconductor compound.

Hereinafter, an organic photoelectric device including the compound according to example embodiments is described with reference to drawings.

FIG. 1 is a cross-sectional view showing an organic photoelectric device according to example embodiments.

Referring to FIG. 1, an organic photoelectric device 100 according to example embodiments includes a first electrode 10 and a second electrode 20, and an active layer 30 between the first electrode 10 and the second electrode 20.

One of the first electrode 10 and the second electrode 20 is an anode and the other is a cathode. At least one of the first electrode 10 and the second electrode 20 may be a light-transmitting electrode, and the light-transmitting electrode may be made of, for example, a transparent conductor such as indium tin oxide (ITO) or indium zinc oxide (IZO), or a metal thin layer of a thin monolayer or multilayer. When one of the first electrode 10 and the second electrode 20 is a non-light-transmitting electrode, the one of the first electrode 10 and the second electrode 20 may be made of, for example, an opaque conductor such as aluminum (Al).

The active layer 30 includes a p-type semiconductor and an n-type semiconductor to form a pn junction, and absorbs external light to generate excitons and then separates the generated excitons into holes and electrons.

The active layer 30 includes the compound represented by Chemical Formula 1. The compound for an organic photoelectric device may act as a p-type semiconductor compound in the active layer 30.

The compound for an organic photoelectric device is a compound that selectively absorbs light in a green wavelength region, and the active layer 30 including the compound may have a maximum absorption wavelength ($\lambda_{max}$) in a wavelength region of greater than or equal to about 500 nm and less than or equal to about 600 nm, for example greater than about 530 nm and less than or equal to about 575 nm, greater than or equal to about 532 nm and less than or equal to about 572 nm, greater than or equal to about 535 nm and less than or equal to about 570 nm, or greater than or equal to about 540 nm and less than or equal to about 560 nm.

The active layer 30 may show a light absorption curve having a relatively narrow full width at half maximum (FWHM) of about 50 nm to about 110 nm, for example about 50 nm to about 100 nm or about 50 nm to about 90 nm, in a thin film state. Accordingly, the active layer 30 has relatively high selectivity for light in a green wavelength region.

The active layer 30 may further include an n-type semiconductor compound for forming a pn junction.

The n-type semiconductor compound may be subphthalocyanine, a subphthalocyanine derivative, fullerene or a fullerene derivative, thiophene or a thiophene derivative, or a combination thereof.

The fullerene may include fullerene C60, fullerene C70, fullerene C76, fullerene C78, fullerene C80, fullerene C82, fullerene C84, fullerene C90, fullerene C96, fullerene C240, fullerene C540, mixed fullerene, fullerene nanotube, etc. The "fullerene derivatives" may refer to compounds of these fullerenes having a substituent attached thereto. The fullerene derivatives may include substituents such as alkyl groups, aryl groups, or heterocyclic groups. Examples of the aryl groups and heterocyclic groups may be are a benzene ring, a naphthalene ring, an anthracene ring, a phenanthrene ring, a fluorene ring, a triphenylene ring, a naphthacene ring, a biphenyl ring, a pyrrole ring, a furan ring, a thiophene ring, an imidazole ring, an oxazole ring, a thiazole ring, a pyridine ring, a pyrazine ring, a pyrimidine ring, a pyridazine ring, an indolizine ring, an indole ring, a benzofuran ring, a benzothiophene ring, an isobenzofuran ring, a benzimidazole ring, an imidazopyridine ring, a quinolizidine ring, a quinoline ring, a phthalazine ring, a naphthyridine ring, a quinoxaline ring, a quinoxazoline ring, an isoquinoline ring, a carbazole ring, a phenanthridine ring, an acridine ring, a phenanthroline ring, a thianthrene ring, a chromene ring, an xanthene ring, a phenoxathin ring, a phenothiazine ring, or a phenazine ring.

The subphthalocyanine or subphthalocyanine derivative may be represented by Chemical Formula 6.

[Chemical Formula 6]

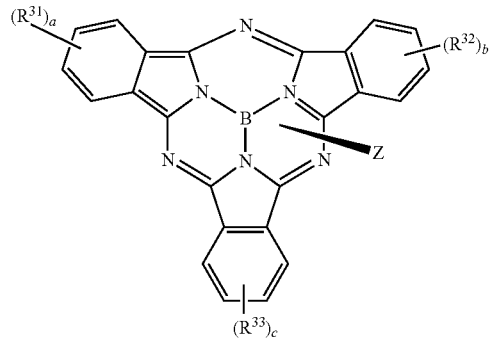

In Chemical Formula 6,
each of $R^{31}$ to $R^{33}$ are independently one of hydrogen, a substituted or unsubstituted $C_1$ to $C_{30}$ alkyl group, a substituted or unsubstituted $C_6$ to $C_{30}$ aryl group, a substituted or unsubstituted $C_3$ to $C_{30}$ heteroaryl group, a halogen, a halogen-containing group, and a combination thereof,
a, b and c are integers ranging from 1 to 3, and
Z is a monovalent substituent.

For example, Z may be a halogen or a halogen-containing group, for example F, Cl, a F-containing group, or a Cl-containing group.

The halogen may refer to F, Cl, Br, or I, and the halogen-containing group may refer to an alkyl group where at least one of hydrogen is substituted with F, Cl, Br, or I.

The thiophene derivative may be, for example represented by Chemical Formula 7 or Chemical Formula 8, but is not limited thereto.

[Chemical Formula 7]

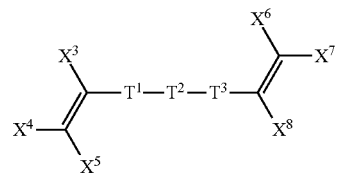

[Chemical Formula 8]

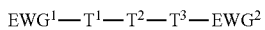

In Chemical Formulae 7 and 8,
each of $T^1$, $T^2$ and $T^3$ are aromatic rings including substituted or unsubstituted thiophene moieties,
each of $T^1$, $T^2$ and $T^3$ are independently present or are fused to each other,
each of $X^3$ to $X^8$ are independently one of hydrogen, a substituted or unsubstituted $C_1$ to $C_{30}$ alkyl group, a substituted or unsubstituted $C_6$ to $C_{30}$ aryl group, a substituted or unsubstituted $C_3$ to $C_{30}$ heterocyclic group, a cyano group, and a combination thereof, and
each of $EWG^1$ and $EWG^2$ are independently electron withdrawing groups.

For example, in the Chemical Formula 7, at least one of $X^3$ to $X^8$ is an electron withdrawing group, for example a cyano group or a cyano-containing group.

The active layer 30 may further include a second p-type semiconductor compound selectively absorbing green light. The second p-type semiconductor compound may be a compound represented by Chemical Formula 9.

[Chemical Formula 9]

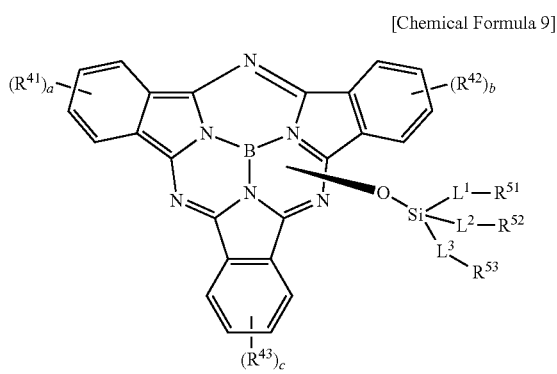

In Chemical Formula 9, each of $R^{41}$ to $R^{43}$ are independently one of hydrogen, a substituted or unsubstituted $C_1$ to $C_{30}$ aliphatic hydrocarbon group, a substituted or unsubstituted $C_6$ to $C_{30}$ aromatic hydrocarbon group, a substituted or unsubstituted $C_1$ to $C_{30}$ aliphatic heterocyclic group, a substituted or unsubstituted $C_2$ to $C_{30}$ aromatic heterocyclic group, a substituted or unsubstituted $C_1$ to $C_{30}$ alkoxy group, a substituted or unsubstituted $C_6$ to $C_{30}$ aryloxy group, a thiol group, a substituted or unsubstituted $C_1$ to $C_{30}$ alkylthio group, a substituted or unsubstituted $C_6$ to $C_{30}$ arylthio group, a cyano group, a cyano-containing group, a halogen, a halogen-containing group, a substituted or unsubstituted sulfonyl group (e.g., a substituted or unsubstituted $C_1$ to $C_{30}$ aminosulfonyl group, a substituted or unsubstituted $C_1$ to $C_{30}$ alkylsulfonyl group, or a substituted or unsubstituted arylsulfonyl group), or a combination thereof, or $R^{41}$ to $R^{43}$ are linked to each other to provide a fused ring, each of $L^1$ to $L^3$ are independently one of a single bond, a substituted or unsubstituted $C_1$ to $C_{30}$ alkylene group, a substituted or unsubstituted $C_6$ to $C_{30}$ arylene group, a divalent substituted or unsubstituted $C_3$ to $C_{30}$ heterocyclic group, and a combination thereof, each of $R^{51}$ to $R^{53}$ are independently one of a substituted or unsubstituted $C_1$ to $C_{30}$ alkyl group, a substituted or unsubstituted $C_6$ to $C_{30}$ aryl group, a substituted or unsubstituted $C_3$ to $C_{30}$ heterocyclic group, a substituted or unsubstituted $C_1$ to $C_{30}$ alkoxy group, a substituted or unsubstituted amine group (e.g., a substituted or unsubstituted $C_1$ to $C_{30}$ alkylamine group or a substituted or unsubstituted $C_6$ to $C_{30}$ arylamine group), a substituted or unsubstituted silyl group, and a combination thereof, and each of a to c are independently integers ranging from 0 to 4.

The second p-type semiconductor compound selectively absorbing green light may be included in an amount of about 500 to about 1500 parts by weight based on 100 parts by weight of the compound represented by Chemical Formula 1.

The active layer 30 may be a single layer or a multilayer. The active layer 30 may be, for example, an intrinsic layer (I layer), a p-type layer/I layer, an I layer/n-type layer, a p-type layer/I layer/n-type layer, a p-type layer/n-type layer, etc.

The intrinsic layer (I layer) may include the compound of Chemical Formula 1 and the n-type semiconductor compound in a ratio of about 1:100 to about 100:1. The compound of Chemical Formula 1 and the n-type semiconductor compound may be included in a ratio ranging from about 1:50 to about 50:1 within the range, for example, about 1:10 to about 10:1, or about 1:1. When the compound of Chemical Formula 1 and the n-type semiconductor compound have a composition ratio within the range, an exciton may be effectively produced and a pn junction may be effectively formed.

The p-type layer may include the semiconductor compound of Chemical Formula 1, and the n-type layer may include the n-type semiconductor compound.

The active layer 30 may have a thickness of about 1 nm to about 500 nm, for example, about 5 nm to about 300 nm. When the active layer 30 has a thickness within the range, the active layer may effectively absorb light, effectively separate holes from electrons, and deliver them, thereby effectively improving photoelectronic conversion efficiency. An optimal thickness of a thin film may be, for example, determined by an absorption coefficient of the active layer 30, and may be, for example, a thickness being capable of absorbing light of at least about 70 or more, for example about 80% or more, and for another example about 90%.

In the organic photoelectric device 100, when light enters from the first electrode 10 and/or second electrode 20, and when the active layer 30 absorbs light having a predetermined or given wavelength region, excitons may be produced from the inside. The excitons are separated into holes and electrons in the active layer 30, and the separated holes are transported to an anode that is one of the first electrode 10 and second electrode 20 and the separated electrons are transported to the cathode that is the other of and the first electrode 10 and second electrode 20 so as to flow a current in the organic photoelectric device.

Hereinafter, an organic photoelectric device according to example embodiments is described with reference to FIG. 2.

Figure 2:
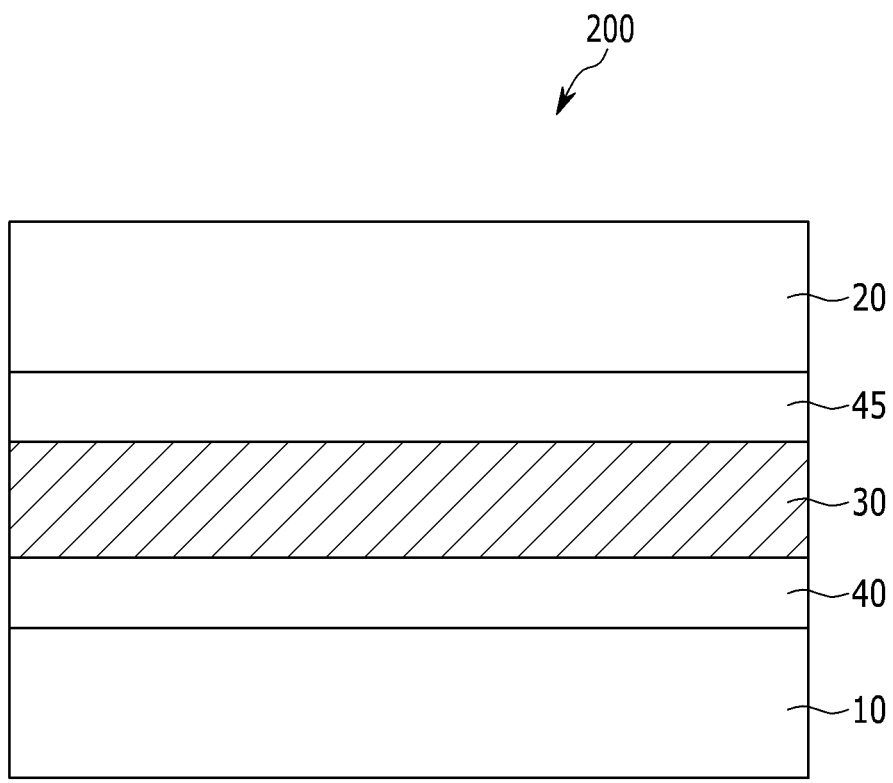
FIG. 2 is a cross-sectional view of an organic photoelectric device according to example embodiments.

FIG. 2 is a cross-sectional view of an organic photoelectric device according to example embodiments.

Referring to FIG. 2, an organic photoelectric device 200 according to example embodiments includes a first electrode 10 and a second electrode 20 facing each other, and an active layer 30 between the first electrode 10 and the second electrode 20, like the example embodiment illustrated in FIG. 1.

However, the organic photoelectric device 200 according to example embodiments further includes charge auxiliary layers 40 and 45 between the first electrode 10 and the active layer 30, and the second electrode 20 and the active layer 30, unlike the example embodiment illustrated in FIG. 1. The charge auxiliary layers 40 and 45 may facilitate the transfer of holes and electrons separated from the active layer 30, so as to increase efficiency.

The charge auxiliary layers 40 and 45 may be at least one selected from a hole injection layer (HIL) for facilitating hole injection, a hole transport layer (HTL) for facilitating hole transport, an electron blocking layer (EBL) for preventing or inhibiting electron transport, an electron injection layer (EIL) for facilitating electron injection, an electron transport layer (ETL) for facilitating electron transport, and a hole blocking layer (HBL) for preventing or inhibiting hole transport.

The charge auxiliary layers 40 and 45 may include, for example, an organic material, an inorganic material, or an organic/inorganic material. The organic material may be an organic compound having hole or electron characteristics, and the inorganic material may be, for example, a metal oxide such as molybdenum oxide, tungsten oxide, nickel oxide, etc.

The hole transport layer (HTL) may include one selected from, for example, poly(3,4-ethylenedioxythiophene):poly(styrenesulfonate) (PEDOT:PSS), polyarylamine, poly(N- vinylcarbazole), polyaniline, polypyrrole, N,N,N',N'-tetrakis(4-methoxyphenyl)-benzidine (TPD), 4,4'-bis[N-(1-naphthyl)-N-phenyl-amino]biphenyl (α-NPD), m-MTDATA, 4,4',4"-tris(N-carbazolyl)-triphenylamine (TCTA), and a combination thereof, but is not limited thereto.

The electron blocking layer (EBL) may include one selected from, for example, poly(3,4-ethylenedioxythiophene):poly(styrenesulfonate) (PEDOT:PSS), polyarylamine, poly(N-vinylcarbazole), polyaniline, polypyrrole, N,N,N',N'-tetrakis(4-methoxyphenyl)-benzidine (TPD), 4,4'-bis[N-(1-naphthyl)-N-phenyl-amino]biphenyl (α-NPD), m-MTDATA, 4,4',4"-tris(N-carbazolyl)-triphenylamine (TCTA), and a combination thereof, but is not limited thereto.

The electron transport layer (ETL) may include one selected from, for example, 1,4,5,8-naphthalene-tetracarboxylic dianhydride (NTCDA), bathocuproine (BCP), LiF, $Alq_3$, $Gaq_3$, $Inq_3$, $Znq_2$, $Zn(BTZ)_2$, $BeBq_2$, and a combination thereof, but is not limited thereto.

The hole blocking layer (HBL) may include one selected from, for example, 1,4,5,8-naphthalene-tetracarboxylic dianhydride (NTCDA), bathocuproine (BCP), LiF, $Alq_3$, $Gaq_3$, $Inq_3$, $Znq_2$, $Zn(BTZ)_2$, $BeBq_2$, and a combination thereof, but is not limited thereto.

Either one of the charge auxiliary layers 40 and 45 may be omitted.

The organic photoelectric device may be applied to various fields, for example a solar cell, an image sensor, a photo-detector, a photo-sensor, and an organic light emitting diode (OLED), but is not limited thereto.

Hereinafter, an example of an image sensor including the organic photoelectric device is described referring to drawings. As an example of an image sensor, an organic CMOS image sensor is described.

Figure 3:
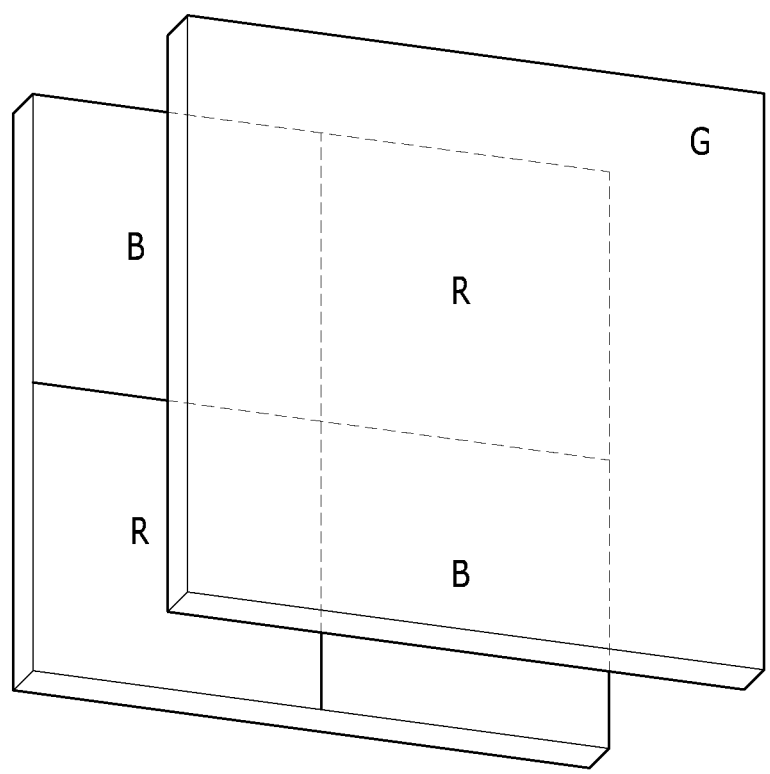
FIG. 3 is a schematic top plan view showing an organic CMOS image sensor according to example embodiments.
Figure 4:
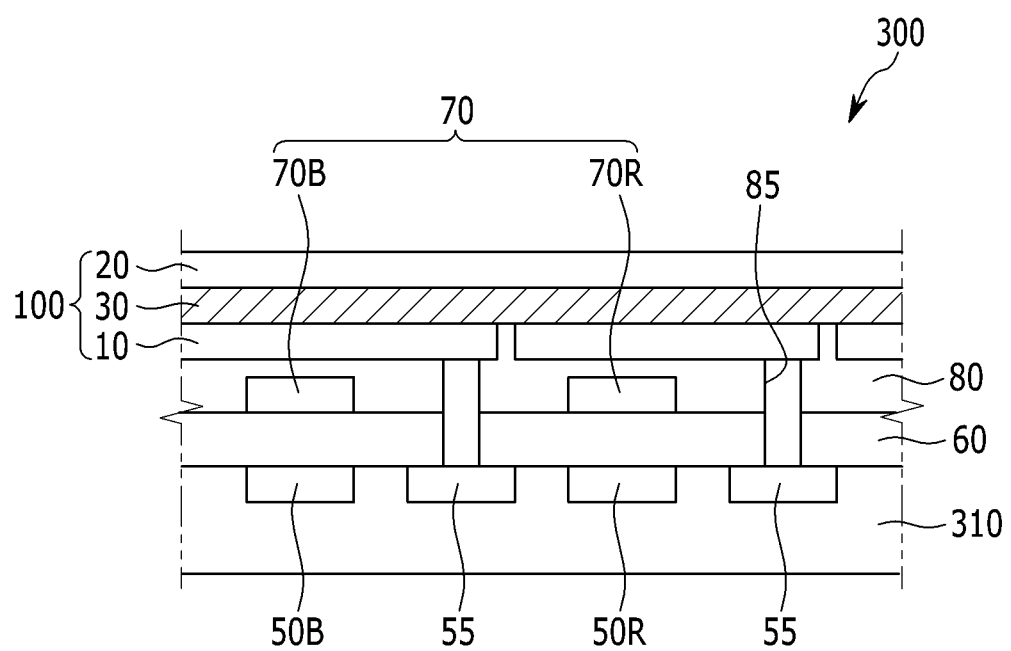
FIG. 4 is a cross-sectional view showing the organic CMOS image sensor of FIG. 3.

FIG. 3 is a schematic top plan view of an organic CMOS image sensor according to example embodiments, and FIG. 4 is a cross-sectional view of the organic CMOS image sensor of FIG. 3.

Referring to FIGS. 3 and 4, an organic CMOS image sensor 300 according to example embodiments includes a semiconductor substrate 310 integrated with photo-sensing devices 50B and 50R, a transmission transistor (not shown), a charge storage device 55, a lower insulation layer 60, a color filter layer 70, an upper insulation layer 80, and an organic photoelectric device 100.

The semiconductor substrate 310 may be a silicon substrate, and is integrated with the photo-sensing devices 50B and 50R, the transmission transistor (not shown), and the charge storage device 55. The photo-sensing devices 50R and 50B may be photodiodes.

The photo-sensing devices 50B and 50R, the transmission transistor, and/or the charge storage device 55 may be integrated in each pixel, and as shown in the drawing, the photo-sensing devices 50B and 50R may be respectively included in a blue pixel and a red pixel and the charge storage device 55 may be included in a green pixel.

The photo-sensing devices 50B and 50R sense light, the information sensed by the photo-sensing devices may be transferred by the transmission transistor, the charge storage device 55 is electrically connected with the organic photoelectric device 100, and the information of the charge storage device 55 may be transferred by the transmission transistor.

In the drawings, the photo-sensing devices 50B and 50R are, for example, arranged in parallel without limitation, and the blue photo-sensing device 50B and the red photo-sensing device 50R may be stacked in a vertical direction.

A metal wire (not shown) and a pad (not shown) are formed on the semiconductor substrate 310. In order to decrease signal delay, the metal wire and pad may be made of a metal having low resistivity, for example, aluminum (Al), copper (Cu), silver (Ag), and alloys thereof, but are not limited thereto. Further, it is not limited to the structure, and the metal wire and pad may be positioned under the photo-sensing devices 50B and 50R.

The lower insulation layer 60 is formed on the metal wire and the pad. The lower insulation layer 60 may be made of an inorganic insulating material such as a silicon oxide and/or a silicon nitride, or a low dielectric constant (low K) material such as SiC, SiCOH, SiCO, and SiOF. The lower insulation layer 60 has a trench exposing the charge storage device 55. The trench may be filled with fillers.

A color filter layer 70 is formed on the lower insulation layer 60. The color filter layer 70 includes a blue filter 70B formed in the blue pixel and selectively transmitting blue light and a red filter 70R formed in the red pixel and selectively transmitting red light. In example embodiments, a green filter is not included, but a green filter may be further included.

The color filter layer 70 may be omitted. For example, when the blue photo-sensing device 50B and the red photo-sensing device 50R are stacked in a vertical direction, the blue photo-sensing device 50B and the red photo-sensing device 50R may selectively absorb and/or sense light in each wavelength region depending on their stack depth, and the color filter layer 70 may not be equipped.

The upper insulation layer 80 is formed on the color filter layer 70. The upper insulation layer 80 eliminates a step caused by the color filter layer 70 and smoothes the surface. The upper insulation layer 80 and the lower insulation layer 60 may include a contact hole (not shown) exposing a pad, and a through-hole 85 exposing the charge storage device 55 of the green pixel.

The organic photoelectric device 100 is formed on the upper insulation layer 80. The organic photoelectric device 100 includes the first electrode 10, the active layer 30, and the second electrode 20 as described above.

The first electrode 10 and the second electrode 20 may be transparent electrodes, and the active layer 30 is the same as described above. The active layer 30 selectively absorbs and/or senses light in a green wavelength region and replaces a color filter of a green pixel.

When light enters from the second electrode 20, the light in a green wavelength region may be mainly absorbed in the active layer 30 and photoelectronically converted, while the light in the rest of the wavelength regions passes through first electrode 10 and may be sensed in the photo-sensing devices 50B and 50R.

As described above, the organic photoelectric devices selectively absorbing and/or sensing light in a green wavelength region are stacked and thereby a size of an image sensor may be decreased and a down-sized image sensor may be realized.

As described above, the compound represented by the Chemical Formula 1 may be used as a p-type semiconductor compound, aggregation between compounds in a thin film state is inhibited, and thereby light absorption characteristics depending on a wavelength may be maintained. Thereby, green wavelength selectivity may be maintained, crosstalk caused by unnecessary absorption of other light except a green wavelength region may be decreased and sensitivity may be increased.

Figure 5:
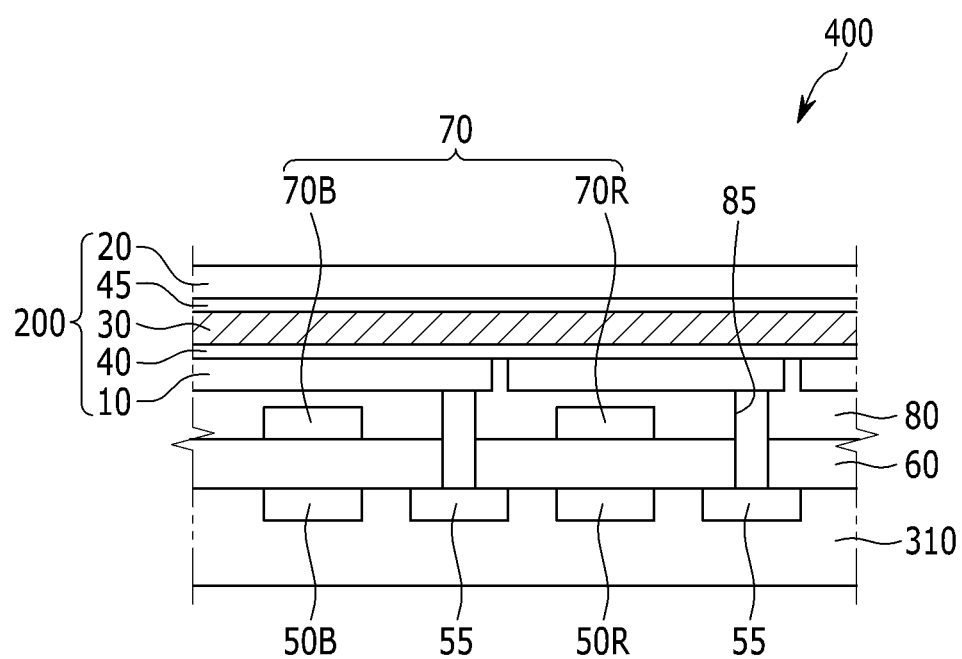
FIG. 5 is a schematic cross-sectional view showing an organic CMOS image sensor according to example embodiments.

In FIG. 4, the organic photoelectric device 100 of FIG. 1 is included, but it is not limited thereto, and thus the organic photoelectric device 200 of FIG. 2 may be applied in the same manner. FIG. 5 shows a structure of an image sensor having such a structure, and is a cross-sectional view of an organic CMOS image sensor 400 including the organic photoelectric device 200 in FIG. 2.

Figure 6:
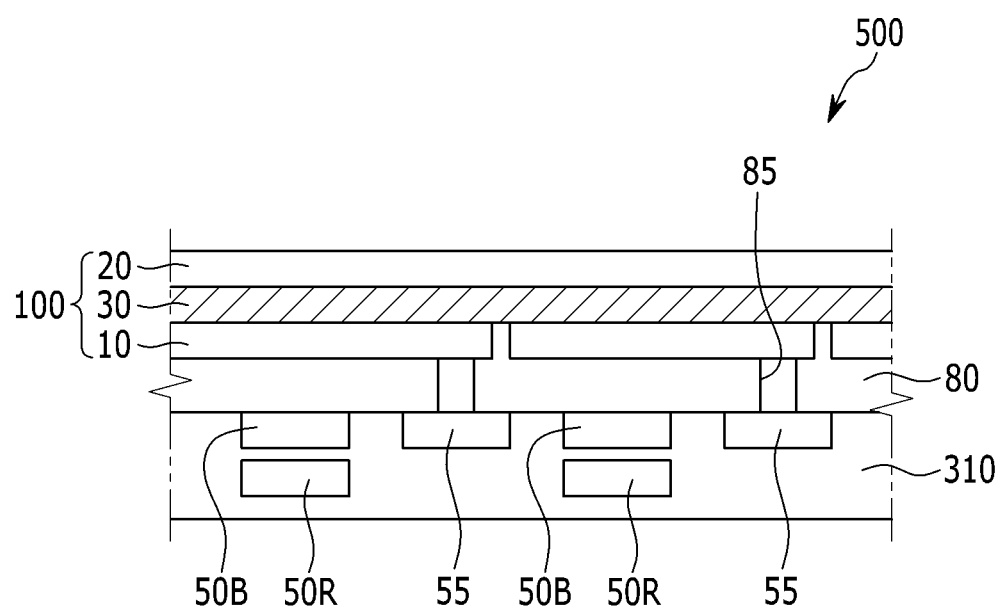
FIG. 6 is a schematic cross-sectional view showing an organic CMOS image sensor according to example embodiments.

FIG. 6 is a cross-sectional view showing the organic CMOS image sensor according to example embodiments.

The organic CMOS image sensor 500 includes a semiconductor substrate 310 integrated with photo-sensing devices 50B and 50R, a transmission transistor (not shown), a charge storage device 55, an insulation layer 80, and an organic photoelectric device 100, like the example embodiment illustrated in FIG. 5.

However, the organic CMOS image sensor 500 according to the example embodiment illustrated in FIG. 6 includes the blue photo-sensing device 50B and the red photo-sensing device 50R that are stacked and does not include a color filter layer 70, unlike the example embodiment illustrated in FIG. 5. The blue photo-sensing device 50B and the red photo-sensing device 50R are electrically connected with the charge storage device 55, and the information of the charge storage device 55 may be transferred by the transmission transistor (not shown). The blue photo-sensing device 50B and the red photo-sensing device 50R may selectively absorb and/or sense light in each wavelength region depending on a stack depth.

As described above, the organic photoelectric devices selectively absorbing and/or sensing light in a green wavelength region are stacked and the red photo-sensing device and the blue photo-sensing device are stacked, and thereby a size of an image sensor may be decreased and a down-sized image sensor may be realized. As described above, the organic photoelectric device 100 has improved green wavelength selectivity, and crosstalk caused by unnecessary absorption light in a wavelength region except green may be decreased while increasing sensitivity.

In FIG. 6, the organic photoelectric device 100 of FIG. 1 is included, but it is not limited thereto, and thus the organic photoelectric device 200 of FIG. 2 may be applied in the same manner.

Figure 7:
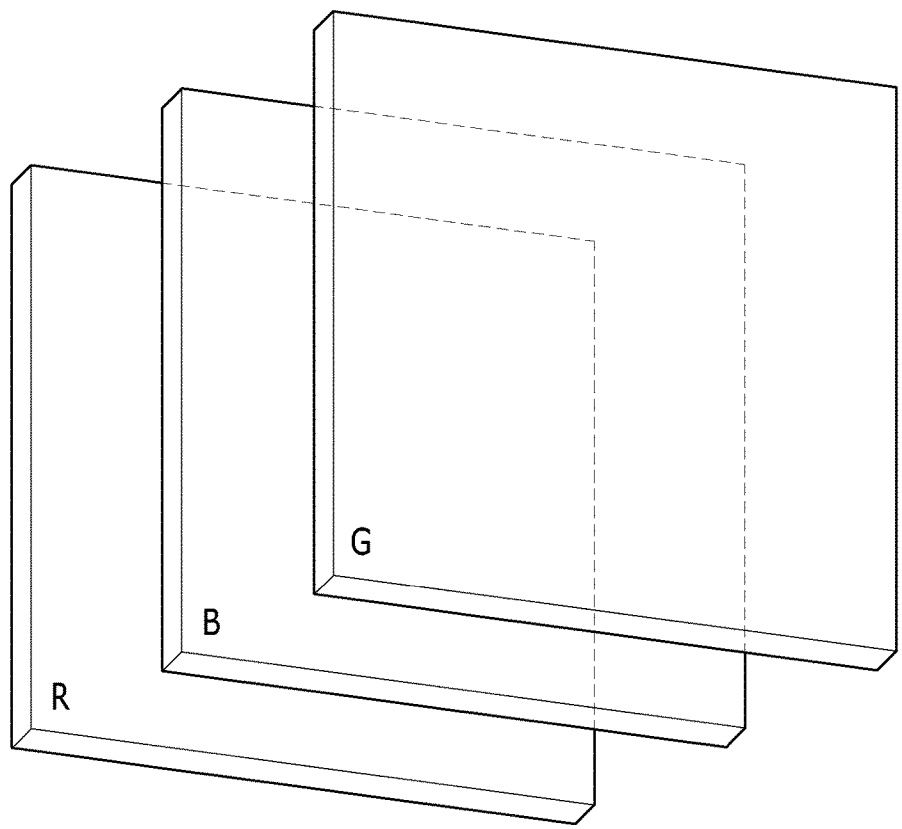
FIG. 7 is a schematic view showing an organic CMOS image sensor according to example embodiments.

FIG. 7 is a schematic view showing an organic CMOS image sensor according to example embodiments.

Referring to FIG. 7, the organic CMOS image sensor according to example embodiments includes a green photoelectric device (G) selectively absorbing and/or sensing light in a green wavelength region, a blue photoelectric device (B) selectively absorbing and/or sensing light in a blue wavelength region, and a red photoelectric device selectively sensing and/or absorbing light in a red wavelength region that are stacked.

In the drawing, the red photoelectric device (R), the blue photoelectric device (B), and the green photoelectric device (G) are sequentially stacked, but the stack order may be changed without limitation.

The green photoelectric device (G) may be the above organic photoelectric device 100, the blue photoelectric device (B) may include electrodes facing each other and an active layer interposed therebetween and including an organic material selectively sensing and/or absorbing light in a blue wavelength region, and the red photoelectric device (R) may include electrodes facing each other and an active layer interposed therebetween and including an organic material selectively absorbing and/or sensing light in a red wavelength region.

As described above, the organic photoelectric device (G) selectively absorbing and/or sensing light in a green wavelength region, the organic photoelectric device (B) selectively absorbing and/or sensing light in a blue wavelength region and the organic photoelectric device (R) selectively absorbing and/or sensing light in a red wavelength region are stacked, and thereby a size of an image sensor may be decreased and a down-sized image sensor may be realized.

The image sensor may be applied to various electronic devices, for example, a mobile phone and/or a digital camera, but is not limited thereto.

Hereinafter, the present disclosure is illustrated in more detail with reference to examples. However, these are examples, and the present disclosure is not limited thereto.

Synthesis Example 1: Synthesis of the Compound Represented by Chemical Formula 1-1 (2-((5-(naphthalen-1-yl(phenyl)amino)selenophen-2-yl)methylene)-1H-indene-1,3(2H)-dione)

[Chemical Formula 1-1]

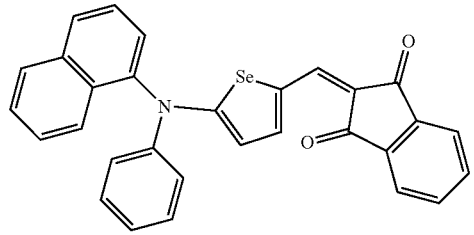

[Reaction Scheme 1]

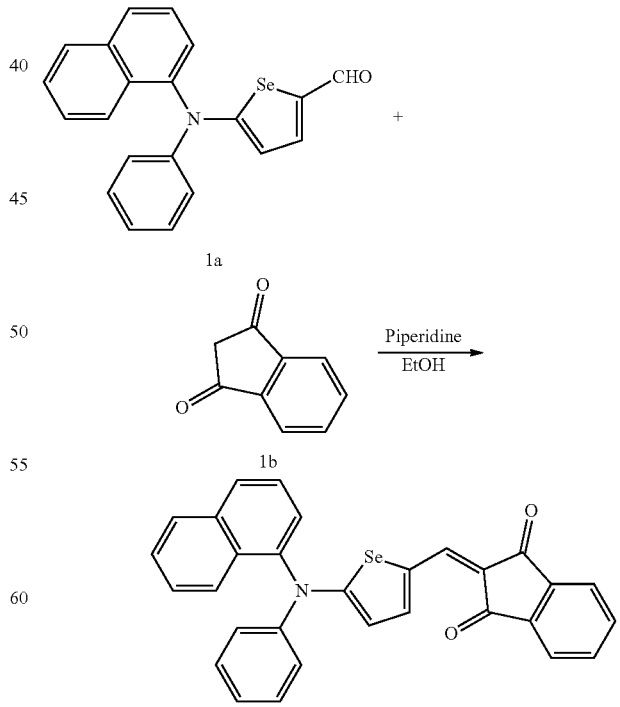

Figure 8:
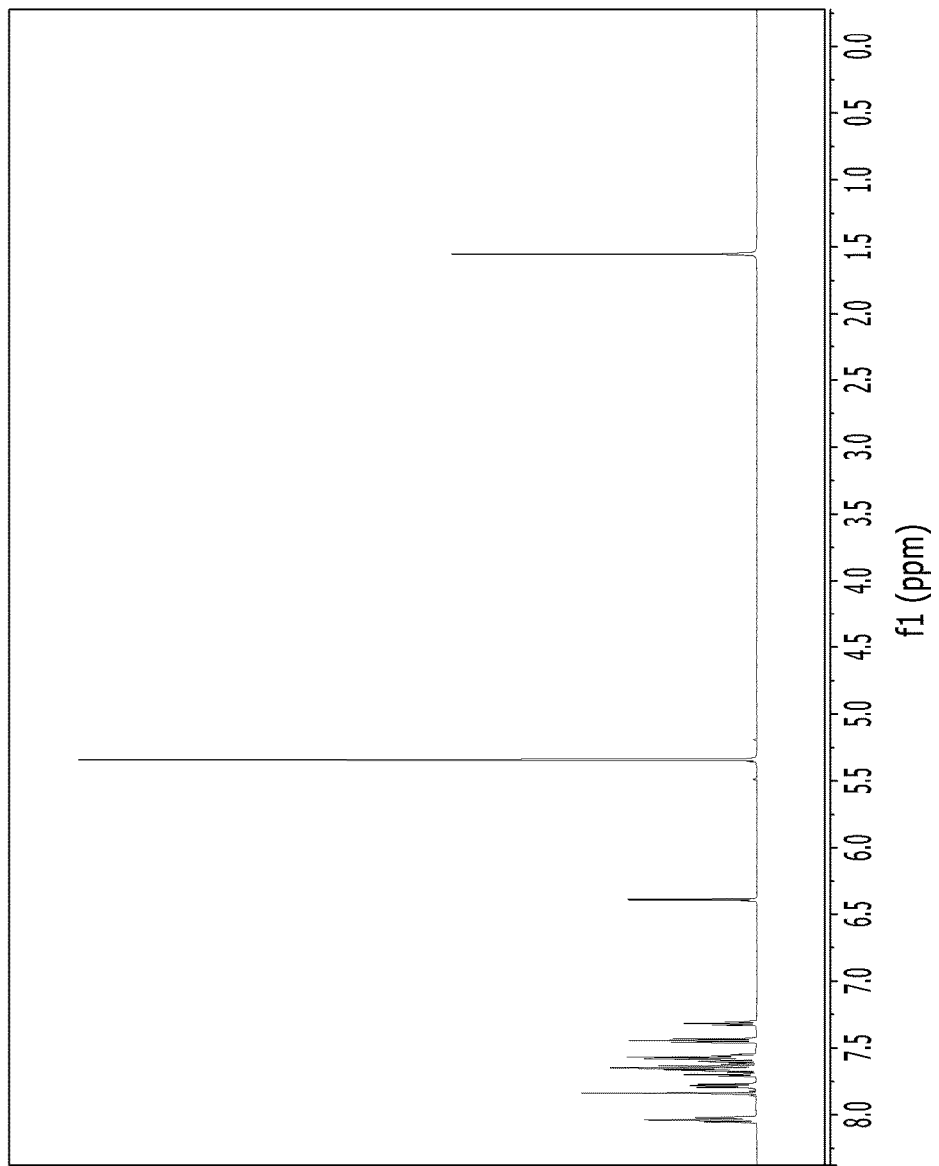
FIGS. 8 to 17 are graphs showing $^1$H-NMR results of the compounds of Synthesis Examples 1 to 10, respectively.

5-(naphthalen-1-yl(phenyl)amino)selenophene-2-carbaldehyde (a compound 1a, 1 mmol) and 1H-indene-1,3(2H)-dione (a compound 1 b, 1 mmol) are mixed with 10 mL of ethanol, and the mixture is stirred. Then, 2 to 3 drops of piperidine are added to the stirred solution, and the mixed solution is stirred at 85° C. for 6 hours. The stirred solution is cooled down to room temperature (24° C.), and a solid precipitated by pouring water thereinto is collected through vacuum-filtering. The collected solid is dissolved in dichloromethane and separated with a mixed solution of dichloromethane and hexane through silica gel column chromatography. After removing a solvent from the separated solution, the obtained solid is recrystallized in a mixed solution of dichloromethane and hexane, obtaining a compound represented by Chemical Formula 1-1. A yield is 95%. $^1$H-NMR (CD$_2$Cl$_2$, 600 MHz) of the compound represented by Chemical Formula 1-1 is shown in FIG. 8.

Synthesis Example 2: Synthesis of the Compound Represented by Chemical Formula 1-2 (2-((5-((4-methylnaphthalen-1-yl)(p-tolyl)amino)selenophen-2-yl)methylene)-1H-indene-1,3(2H)-dione)

[Chemical Formula 1-2]

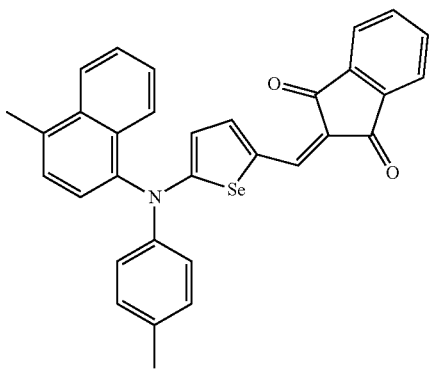

Figure 9:
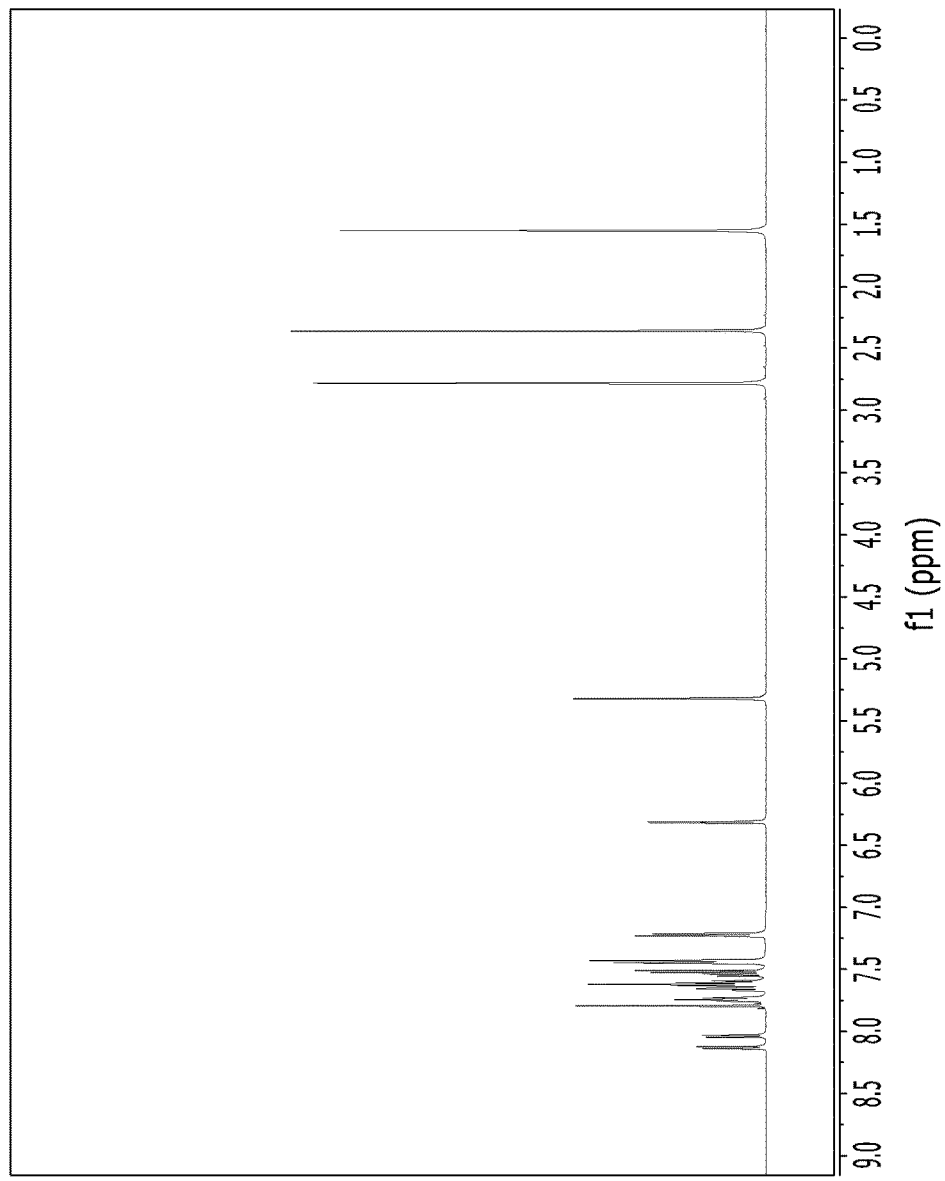

A compound represented by Chemical Formula 1-2 is synthesized according to the same method as Synthesis Example 1 except for using 5-((4-methylnaphthalen-1-yl)(p-tolyl)amino)selenophene-2-carbaldehyde (1 mmol) instead of the compound 1a. A yield is 95%. $^1$H-NMR (CD$_2$Cl$_2$, 300 MHz) of the compound represented by Chemical Formula 1-2 is shown in FIG. 9.

Synthesis Example 3: Synthesis of the Compound Represented by Chemical Formula 1-3 (2-((5-(naphthalen-1-yl(phenyl)amino)selenophen-2-yl)methylene)-1H-cyclopenta[b]naphthalene-1,3(2H)-dione)

[Chemical Formula 1-3]

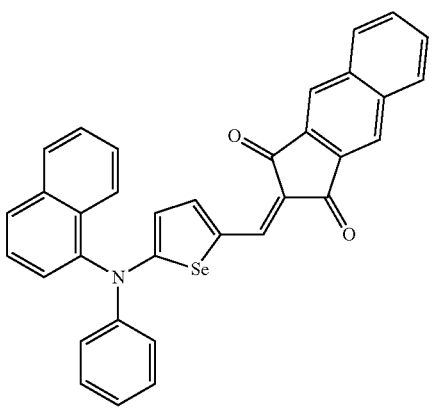

Figure 10:
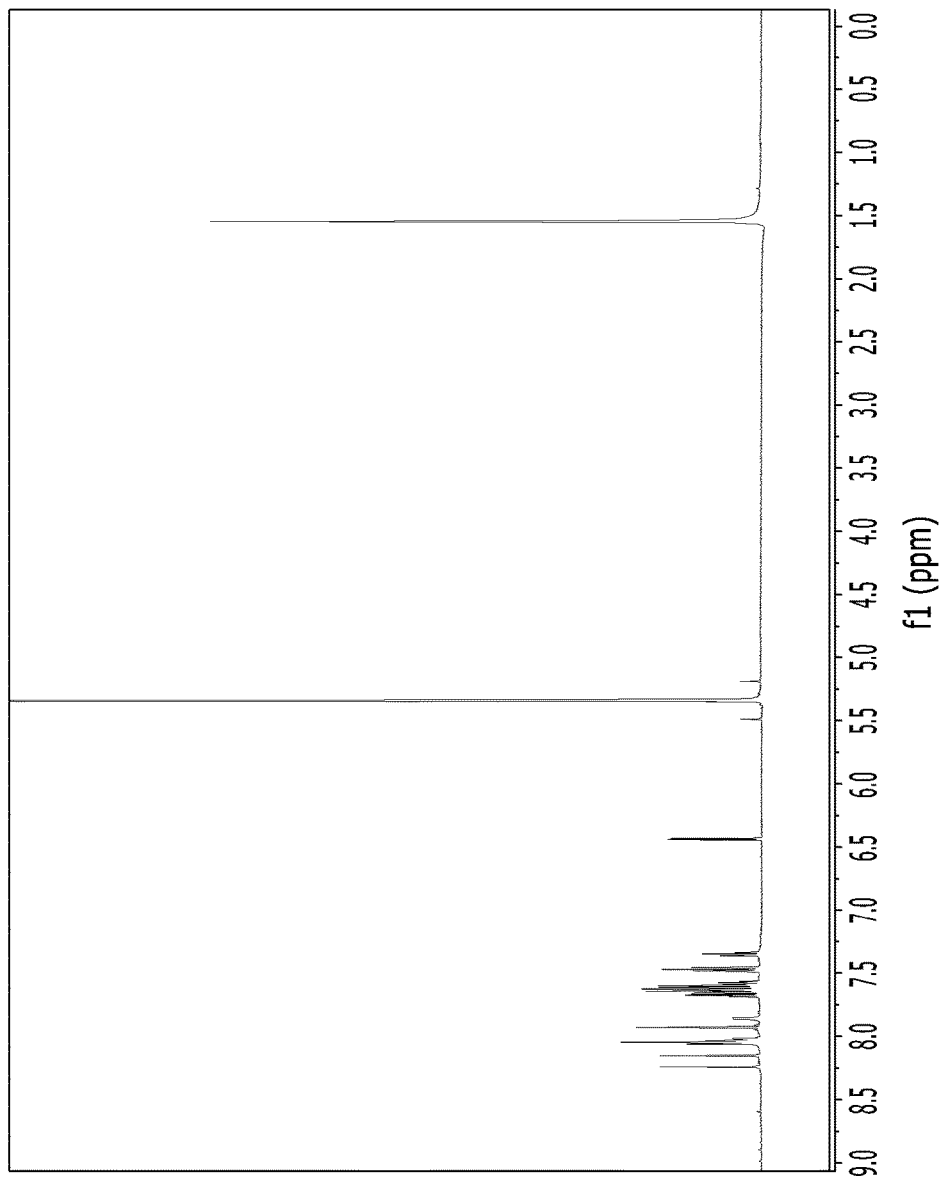

A compound represented by Chemical Formula 1-3 is synthesized according to the same method as Synthesis Example 1 except for using 1H-cyclopenta[b]naphthalene-1,3(2H)-dione (1 mmol) instead of the compound 1b. A yield is 90%. $^1$H-NMR (CD$_2$Cl$_2$, 600 MHz) of the compound represented by Chemical Formula 1-3 is shown in FIG. 10.

Synthesis Example 4: Synthesis of the Compound Represented by Chemical Formula 1-4 (2-((5-((4-methylnaphthalen-1-yl)(phenyl)amino)selenophen-2-yl)methylene)-1H-cyclopenta[b]naphthalene-1,3(2H)-dione)

[Chemical Formula 1-4]

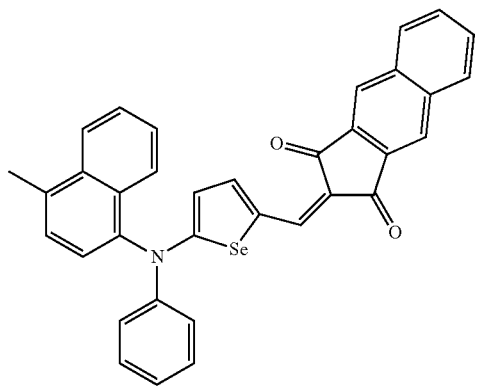

Figure 11:
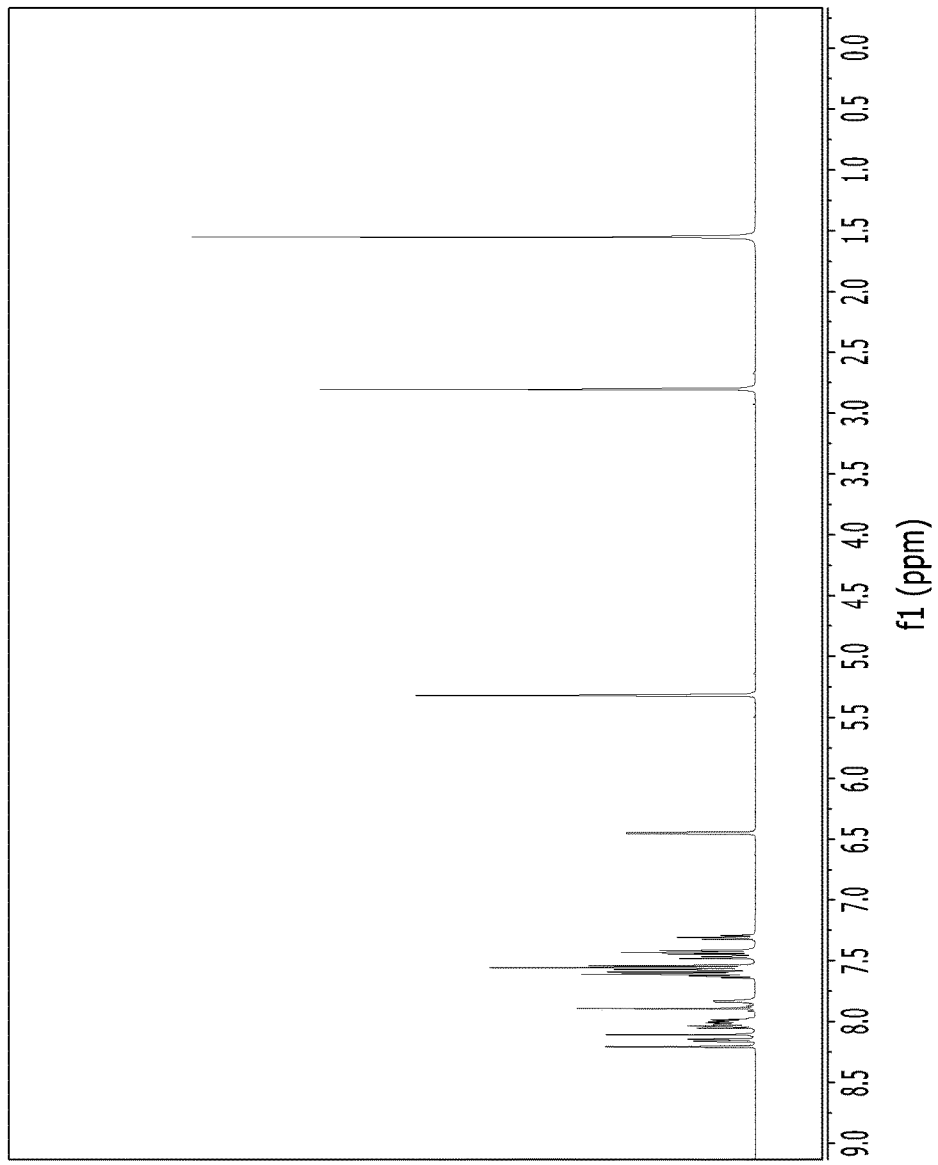

A compound represented by Chemical Formula 1-4 is synthesized according to the same method as Synthesis Example 1 except for using 5-((4-methylnaphthalen-1-yl)(phenyl)amino)selenophene-2-carbaldehyde (1 mmol) instead of the compound 1a and using 1H-cyclopenta[b]naphthalene-1,3(2H)-dione (1 mmol) instead of the compound 1b. A yield is 90%. $^1$H-NMR (CD$_2$Cl$_2$, 300 MHz) of the compound represented by Chemical Formula 1-4 is shown in FIG. 11.

Synthesis Example 5: Synthesis of the Compound Represented by Chemical Formula 1-5 (2-((5-((3,5-dimethylphenyl)(4-methylnaphthalen-1-yl)amino)selenophen-2-yl)methylene)-1H-cyclopenta[b]naphthalene-1,3(2H)-dione)

[Chemical Formula 1-5]

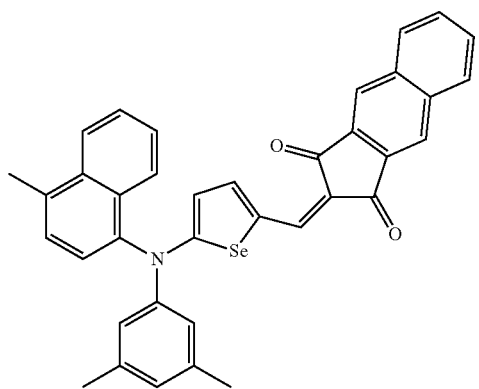

Figure 12:
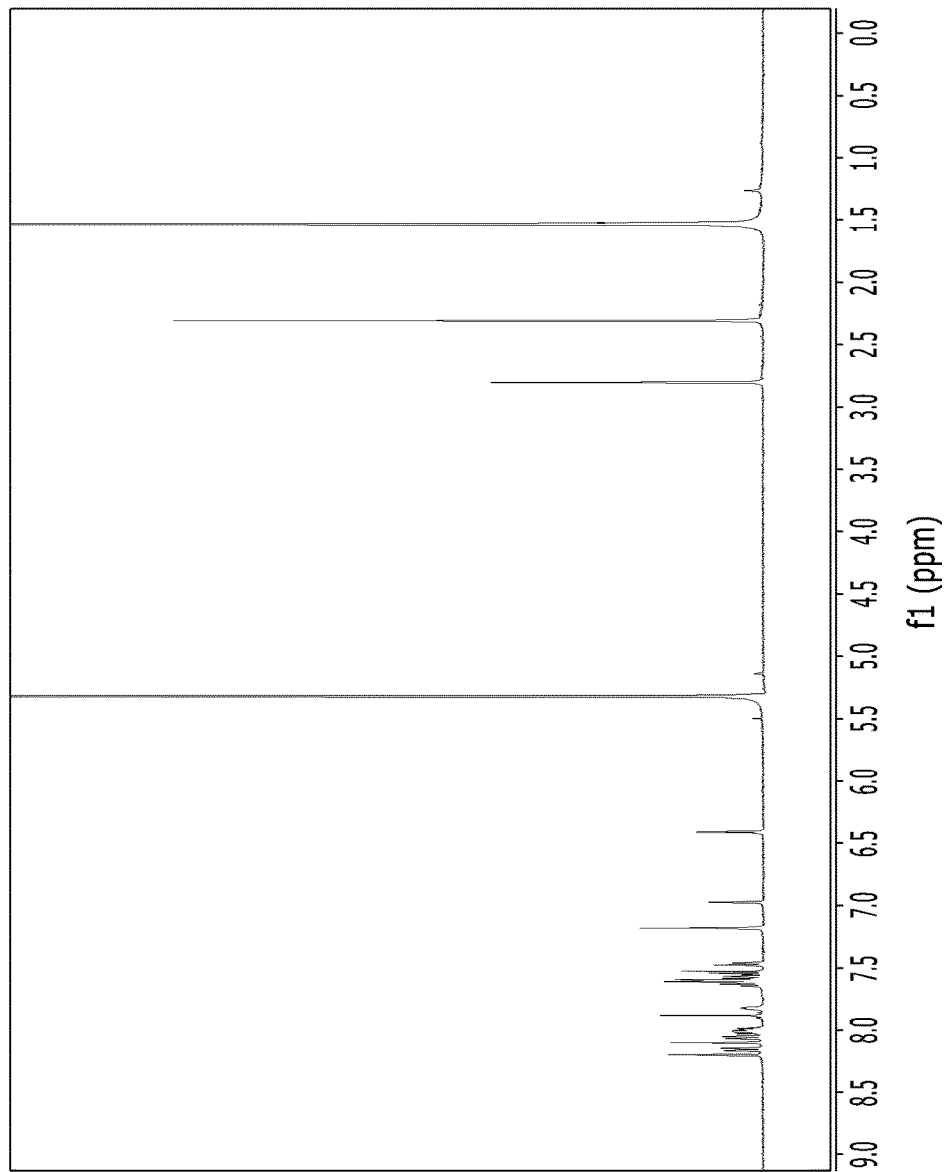

A compound represented by Chemical Formula 1-5 is synthesized according to the same method as Synthesis Example 1 except for using 5-((3,5-dimethylphenyl)(4-methylnaphthalen-1-yl)amino)selenophene-2-carbaldehyde (1 mmol) instead of the compound 1a and using 1H-cyclopenta[b]naphthalene-1,3(2H)-dione (1 mmol) instead of the compound 1b. A yield is 90%. $^1$H-NMR (CD$_2$Cl$_2$, 300 MHz) of the compound represented by Chemical Formula 1-5 is shown in FIG. 12.

Synthesis Example 6: Synthesis of the Compound Represented by Chemical Formula 1-6 (2-((5-((3-chlorophenyl)(naphthalen-1-yl)amino)selenophen-2-yl)methylene)-1H-cyclopenta[b]naphthalene-1,3(2H)-dione)

[Chemical Formula 1-6]

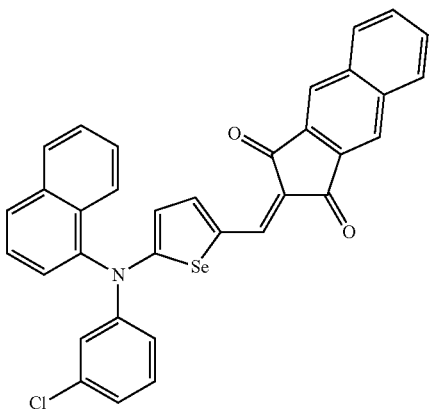

Figure 13:
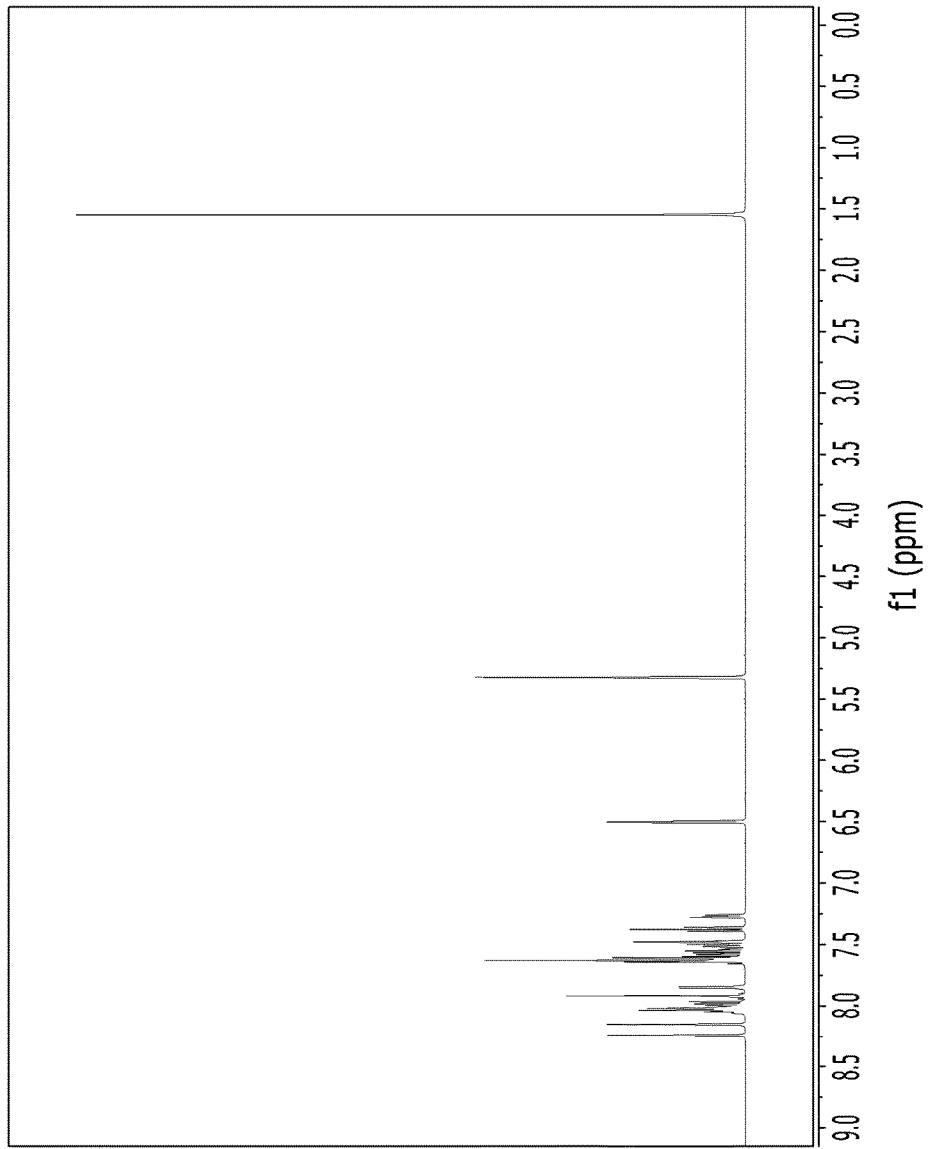

A compound represented by Chemical Formula 1-6 is synthesized according to the same method as Synthesis Example 1 except for using 5-((3-chlorophenyl)(naphthalen-1-yl)amino)selenophene-2-carbaldehyde (1 mmol) instead of the compound 1a and using 1H-cyclopenta[b]naphthalene-1,3(2H)-dione (1 mmol) instead of the compound 1b. A yield is 90%. $^1$H-NMR (CD$_2$Cl$_2$, 300 MHz) of the compound represented by Chemical Formula 1-6 is shown in FIG. 13.

Synthesis Example 7: Synthesis of the Compound Represented by Chemical Formula 1-7 (2-((5-((3-chlorophenyl)(4-methylnaphthalen-1-yl)amino)selenophen-2-yl)methylene)-1H-cyclopenta[b]naphthalene-1,3(2H)-dione)

[Chemical Formula 1-7]

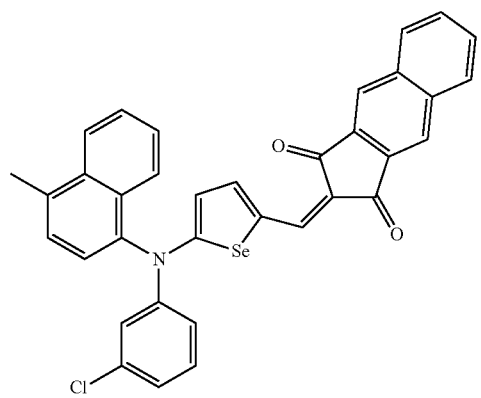

Figure 14:
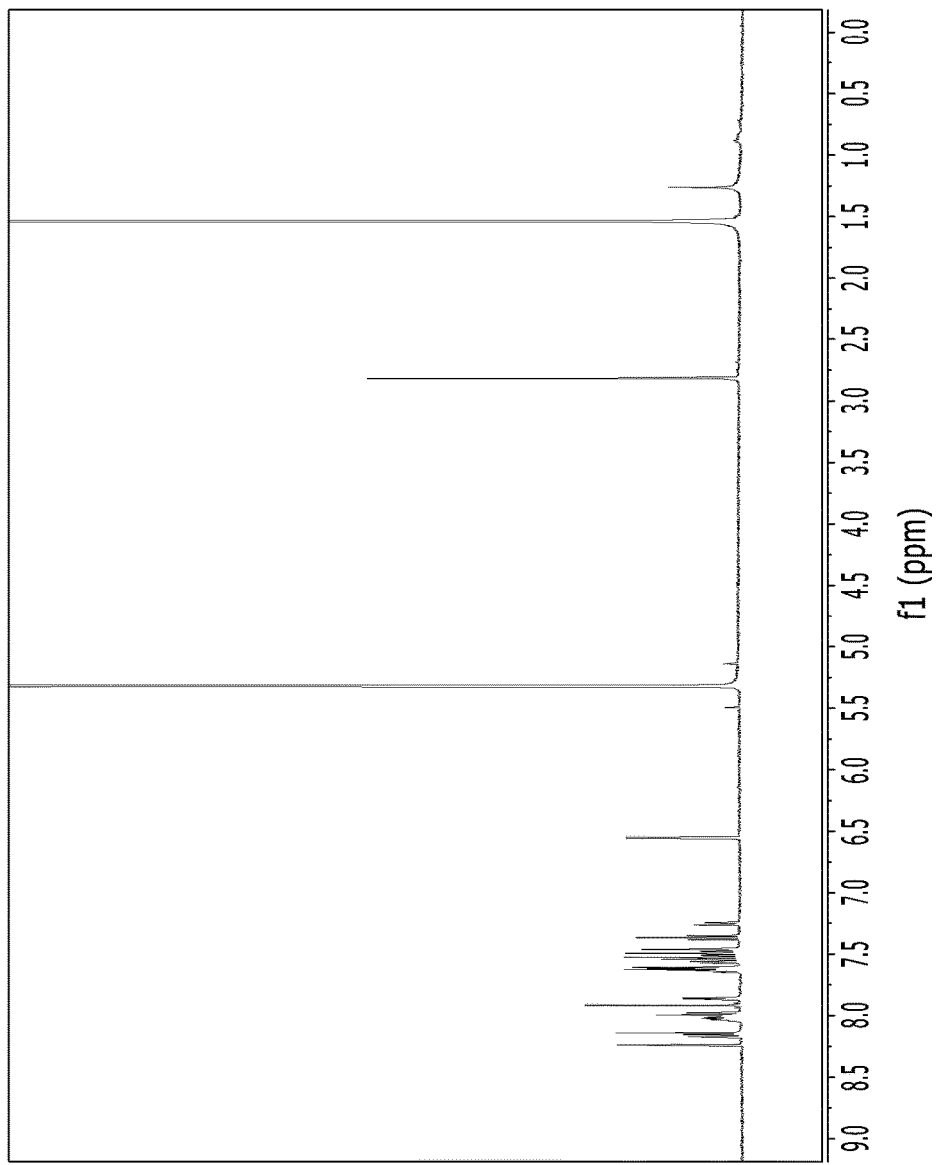

A compound represented by Chemical Formula 1-7 is synthesized according to the same method as Synthesis Example 1 except for using 5-((3-chlorophenyl) (4-methylnaphthalen-1-yl)amino)selenophene-2-carbaldehyde (1 mmol) instead of the compound 1a and using 1H-cyclopenta[b]naphthalene-1,3(2H)-dione (1 mmol) instead of the compound 1b. A yield is 90%. $^1$H-NMR (CD$_2$Cl$_2$, 300 MHz) of the compound represented by Chemical Formula 1-7 is shown in FIG. 14.

Synthesis Example 8: Synthesis of the Compound Represented by Chemical Formula 1-8 (2-((5-((4-chlorophenyl)(naphthalen-1-yl)amino)selenophen-2-yl)methylene)-1H-cyclopenta[b]naphthalene-1,3(2H)-dione)

[Chemical Formula 1-8]

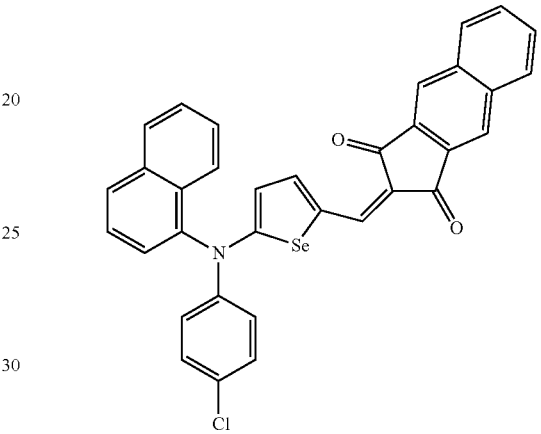

Figure 15:
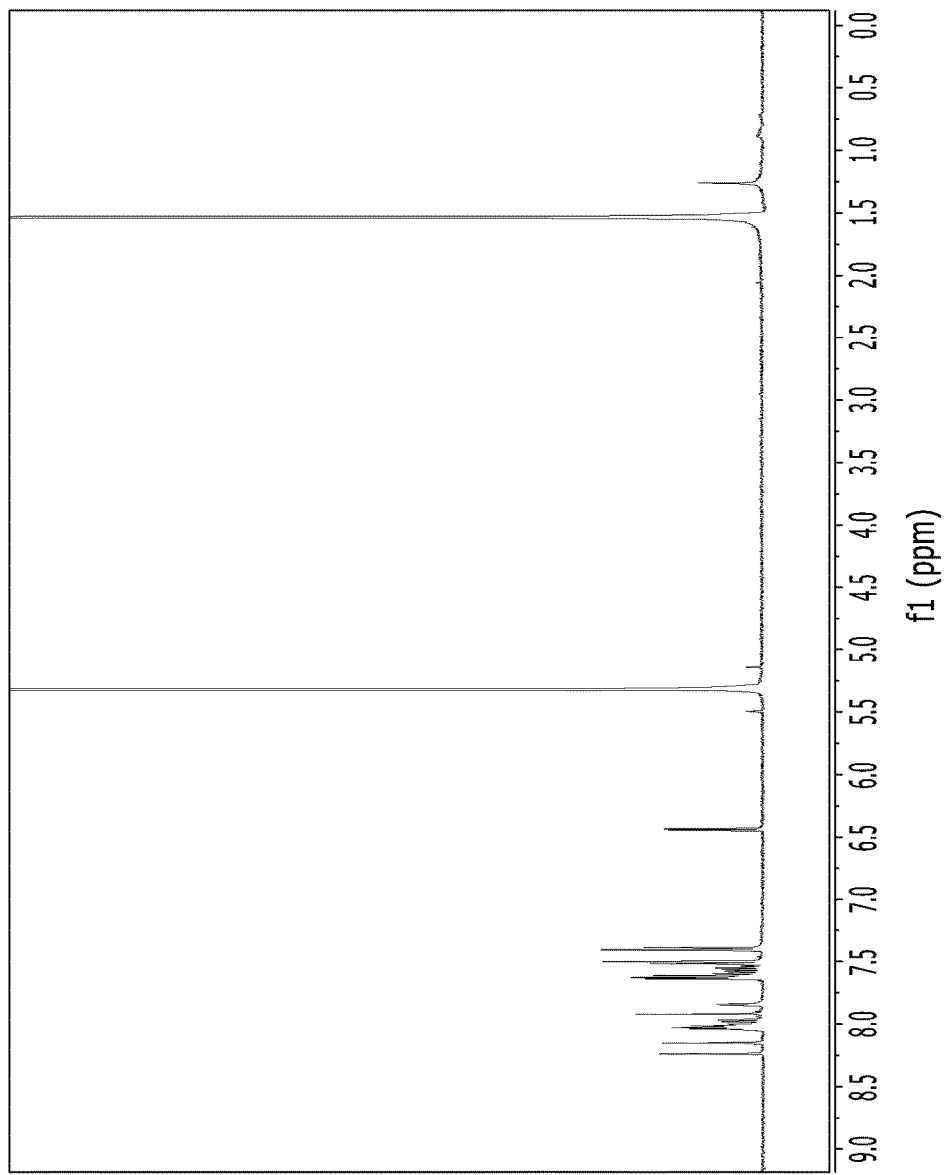

A compound represented by Chemical Formula 1-8 is synthesized according to the same method as Synthesis Example 1 except for using 5-((4-chlorophenyl) (naphthalen-1-yl)amino)selenophene-2-carbaldehyde (1 mmol) instead of the compound 1a and using 1H-cyclopenta[b]naphthalene-1,3(2H)-dione (1 mmol) instead of the compound 1b. A yield is 90%. $^1$H-NMR (CD$_2$Cl$_2$, 300 MHz) of the compound represented by Chemical Formula 1-8 is shown in FIG. 15.

Synthesis Example 9: Synthesis of the Compound Represented by Chemical Formula 1-9 (2-((5-((4-chlorophenyl)(4-methylnaphthalen-1-yl)amino)selenophen-2-yl)methylene)-1H-cyclopenta[b]naphthalene-1,3(2H)-dione)

[Chemical Formula 1-9]

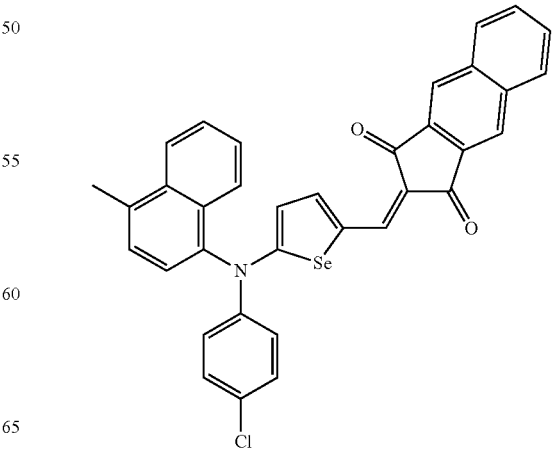

Figure 16:
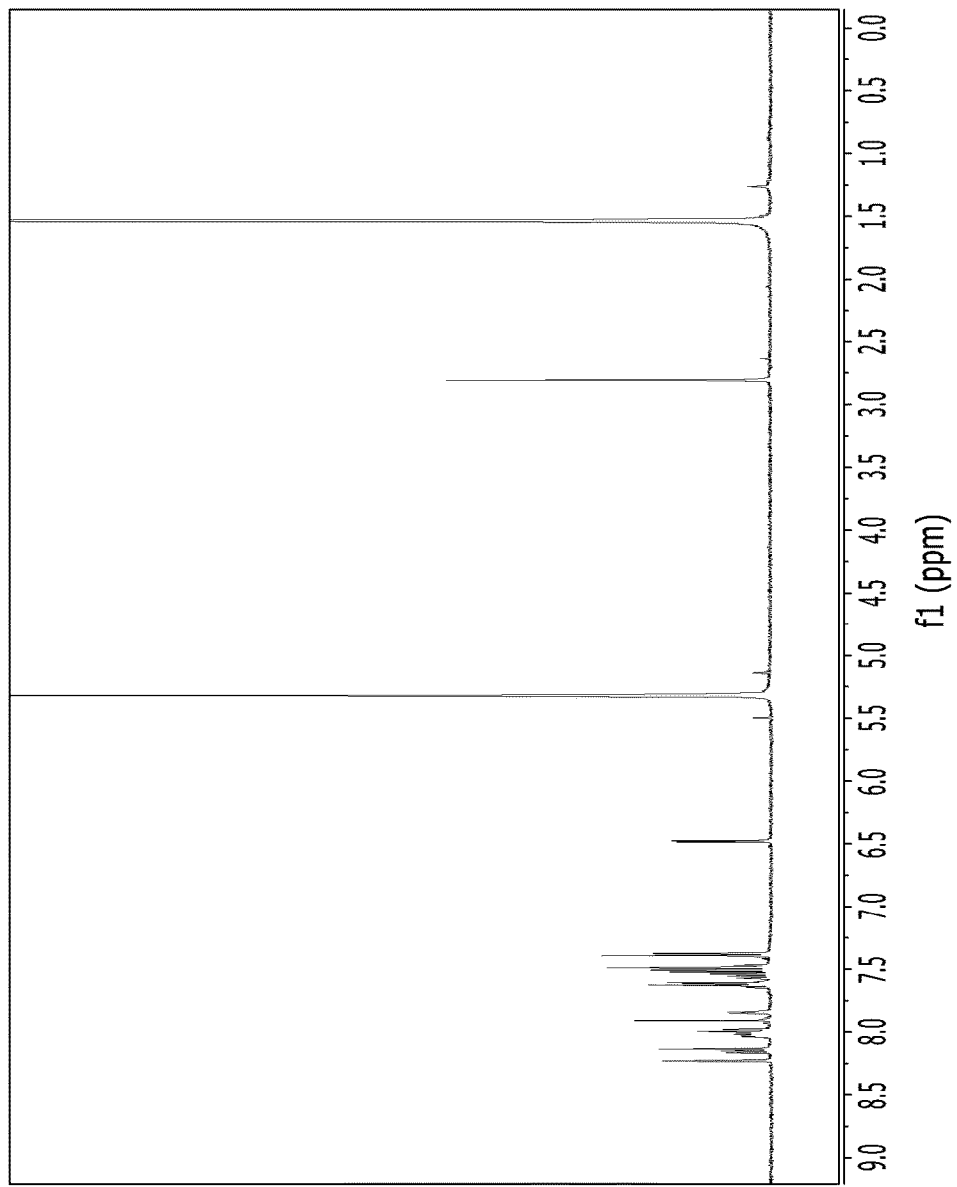

A compound represented by Chemical Formula 1-9 is synthesized according to the same method as Synthesis Example 1 except for using 5-((4-chlorophenyl) (4-methylnaphthalen-1-yl)amino)selenophene-2-carbaldehyde (1 mmol) instead of the compound 1a and using 1H-cyclopenta[b]naphthalene-1,3(2H)-dione (1 mmol) instead of the compound 1b. A yield is 90%. $^1$H-NMR (CD$_2$Cl$_2$, 300 MHz) of the compound represented by Chemical Formula 1-9 is shown in FIG. 16.

Synthesis Example 10: Synthesis of the Compound Represented by Chemical Formula 1-10 (2-((5-((3-methoxyphenyl)(4-methylnaphthalen-1-yl)amino)selenophen-2-yl)methylene)-1H-cyclopenta[b]naphthalene-1,3(2H)-dione)

[Chemical Formula 1-10]

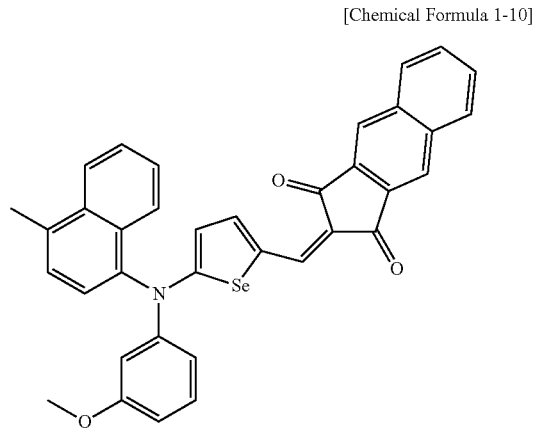 [SMILES: COc1cccc(N(c2ccc(C=C3C(=O)c4cc5ccccc5cc4C3=O)[se]2)c2ccc(C)c3ccccc23)c1]

Figure 17:
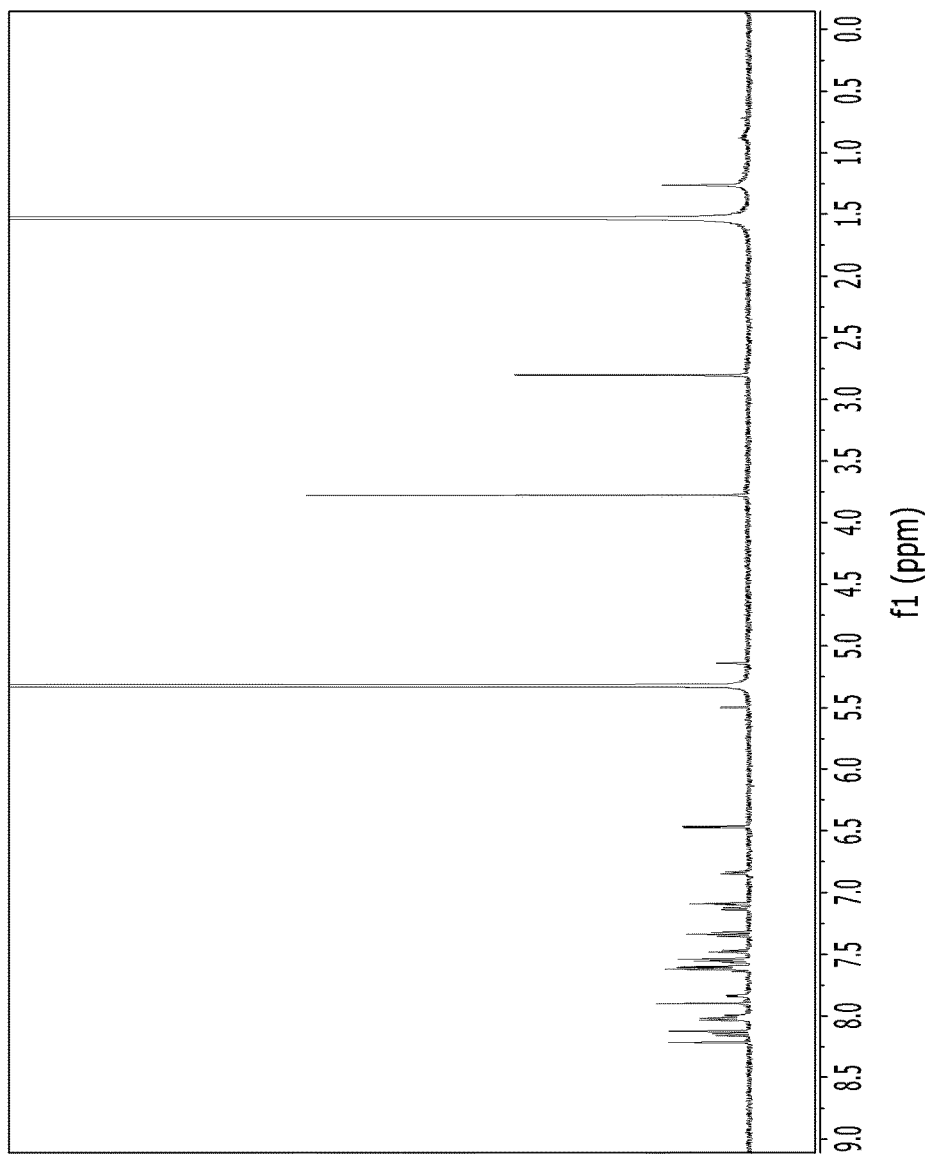
Figure 18:
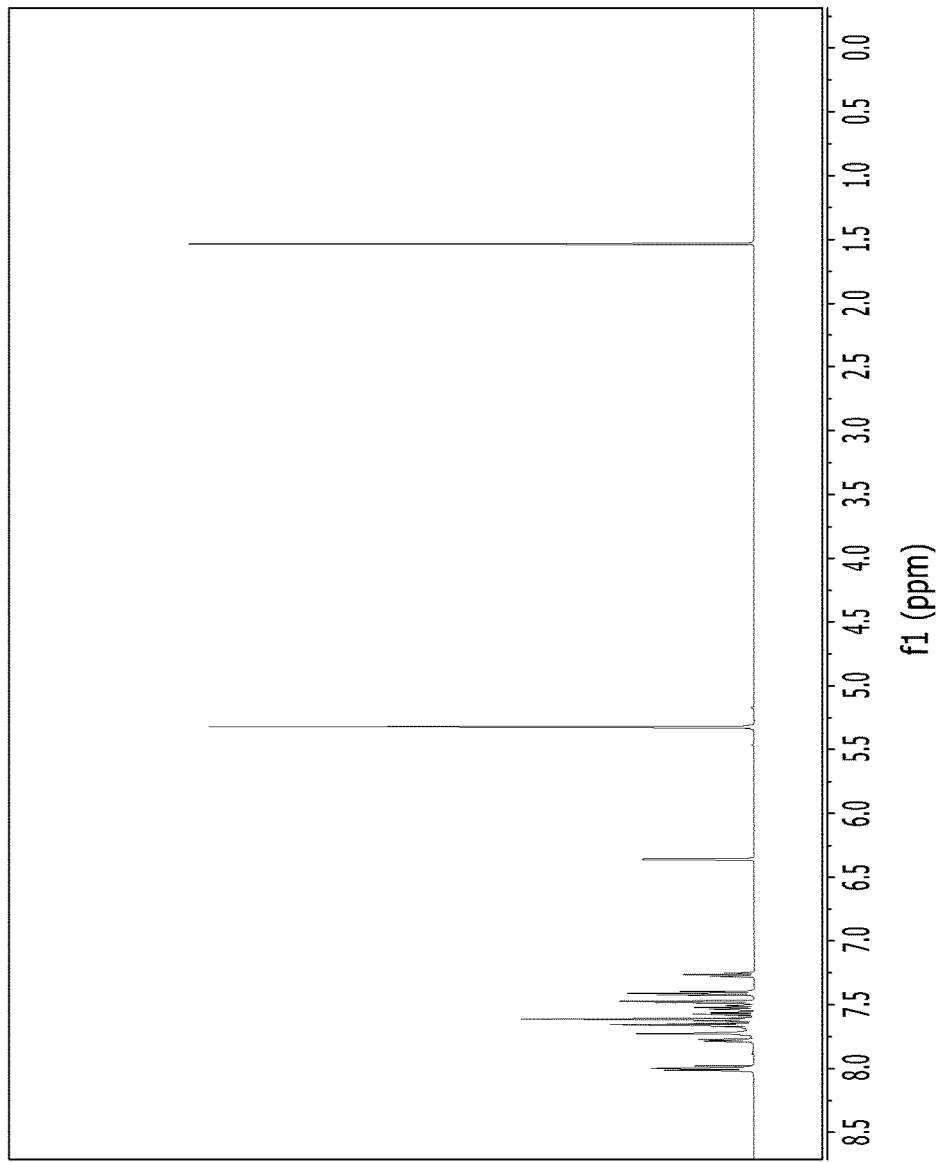
FIG. 18 is a graph showing a $^1$H-NMR result of the compound of Comparative Synthesis Example 1.

A compound represented by Chemical Formula 1-10 is synthesized according to the same method as Synthesis Example 1 except for using 5-((3-methoxyphenyl) (4-methylnaphthalen-1-yl)amino)selenophene-2-carbaldehyde (1 mmol) instead of the compound 1a and using 1H-cyclopenta[b]naphthalene-1,3(2H)-dione (1 mmol) instead of the compound 1b. A yield is 90%. $^1$H-NMR (CD$_2$Cl$_2$, 300 MHz) of the compound represented by Chemical Formula 1-10 is shown in FIG. 17.

Synthesis Example 11: Synthesis of the Compound Represented by Chemical Formula 1-11 (2-((5-(naphthalen-1-yl(phenyl)amino)tellurophen-2-yl)methylene)-1H-indene-1,3(2H)-dione)

[Chemical Formula 1-11]

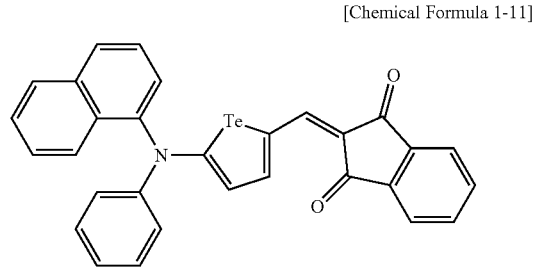

A compound represented by Chemical Formula 1-11 is synthesized according to the same method as Synthesis Example 1 except for using 5-(naphthalen-1-yl(phenyl) amino)tellurophene-2-carbaldehyde (1 mmol) instead of the compound 1a. A yield is 95%.

$^1$H-NMR (CDCl$_3$, 300 MHz): δ 8.32 (s, 1H), δ 8.07-8.02 (m, 2H), δ 7.92 (m, 2H), δ 7.60-7.53 (m, 5H), δ 7.38-7.20 (m, 3H), δ 6.98 (m, 1H), δ 6.81 (m, 1H), δ 6.70 (d, 1H), δ 6.29 (m, 2H), δ 6.15 (d, 1H). HRMS (ESI$^+$) Calculated for C$_{33}$H$_{20}$NO$_2$Te [M+H$^+$]: 556.0556 Found: 556.0555.

Synthesis Example 12: Synthesis of the Compound Represented by Chemical Formula 1-12 (2-((5-(naphthalen-1-yl(phenyl)amino)-1-oxidothiophen-2-yl)methylene)-1H-indene-1,3(2H)-dione)

[Chemical Formula 1-12]

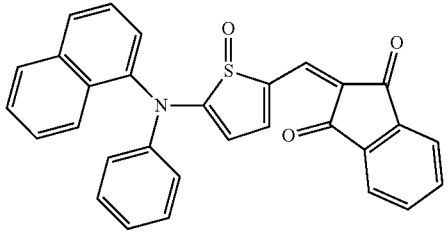

A compound represented by Chemical Formula 1-12 is synthesized according to the same method as Synthesis Example 1 except for using 5-(naphthalen-1-yl(phenyl)amino)thiophene-2-carbaldehyde 1-oxide (1 mmol) instead of the compound 1a. A yield is 90%.

$^1$H-NMR (CDCl$_3$, 300 MHz): δ 8.32 (s, 1H), δ 8.07-8.02 (m, 2H), δ 7.92 (m, 2H), δ 7.60-7.53 (m, 5H), δ 7.38-7.20 (m, 3H), δ 6.98 (m, 1H), δ 6.81 (m, 1H), δ 6.70 (d, 1H), δ 6.29 (m, 2H), δ 6.15 (d, 1H). HRMS (ESI$^+$) Calculated for C$_{30}$H$_{20}$NO$_3$S [M+H$^+$]: 474.1164 Found: 474.1165.

Synthesis Example 13: Synthesis of the Compound Represented by Chemical Formula 1-13 (2-((5-(naphthalen-1-yl(phenyl)amino)-1,1-dioxidothiophen-2-yl)methylene)-1H-indene-1,3(2H)-dione)

[Chemical Formula 1-13]

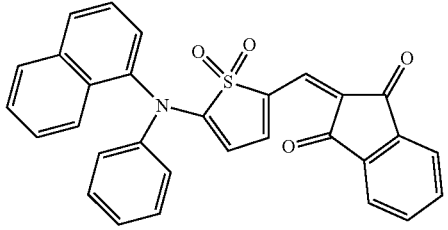

A compound represented by Chemical Formula 1-13 is synthesized according to the same method as Synthesis Example 1 except for using 5-(naphthalen-1-yl(phenyl) amino)thiophene-2-carbaldehyde 1,1-dioxide (1 mmol) instead of the compound 1a. A yield is 93%.

$^1$H-NMR (CDCl$_3$, 300 MHz): δ 8.32 (s, 1H), δ 8.07-8.02 (m, 2H), δ 7.92 (m, 2H), δ 7.60-7.53 (m, 5H), δ 7.43 (d, 1H), δ 7.38-7.20 (m, 3H), δ 6.98 (m, 1H), δ 6.88 (d, 1H), δ 6.81 (m, 1H), δ 6.29 (m, 2H). HRMS (ESI$^+$) Calculated for C$_{30}$H$_{20}$NO$_4$S [M+H$^+$]: 490.1113 Found: 490.1115.

Synthesis Example 14: Synthesis of the Compound Represented by Chemical Formula 1-14 (2-((5-(naphthalen-1-yl(phenyl)amino)-1H-silol-2-yl)methylene)-1H-indene-1,3(2H)-dione)

[Chemical Formula 1-14]

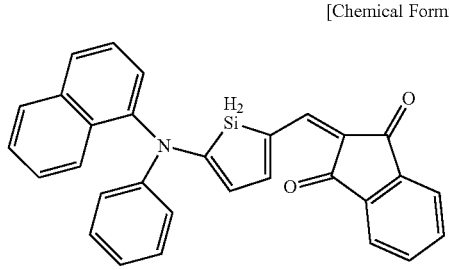

A compound represented by Chemical Formula 1-14 is synthesized according to the same method as Synthesis Example 1 except for using 5-(naphthalen-1-yl(phenyl)amino)-1H-silole-2-carbaldehyde (1 mmol) instead of the compound 1a. A yield is 90%.

$^1$H-NMR (CDCl$_3$, 300 MHz): δ 8.32 (s, 1H), δ 8.07-8.02 (m, 2H), δ 7.92 (m, 2H), δ 7.60-7.53 (m, 5H), δ 7.38-7.20 (m, 3H), δ 6.98 (m, 1H), δ 6.81 (m, 1H), δ 6.70 (d, 1H), δ 6.29 (m, 2H), δ 6.15 (d, 1H). HRMS (ESI$^+$) Calculated for C$_{30}$H$_{22}$NO$_2$Si [M+H$^+$]: 456.1420 Found: 456.1420.

Synthesis Example 15: Synthesis of the Compound Represented by Chemical Formula 1-15 (2-((1,1-dimethyl-5-(naphthalen-1-yl(phenyl)amino)-1H-silol-2-yl)methylene)-1H-indene-1,3(2H)-dione)

[Chemical Formula 1-15]

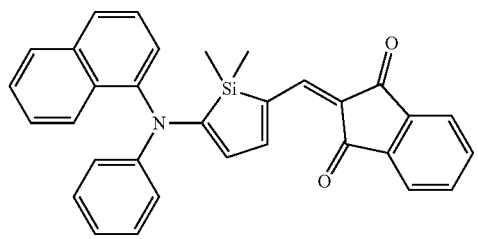

A compound represented by Chemical Formula 1-15 is synthesized according to the same method as Synthesis Example 1 except for using 1,1-dimethyl-5-(naphthalen-1-yl(phenyl)amino)-1H-silole-2-carbaldehyde (1 mmol) instead of the compound 1a. A yield is 70%.

$^1$H-NMR (CDCl$_3$, 300 MHz): δ 8.32 (s, 1H), δ 8.07-8.02 (m, 2H), δ 7.92 (m, 2H), δ 7.60-7.53 (m, 5H), δ 7.38-7.20 (m, 3H), δ 6.98 (m, 1H), δ 6.81 (m, 1H), δ 6.70 (m, 1H), δ 6.29 (m, 2H), δ 6.15 (d, 1H), δ 0.14 (s, 6H). HRMS (ESI) Calculated for C$_{32}$H$_{26}$NO$_2$Si [M+H$^+$]: 484.1733 Found: 484.1730.

Synthesis Example 16: Synthesis of the Compound Represented by Chemical Formula 1-16 ((E)-1,4-dimethyl-5-((5-(naphthalen-1-yl(phenyl)amino)selenophen-2-yl)methylene)-2,6-dioxo-1,2,5,6-tetrahydropyridine-3-carbonitrile)

[Chemical Formula 1-16]

[Reaction Scheme 1-16]

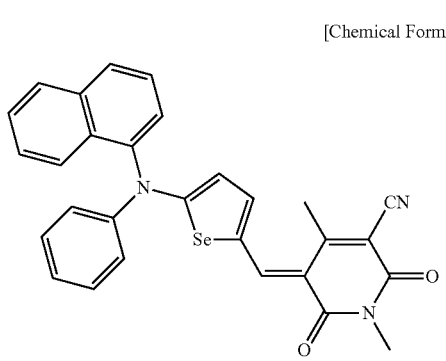

5-(naphthalen-1-yl(phenyl)amino)selenophene-2-carbaldehyde (a compound 1a, 1 mmol) and 6-hydroxy-1,4-dimethyl-2-oxo-1,2-dihydropyridine-3-carbonitrile (compound 2b, 1 mmol) are mixed with acetic anhydride (Ac$_2$O, 0.5 mL), and the mixture is stirred at 100° C. for 30 min. The stirred solution is cooled down to room temperature (24° C.), hexane is added to precipitate solids, and the solids are collected through vacuum-filtering. The collected solid is dissolved in dichloromethane and separated with a mixed solution of dichloromethane and ethyl acetate through silica gel column chromatography. After removing a solvent from the separated solution, the obtained solid is recrystallized in a mixed solution of dichloromethane and hexane, obtaining a compound represented by Chemical Formula 1-16. A yield is 75%.

$^1$H-NMR (CDCl$_3$, 300 MHz): δ 8.07-8.02 (m, 2H), δ 7.57-6.63 (m, 10H), δ 7.60 (d, 1H), δ 7.50 (s, 1H), δ 6.36 (d, 1H), δ 3.23 (s, 3H), δ 2.21 (s, 3H).

Comparative Synthesis Example 1: Synthesis of the Compound Represented by Chemical Formula 1-17 (2-((5-(naphthalen-1-yl(phenyl)amino)thiophen-2-yl)methylene)-1H-indene-1,3(2H)-dione)

[Chemical Formula 1-17]

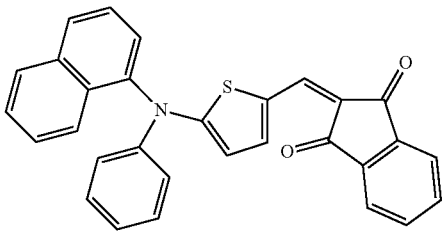

A compound represented by Chemical Formula 1-17 is synthesized according to the same method as Synthesis Example 1 except for using 5-(naphthalen-1-yl(phenyl)amino)thiophene-2-carbaldehyde (1 mmol) instead of the compound 1a. A yield is 80%. $^1$H-NMR (CD$_2$Cl$_2$, 600 MHz) of the compound represented by Chemical Formula 1-17 is shown in FIG. 17.

Comparative Synthesis Example 2: Synthesis of the Compound Represented by Chemical Formula 1-18 (2-((5-(piperidin-1-yl)selenophen-2-yl)methylene)-1H-indene-1,3(2H)-dione)

[Chemical Formula 1-18]

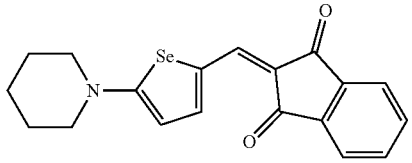

A compound represented by Chemical Formula 1-18 is synthesized according to the same method as Synthesis Example 1 except for using 5-(piperidin-1-yl)selenophene-2-carbaldehyde (1 mmol) instead of the compound 1a. A yield is 75%.

$^1$H-NMR (CDCl$_3$, 300 MHz): δ 8.32 (s, 1H), δ 7.92 (m, 2H), δ 7.60 (m, 2H), δ 7.14 (d, 1H), δ 5.86 (d, 1H), δ 3.17 (m, 4H), δ 1.59-1.53 (m, 6H).

Light Absorption Characteristics of Compounds of Synthesis Examples 1 to 16 and Comparative Synthesis Examples 1 and 2

Light absorption characteristics depending on a wavelength of the compounds according to Synthesis Examples 1 to 16 and Comparative Synthesis Examples 1 and 2 are evaluated. Light absorption characteristics in a solution state and in a thin film state are evaluated.

Light absorption characteristics in a solution state are evaluated using each solution obtained by dissolving the compounds of Synthesis Examples 1 to 16 and Comparative Synthesis Examples 1 and 2 in dichloromethane with 1.0× 10$^{-5}$ mol/L.

Light absorption characteristics in a thin film state are evaluated by thermally depositing each compounds of Synthesis Examples 1 to 16 and Comparative Synthesis Examples 1 and 2 under high vacuum (<10$^{-7}$ Torr) at 0.5-1.0 Å/s to respectively form a 70 nm-thick thin film and radiating ultraviolet (UV)-visible rays (UV-Vis) thereinto with Cary 5000 UV spectrometer (Varian Inc.). The results are shown in the following Table 1.

Thermal Stability of Compounds of Synthesis Examples 1 to 16 and Comparative Synthesis Examples 1 and 2

Thermal stability of the compounds of Synthesis Examples 1 to 16 and Comparative Synthesis Examples 1 and 2 are evaluated by measuring their thermal decomposition temperatures. The thermal decomposition temperature (T$_d$) is a temperature at which a compound starts to be decomposed and thus, does not maintain its intrinsic molecular structure but is transformed. In general, atoms in a molecule consisting of a compound are volatilized and lost into the air or vacuum at greater than or equal to a thermal decomposition temperature, and thus, the thermal decomposition temperature may be regarded as a temperature at which initial weight of the compound starts to be decreased by heat. Herein, a thermal gravimetric analysis (TGA) method is used to measure the thermal decomposition temperature. The results are shown in the following Table 1.

TABLE 1

| | λ$_{max}$ (nm) | | FWHM (nm) | | Energy level (film) | | |
|---|---|---|---|---|---|---|---|
| | Solution | Thin film | Solution | Thin film | HOMO (eV) | LUMO (eV) | T$_d$ (° C.) |
| Synthesis Example 1 | 528 | 538 | 47 | 88 | 5.28 | 3.17 | 291 |
| Synthesis Example 2 | 530 | 545 | 46 | 87 | 5.23 | 3.10 | 317 |
| Synthesis Example 3 | 553 | 563 | 47 | 88 | 5.52 | 3.57 | 346 |

TABLE 1-continued

|  | $\lambda_{max}$ (nm) | | FWHM (nm) | | Energy level (film) | | |
| --- | --- | --- | --- | --- | --- | --- | --- |
|  | Solution | Thin film | Solution | Thin film | HOMO (eV) | LUMO (eV) | $T_d$ (° C.) |
| Synthesis Example 4 | 555 | 569 | 46 | 87 | 5.48 | 3.54 | 318 |
| Synthesis Example 5 | 560 | 573 | 45 | 86 | 5.42 | 3.50 | 359 |
| Synthesis Example 6 | 548 | 560 | 46 | 87 | 5.66 | 3.68 | 338 |
| Synthesis Example 7 | 550 | 564 | 45 | 86 | 5.62 | 3.65 | 345 |
| Synthesis Example 8 | 550 | 560 | 46 | 87 | 5.63 | 3.67 | 349 |
| Synthesis Example 9 | 552 | 564 | 45 | 86 | 5.59 | 3.64 | 355 |
| Synthesis Example 10 | 560 | 573 | 44 | 85 | 5.44 | 3.50 | 346 |
| Synthesis Example 11 | 530 | 540 | 48 | 85 | 5.30 | 3.19 | 295 |
| Synthesis Example 12 | 539 | 549 | 45 | 88 | 5.56 | 3.47 | 295 |
| Synthesis Example 13 | 545 | 555 | 47 | 86 | 5.71 | 3.64 | 296 |
| Synthesis Example 14 | 522 | 532 | 48 | 87 | 5.14 | 3.06 | 305 |
| Synthesis Example 15 | 525 | 534 | 47 | 88 | 5.10 | 3.02 | 310 |
| Synthesis Example 16 | 557 | 570 | 47 | 95 | 5.55 | 3.56 | 285 |
| Comparative Synthesis Example 1 | 517 | 526 | 48 | 89 | 5.36 | 3.24 | 266 |
| Comparative Synthesis Example 2 | 520 | 475 | 25 | 126 | 5.02 | 2.96 | 285 |

Referring to Table 1, the compounds of Synthesis Examples 1 to 16 show a maximum absorption wavelength in a green wavelength region (e.g., greater than 530 nm and less than or equal to 575 nm) and a narrower full width at half maximum (FWHM) than the compounds of Comparative Synthesis Examples 1 and 2. In particular, the compound of Comparative Synthesis Example 2 shows a narrow full width at half maximum (FWHM) in a solution state but a wider full width at half maximum (FWHM) in a thin film, since the molecules of the compound are aggregation due to structural planarity of the thin film. Accordingly, the compounds of Synthesis Examples 1 to 16 show improved green wavelength selectivity compared with the compounds of Comparative Synthesis Examples 1 and 2.

Referring to Table 1, the compounds of Synthesis Examples 1 to 16 and Comparative Synthesis Examples 1 and 2 have a difference between HOMO and LUMO energy levels of about 2.0 eV or so in thin film state and thus, a similar energy bandgap.

The compounds of Synthesis Examples 1 to 16 has greater than or equal to 5.10 eV of a HOMO energy level in a thin film state and thus, may realize very high photoelectric conversion efficiency compared with the compound of Comparative Synthesis Example 2 having a relatively low HOMO energy level of 5.02 eV in a thin film state. In particular, the compounds of Synthesis Examples 12 and 13 more easily transport separated holes into neighboring charge auxiliary layers 40 and 45 having a HOMO energy level of 5.5 eV or so and thus, may increase photoelectric conversion efficiency. The compounds of Synthesis Examples 12 and 13 may realize higher photoelectric conversion efficiency due to these characteristics when the charge auxiliary layers 40 and 45 are additionally used for an organic photoelectric device.

In addition, the compounds of Synthesis Examples 1, 11, 14 and 15 have a lower LUMO energy level in a thin film state than the compound of Comparative Synthesis Example 1 and more easily cut off injection of electrons applied from the outside and improve dark current characteristics.

Furthermore, the compounds of Synthesis Examples 1 to 16 show a relatively high thermal degradation temperature compared with the compounds of Comparative Synthesis Examples 1 and 2 and thus, desirable thermal stability.

Example 1: Manufacture of Organic Photoelectric Device

An about 150 nm-thick anode is formed by sputtering ITO on a glass substrate, and a 85 nm-thick active layer is formed by codepositing the compound of Synthesis Example 1 (a p-type semiconductor compound) and C60 (an n-type semiconductor compound) in a thickness ratio of 1:1 thereon. Subsequently, a 30 nm-thick molybdenum oxide ($MoO_x$, $0<x\leq3$) thin film is laminated as a charge auxiliary layer thereon. Then, an 80 nm-thick cathode is formed by sputtering ITO on the molybdenum oxide thin film, manufacturing an organic photoelectric device.

Examples 2 to 16: Manufacture of Organic Photoelectric Device

Each organic photoelectric device according to Examples 2 to 16 is manufactured according to the same method as Example 1, except for using each compound according to Synthesis Examples 2 to 16, instead of the compound of the Synthesis Example 1.

External Quantum Efficiency (EQE) of Organic Photoelectric Device of Examples 1 to 16

External quantum efficiency (EQE) of the organic photoelectric devices according to Examples 1 to 16 depending on wavelength and voltage is evaluated.

The external quantum efficiency is measured by using an IPCE measurement system (McScience Co., Ltd. Korea). First of all, the IPCE measurement system is calibrated by using a Si photodiode (Hamamatsu Photonics K.K., Japan), the organic photoelectric devices of Examples 1 to 16 are then respectively mounted thereon, and their external quantum efficiency in a wavelength region of about 350 to about 750 nm is determined. Of these, the external quantum efficiency of the organic photoelectric device according to Example 1 is shown in FIGS. 19 and 20.

Figure 19:
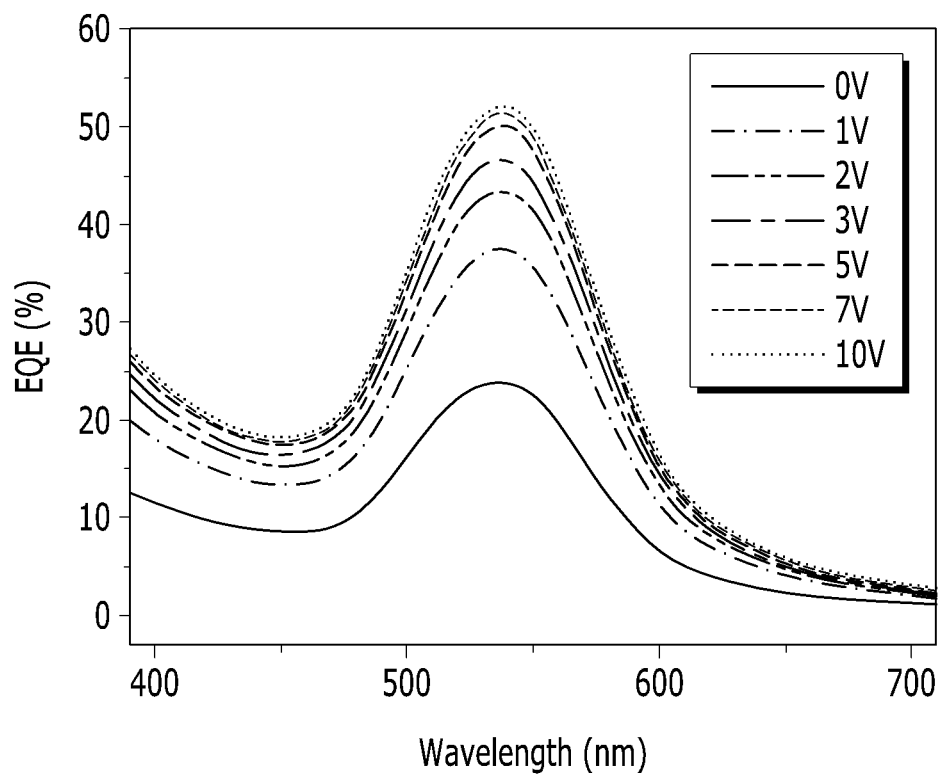
FIG. 19 shows external quantum efficiency (EQE) depending on a voltage of the organic photoelectric device of Example 1.
Figure 20:
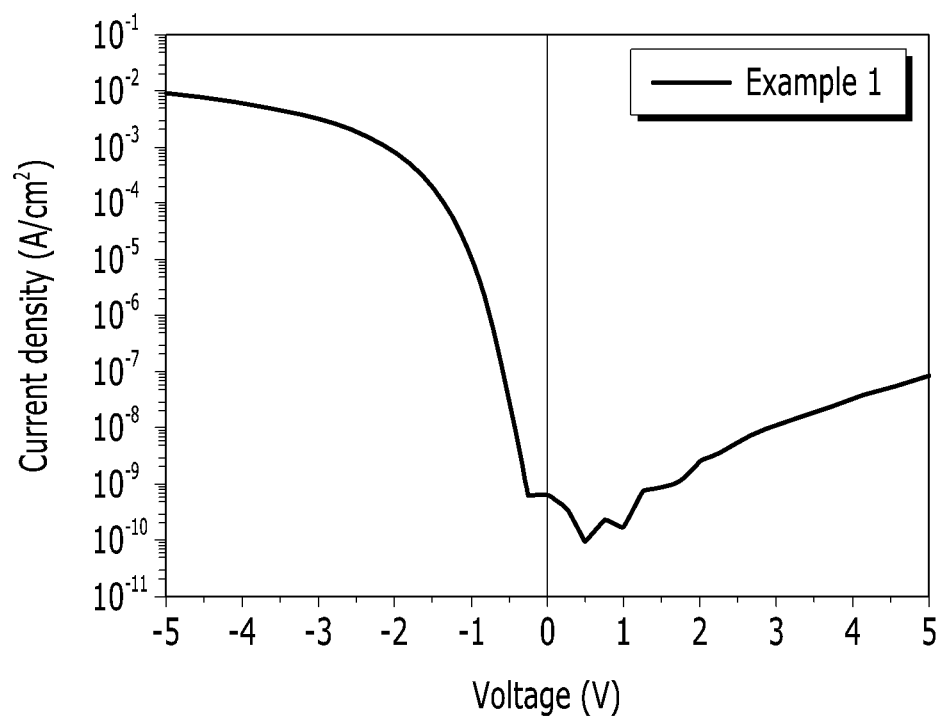
FIG. 20 shows voltage-current characteristics of the organic photoelectric device of Example 1.

FIG. 19 shows external quantum efficiency (EQE) depending on a voltage of the organic photoelectric device of Example 1, and FIG. 20 shows voltage-current characteristics of the organic photoelectric device of Example 1.

Referring to FIGS. 19 and 20, the organic photoelectric device of Example 1 shows desirable external quantum efficiency (EQE) in a green wavelength region of about 500 nm to 600 nm Examples 17 to 26: Manufacture of Organic Photoelectric Device An about 150 nm-thick anode is formed by sputtering ITO on a glass substrate, and an active layer is formed by depositing each compound (p-type semiconductor compound) of Table 2 and C60 (n-type semiconductor compound) in a thickness ratio of 1:1 thereon. The active layer is formed with each thickness of Table 2. Subsequently, a 30 nm-thick molybdenum oxide ($MoO_x$, $0<x\leq3$) thin film is laminated as a charge auxiliary layer thereon. Then, an 80 nm-thick cathode is formed by sputtering ITO on the molybdenum oxide thin film, manufacturing an organic photoelectric device.

Comparative Examples 1 and 2: Manufacture of Organic Photoelectric Device

Each organic photoelectric device according to Comparative Examples 1 and 2 is manufactured according to the same method as Examples 17 to 26, except for using the compounds represented by Chemical Formula 1-17 according to Comparative Synthesis Example 1 and Chemical Formula 1-18 according to Comparative Synthesis Example 2, instead of the compound represented by Chemical Formula 1-1 of the Synthesis Example 1.

External quantum efficiency, maximum absorption wavelengths, dark currents and heat resistance of the organic photoelectric devices according to Examples 17 to 26 and Comparative Examples 1 and 2 are evaluated as follows and the results are shown in Table 2.

The external quantum efficiency is measured by using an IPCE measurement system (McScience Co., Ltd. Korea). First of all, the IPCE measurement system is calibrated by using a Si photodiode (Hamamatsu Photonics K.K., Japan), the organic photoelectric devices of Examples 17 to 26 and Comparative Example 1 and 2 are then respectively mounted thereon, and their external quantum efficiency in a wavelength region of about 350 to about 750 nm is determined. The organic photoelectric devices are driven at 160° C. and a time when external quantum efficiency is reduced to less than 95% from an initial value, 100% is measured in order to evaluate heat resistance.

TABLE 2

| Example Nos. (Chemical Formula Nos.) | Thickness of active layer (nm) | $EQE_{max}$ @ 3 V (%) | $\lambda$ max (nm) | DC @ 3 V (e/s/$\mu m^2$) | Heat resistance |
|---|---|---|---|---|---|
| Example 17 (Chemical Formula 1-1) | 170 | 66 | 540 | 10 | 3 hrs |
| Example 18 (Chemical Formula 1-2) | 160 | 66 | 540 | 60 | 3 hrs |
| Example 19 (Chemical Formula 1-3) | 120 | 70 | 560 | 23 | 3 hrs |
| Example 20 (Chemical Formula 1-4) | 160 | 73 | 570 | 44 | 3 hrs |
| Example 21 (Chemical Formula 1-5) | 120 | 59 | 570 | 25 | 3 hrs |
| Example 22 (Chemical Formula 1-6) | 120 | 61 | 560 | 21 | 3 hrs |
| Example 23 (Chemical Formula 1-7) | 120 | 65 | 560 | 70 | 3 hrs |
| Example 24 (Chemical Formula 1-8) | 150 | 72 | 560 | 4 | 3 hrs |
| Example 25 (Chemical Formula 1-9) | 120 | 71 | 560 | 13 | 3 hrs |
| Example 26 (Chemical Formula 1-10) | 140 | 67 | 560 | 8 | 3 hrs |
| Comparative Example 1 (Chemical Formula 1-17) | 140 | 57 | 530 | 180 | <1 hr |

As shown in Table 2, the organic photoelectric devices according to Example 17 to 26 showed improved external quantum efficiency, a maximum absorption wavelength in a green wavelength region, reduced dark current, and improved heat resistance, compared with the organic photoelectric device according to Comparative Example 1.

Thermal Stability of Organic Photoelectric Device

Figure 21:
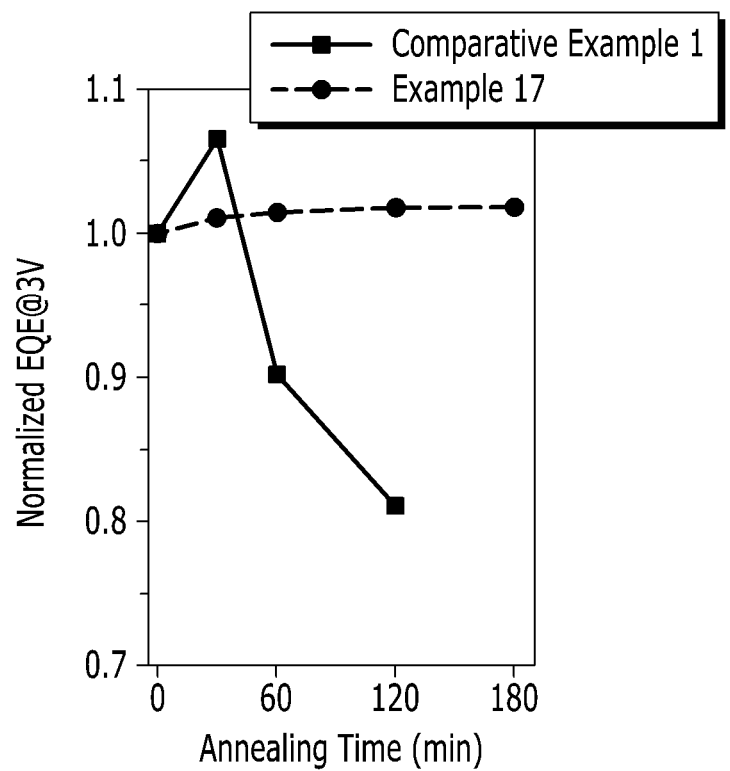
FIG. 21 shows external quantum efficiency (EQE) depending on a heat treatment time of the organic photoelectric devices according to Example 17 and Comparative Example 1.
Figure 22:
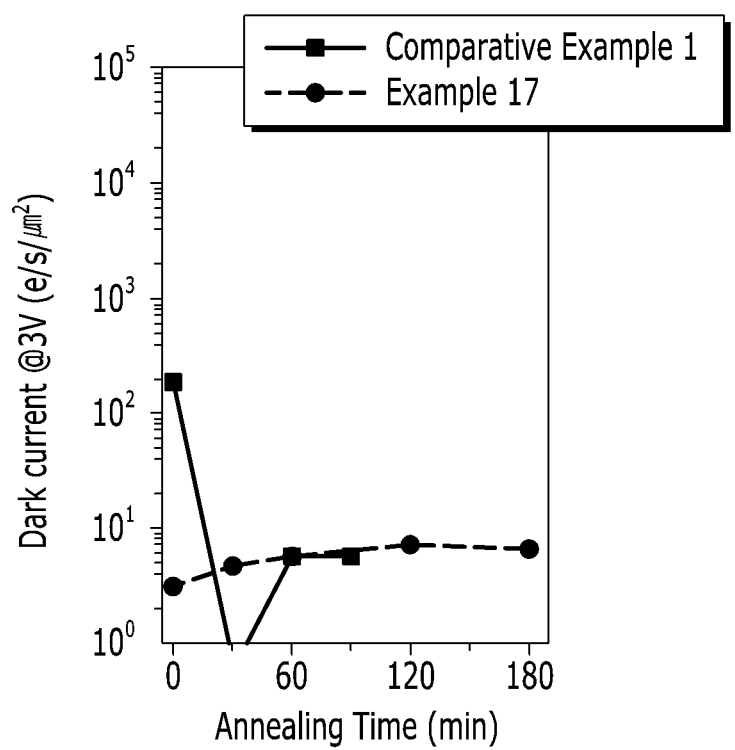
FIG. 22 shows dark current (DC) depending on a heat treatment time of the organic photoelectric devices according to Example 17 and Comparative Example 1.

The organic photoelectric devices according to Examples 17 to 26 and Comparative Examples 1 and 2 are heat-treated at 160° C. and external quantum efficiency and dark currents (DC) at 3 V depending on a heat treatment time are measured. The results of the external quantum efficiency and dark currents (DC) of the organic photoelectric devices according to Example 17 and Comparative Example 1 depending on a heat treatment time are shown in FIGS. 21 and 22, respectively. FIG. 21 shows external quantum efficiency (EQE) depending on a heat treatment time of the organic photoelectric devices according to Example 17 and Comparative Example 1, and FIG. 22 shows dark current (DC) depending on a heat treatment time of the organic photoelectric devices according to Example 17 and Comparative Example 1. Referring to FIG. 21, the organic photoelectric device according to Example 17 shows slight changes of external quantum efficiency depending on a heat treatment time but the organic photoelectric device according to Comparative Example 1 shows that external quantum efficiency increases at 30 min but remarkably decreases at 60 min. Referring to FIG. 22, the organic photoelectric device according to Example 17 shows relatively few or no changes to a dark current by heat treatment and the organic photoelectric device according to Comparative Example 1 shows relatively large changes to a dark current as a heat treatment time continues. From the results, the organic photoelectric device according to Example 17 has improved thermal stability compared with the organic photoelectric device according to Comparative Example 1, and is more desirable for a heat treatment process that may be a subsequent process during manufacture of a device.

While this disclosure has been described in connection with what is presently considered to be practical example embodiments, it is to be understood that the inventive concepts are not limited to the disclosed embodiments, but, on the contrary, is intended to cover various modifications and equivalent arrangements included within the spirit and scope of the appended claims.

What is claimed is:

1. A compound for an organic photoelectric device represented by Chemical Formula 1:

[Chemical Formula 1]

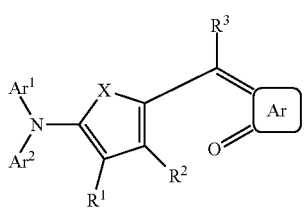

wherein, in Chemical Formula 1,

Ar is one of a substituted or unsubstituted 5-membered ring, a substituted or unsubstituted 6-membered ring, and a condensed ring of two or more of the foregoing rings, X is one of Se, Te, S(=O), S(=O)$_2$, and SiR$^a$R$^b$, wherein each of R$^a$ and R$^b$ are independently one of hydrogen and a substituted or unsubstituted C$_1$ to C$_{10}$ alkyl group, each of Ar$^1$ and Ar$^2$ are independently one of a substituted or unsubstituted C$_6$ to C$_{30}$ aryl group and a substituted or unsubstituted C$_3$ to C$_{30}$ heteroaryl group, and each of R$^1$ to R$^3$ are independently one of hydrogen, a substituted or unsubstituted C$_1$ to C$_{30}$ alkyl group, a substituted or unsubstituted C$_6$ to C$_{30}$ aryl group, a substituted or unsubstituted C$_3$ to C$_{30}$ heteroaryl group, a halogen, a cyano group (—CN), a cyano-containing group, and a combination thereof wherein the compound has a maximum absorption wavelength ($\lambda_{max}$) in a wavelength region of greater than about 530 nm and less than or equal to about 575 nm.

2. The compound of claim 1, wherein the compound has 4 to 7 aromatic rings.

3. The compound of claim 1, wherein at least one of the Ar$^1$ and Ar$^2$ groups is one of a substituted or unsubstituted naphthyl group, a substituted or unsubstituted anthracenyl group, and a substituted or unsubstituted phenanthrenyl group.

4. The compound of claim 1, wherein in Chemical Formula 1, a cyclic group represented by Ar and bound to a methine group is represented by Chemical Formula 2:

[Chemical Formula 2]

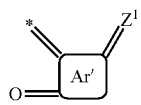

wherein, in Chemical Formula 2,

Ar' is one of a substituted or unsubstituted 5-membered ring, a substituted or unsubstituted 6-membered ring, and a condensed ring of two or more of the foregoing rings, and Z$^1$ is one of O and CR$^c$R$^d$, wherein each of R$^c$ and R$^d$ are independently one of hydrogen, a substituted or unsubstituted C$_1$ to C$_{10}$ alkyl group, a cyano group, and a cyano-containing group, provided at least one of R$^c$ and R$^d$ is one of a cyano group and a cyano-containing group.

5. The compound of claim 1, wherein in Chemical Formula 1, a cyclic group represented by Ar and bound to a methine group is a cyclic group represented by one of Chemical Formulae 3-1 to 3-3:

[Chemical Formula 3-1]

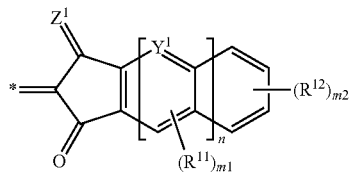

[Chemical Formula 3-2]

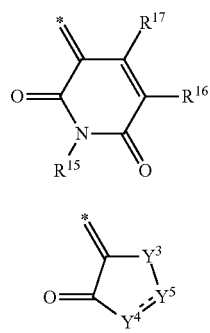

[Chemical Formula 3-3]

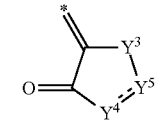

wherein, in Chemical Formulae 3-1 to 3-3,

Z$^1$ is one of O and CR$^c$R$^d$, wherein each of R$^c$ and R$^d$ are independently one of hydrogen, a substituted or unsubstituted C$_1$ to C$_{10}$ alkyl group, a cyano group, and a cyano-containing group, provided at least one of R$^c$ and R$^d$ is one of a cyano group and a cyano-containing group, Y$^1$ is one of N and CR$^e$, wherein R$^e$ is one of hydrogen and a substituted or unsubstituted C$_1$ to C$_{10}$ alkyl group, Y$^3$ is one of O, S, Se, and Te, Y$^4$ is one of N and NR$^{18}$, Y$^5$ is one of CR$^{19}$ and C=C(R$^{20}$)(CN), each of R$^{11}$, R$^{12}$ and R$^{15}$ to R$^{20}$ are independently one of hydrogen, a substituted or unsubstituted C$_1$ to C$_{30}$ alkyl group, a substituted or unsubstituted C$_6$ to C$_{30}$ aryl group, a substituted or unsubstituted C$_4$ to C$_{30}$ heteroaryl group, a halogen, a cyano group (—CN), a cyano-containing group and a combination thereof, m1 is 0 or 1, m2 is an integer ranging from 0 to 4, and n is 0 or 1.

6. The compound of claim 1, wherein the compound is represented by one of Chemical Formulae 4-1 to 4-3:

[Chemical Formula 4-1]

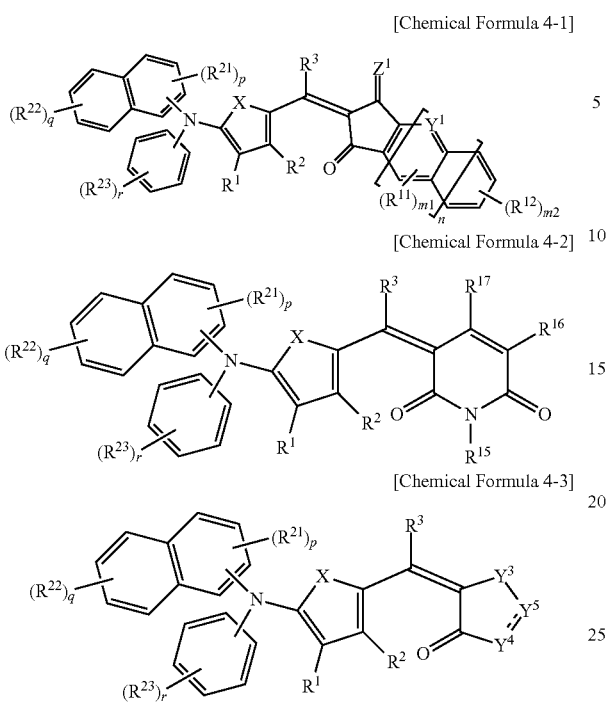

[Chemical Formula 4-2]

[Chemical Formula 4-3]

wherein, in Chemical Formulae 4-1 to 4-3,

X is one of Se, Te, S(=O), S(=O)$_2$, and SiR$^a$R$^b$ wherein each of R$^a$ and R$^b$ are independently one of hydrogen and a substituted or unsubstituted C$_1$ to C$_{10}$ alkyl group, Z$^1$ is one of O and CR$^c$R$^d$ wherein R$^c$ and R$^d$ are independently one of hydrogen, a substituted or unsubstituted C$_1$ to C$_{10}$ alkyl group, a cyano group, and a cyano-containing group, provided at least one of R$^c$ and R$^d$ is one of a cyano group and a cyano-containing group, Y$^1$ is one of N and CR$^e$ wherein R$^e$ is one of hydrogen and a substituted or unsubstituted C$_1$ to C$_{10}$ alkyl group, Y$^3$ is one of O, S, Se, and Te, Y$^4$ is one of N and NR$^{18}$, Y$^5$ is one of CR$^{19}$ and C=C(R$^{20}$)(CN), each of R$^1$ to R$^3$, R$^{11}$, R$^{12}$ and R$^{15}$ to R$^{20}$ are independently one of hydrogen, a substituted or unsubstituted C$_1$ to C$_{30}$ alkyl group, a substituted or unsubstituted C$_6$ to C$_{30}$ aryl group, a substituted or unsubstituted C$_4$ to C$_{30}$ heteroaryl group, a halogen, a cyano group (—CN), a cyano-containing group and combination thereof, m1 is 0 or 1, m2 is an integer ranging from 0 to 4, n is 0 or 1, each of R$^{21}$ to R$^{23}$ are independently one of hydrogen, a halogen, a cyano group (—CN), a cyano-containing group, a substituted or unsubstituted C$_1$ to C$_6$ alkyl group, a substituted or unsubstituted C$_1$ to C$_6$ alkoxy group, and a combination thereof, and p is an integer ranging from 0 to 3, q is an integer ranging from 0 to 4, and r is an integer ranging from 0 to 5.

7. The compound of claim 1, wherein the compound shows a light absorption curve having a full width at half maximum (FWHM) of about 50 nm to about 110 nm in a thin film state.

8. The compound of claim 1, wherein the compound has a thermal decomposition of greater than or equal to about 280° C.

9. An organic photoelectric device comprising:
a first electrode and a second electrode facing each other; and
an active layer between the first electrode and the second electrode, the active layer including a compound represented by Chemical Formula 1:

[Chemical Formula 1]

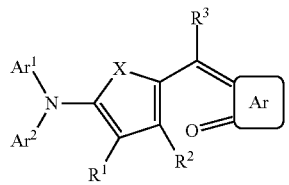

wherein, in Chemical Formula 1,

Ar is one of a substituted or unsubstituted 5-membered ring, a substituted or unsubstituted 6-membered ring, and a condensed ring of two or more of the foregoing rings, X is one of Se, Te, S(=O), S(=O)$_2$, and SiR$^a$R$^b$, wherein R$^a$ and R$^b$ are independently one of hydrogen and a substituted or unsubstituted C$_1$ to C$_{10}$ alkyl group, each of Ar$^1$ and Ar$^2$ are independently one of a substituted or unsubstituted C$_6$ to C$_{30}$ aryl group and a substituted or unsubstituted C$_3$ to C$_{30}$ heteroaryl group, and each of R$^1$ to R$^3$ are independently one of hydrogen, a substituted or unsubstituted C$_1$ to C$_{30}$ alkyl group, a substituted or unsubstituted C$_6$ to C$_{30}$ aryl group, a substituted or unsubstituted C$_3$ to C$_{30}$ heteroaryl group, a halogen, a cyano group (—CN), a cyano-containing group, and a combination thereof, wherein the compound has a maximum absorption wavelength ($\lambda_{max}$) in a wavelength region of greater than about 530 nm and less than or equal to about 575 nm.

10. The organic photoelectric device of claim 9, wherein the compound has 4 to 7 aromatic rings.

11. The organic photoelectric device of claim 9, wherein at least one of the Ar$^1$ and Ar$^2$ groups is one of a substituted or unsubstituted naphthyl group, a substituted or unsubstituted anthracenyl group, and a substituted or unsubstituted phenanthrenyl group.

12. The organic photoelectric device of claim 9, wherein in Chemical Formula 1, a cyclic group represented by Ar and bound to a methine group is represented by Chemical Formula 2:

[Chemical Formula 2]

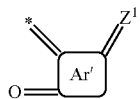

wherein, in Chemical Formula 2,

Ar' is one of a substituted or unsubstituted 5-membered ring, a substituted or unsubstituted 6-membered ring, and a condensed ring of two or more of the foregoing rings, and Z$^1$ is one of O and CR$^c$R$^d$, wherein each of R$^c$ and R$^d$ are independently one of hydrogen, a substituted or unsubstituted C$_1$ to C$_{10}$ alkyl group, a cyano group, and a cyano-containing group, provided at least one of R$^c$ and R$^d$ is one of a cyano group and a cyano-containing group.

13. The organic photoelectric device of claim 9, wherein in Chemical Formula 1, a cyclic group represented by Ar and bound to a methine group is a cyclic group represented by one of Chemical Formulae 3-1 to 3-3:

[Chemical Formula 3-1]
[Chemical Formula 3-2]
[Chemical Formula 3-3]

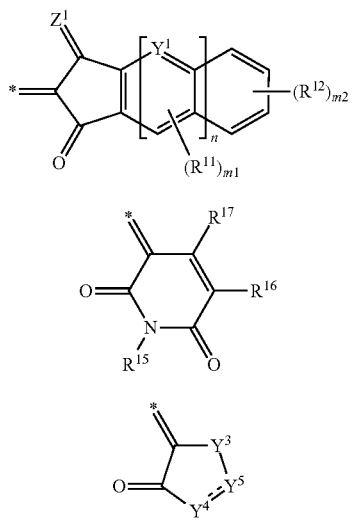

wherein, in Chemical Formulae 3-1 to 3-3, $Z^1$ is one of O and $CR^cR^d$, wherein $R^c$ and $R^d$ are independently one of hydrogen, a substituted or unsubstituted $C_1$ to $C_{10}$ alkyl group, a cyano group, and a cyano-containing group, provided at least one of $R^c$ and $R^d$ is one of a cyano group and a cyano-containing group, $Y^1$ is one of N and $CR^e$, wherein $R^e$ is one of hydrogen and a substituted or unsubstituted $C_1$ to $C_{10}$ alkyl group, $Y^3$ is one of O, S, Se, and Te, $Y^4$ is one of N and $NR^{18}$, $Y^5$ is one of $CR^{19}$ and $C=C(R^{20})(CN)$, each of $R^{11}$, $R^{12}$ and $R^{15}$ to $R^{20}$ are independently one of hydrogen, a substituted or unsubstituted $C_1$ to $C_{30}$ alkyl group, a substituted or unsubstituted $C_6$ to $C_{30}$ aryl group, a substituted or unsubstituted $C_4$ to $C_{30}$ heteroaryl group, a halogen, a cyano group (—CN), a cyano-containing group, and a combination thereof, m1 is 0 or 1, m2 is an integer ranging from 0 to 4, and n is 0 or 1.

14. The organic photoelectric device of claim 9, wherein the compound is represented by one of Chemical Formulae 4-1 to 4-3:

[Chemical Formula 4-1]

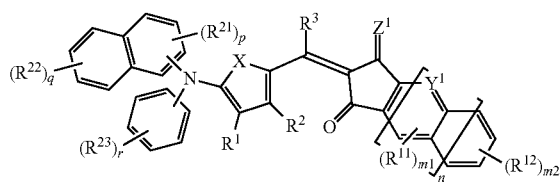

[Chemical Formula 4-2]

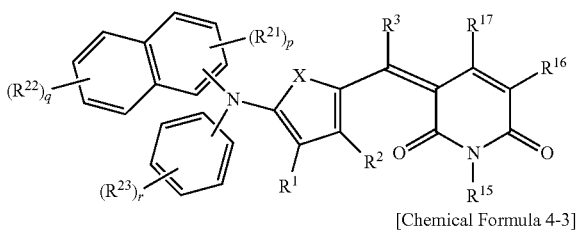

[Chemical Formula 4-3]

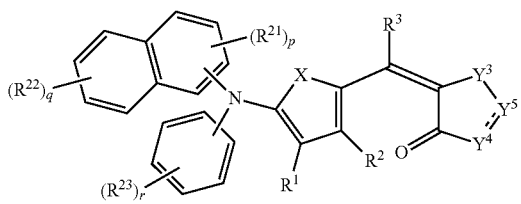

wherein, in Chemical Formulae 4-1 to 4-3,

X is one of Se, Te, S(=O), S(=O)$_2$, and $SiR^aR^b$, wherein each of $R^a$ and $R^b$ are independently one of hydrogen and a substituted or unsubstituted $C_1$ to $C_{10}$ alkyl group, $Z^1$ is one of O and $CR^cR^d$, wherein each of $R^c$ and $R^d$ are independently one of hydrogen, a substituted or unsubstituted $C_1$ to $C_{10}$ alkyl group, a cyano group, and a cyano-containing group, provided at least one of $R^c$ and $R^d$ is one of a cyano group and a cyano-containing group, $Y^1$ is one of N and $CR^e$, wherein $R^e$ is one of hydrogen and a substituted or unsubstituted $C_1$ to $C_{10}$ alkyl group, $Y^3$ is one of O, S, Se, and Te, $Y^4$ is one of N and $NR^{18}$, $Y^5$ is one of $CR^{19}$ and $C=C(R^{20})(CN)$, each of $R^1$ to $R^3$, $R^{11}$, $R^{12}$ and $R^{15}$ to $R^{20}$ are independently one of hydrogen, a substituted or unsubstituted $C_1$ to $C_{30}$ alkyl group, a substituted or unsubstituted $C_6$ to $C_{30}$ aryl group, a substituted or unsubstituted $C_4$ to $C_{30}$ heteroaryl group, a halogen, a cyano group (—CN), a cyano-containing group and combination thereof, m1 is 0 or 1, m2 is an integer ranging from 0 to 4, n is 0 or 1, each of $R^{21}$ to $R^{23}$ are independently one of hydrogen, a halogen, a cyano group (—CN), a cyano-containing group, a substituted or unsubstituted $C_1$ to $C_6$ alkyl group, a substituted or unsubstituted $C_1$ to $C_6$ alkoxy group, and a combination thereof, and p is an integer ranging from 0 to 3, q is an integer ranging from 0 to 4, and r is an integer ranging from 0 to 5.

15. The organic photoelectric device of claim 9, wherein the compound shows a light absorption curve having a full width at half maximum (FWHM) of about 50 nm to about 110 nm in a thin film state.

16. The organic photoelectric device of claim 9, wherein the compound has a thermal decomposition of greater than or equal to about 280° C.

17. An image sensor comprising the organic photoelectric device of claim 9.

18. The image sensor of claim 17, further comprising:
a semiconductor substrate integrated with a plurality of first photo-sensing devices configured to sense light in a blue wavelength region and a plurality of second photo-sensing devices configured to sense light in a red wavelength region, wherein the organic photoelectric device is on the semiconductor substrate and is configured to sense light in a green wavelength region.

19. The image sensor of claim 18, further comprising:
a color filter layer between the semiconductor substrate and the organic photoelectric device, the color filter layer including a blue filter configured to selectively transmit light in the blue wavelength region and a red filter configured to selectively transmit light in the red wavelength region.

20. The image sensor of claim 18, wherein the first photo-sensing devices and the second photo-sensing devices are stacked in a vertical direction on the semiconductor substrate.

21. The image sensor of claim 17, wherein
the organic photoelectric device is a green photoelectric device, and
the green photoelectric device, a blue photoelectric device configured to sense light in a blue wavelength region, and a red photoelectric device configured to sense light in a red wavelength region are stacked.

22. An electronic device comprising the image sensor of claim 17.

* * * * *